(12) United States Patent
Riebel-Bommarius et al.

(10) Patent No.: US 7,163,815 B2
(45) Date of Patent: Jan. 16, 2007

(54) METHODS AND COMPOSITIONS FOR NAD(P)(H) OXIDASES

(75) Inventors: Bettina Riebel-Bommarius, Atlanta, GA (US); Andreas Bommarius, Atlanta, GA (US); Phillip Gibbs, Atlanta, GA (US); William Wellborn, Marietta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 11/045,874

(22) Filed: Jan. 28, 2005

(65) Prior Publication Data

US 2005/0196788 A1 Sep. 8, 2005

Related U.S. Application Data

(63) Continuation of application No. PCT/US03/024067, filed on Jul. 31, 2003.

(60) Provisional application No. 60/399,850, filed on Jul. 31, 2002.

(51) Int. Cl.
   - C12N 9/04 (2006.01)
   - C12N 9/54 (2006.01)
   - C12N 1/20 (2006.01)
   - C12P 7/22 (2006.01)
   - C07H 21/06 (2006.01)

(52) U.S. Cl. ............. 435/190; 435/221; 435/156; 435/69.1; 435/252.2; 536/23.2

(58) Field of Classification Search ........... 435/189, 435/69.1, 190
   See application file for complete search history.

(56) References Cited

U.S. PATENT DOCUMENTS 5,336,608 A * 8/1994 Niimura et al. .......... 435/189
6,489,149 B1 12/2002 Shao et al.

FOREIGN PATENT DOCUMENTS

EP 1176203 A1 1/2002

OTHER PUBLICATIONS

Knorr et al. EMBL(gene bank database) AB035801.*
Skare et.al. J. Clinc. Invst. 1995 vol. 96, pp. 2380-2392.*
A. Zaks, "Industrial biocatalysis". Curr. Opin. Chem. Biol. May 2001. 130-136.
A. Liese and M. V. Filbo, "Production of fine chemicals using biocatalysis". Curr. Opin. Biotechnol. Oct. 1999. 595-603.
J. D. Rozzell, "Biocatalysis at commercial scale: Myths and realities", Chimica Oggi 1999. 42-47.
A.S. Bommarius. M. Schwarm and K. Drauz, "Comparison of different chemoenzymatic process routes to enantiomerically pure amino acids". Chimia 2001. 55. 50-59.
D.A. Evans, T.C. Britton, J.A. Ellman and R.L. Dorow, 1990, "The asymmetric synthesis of α-amino acids. Electrophilic azidation of chiral imide enolates, a practical approach to the synthesis of (R)- and (S)-α-azido carboxylic acids". J. Am. Chem. Soc., 112 4011-4030.
U. Groth, C. Schmeck and U. Schöllkopf. 1993. "Asymmetric synthesis of α-amino acid benzyl esters via the bisbenzyl bislactim ether of cyclo(-L-Val-Gly-)". Liebigs Ann. Chem., 321-323.
W. Hummel, 1997. "New alcohol dehydrogenases for the synthesis of chiral compounds". Adv. Biochem. Eng. Biotechnol.. 58, 145-84.
M.J. Kim and G.M. Whitesides. 1988. "L-Lactate dehydrogenase: substrate specificity and use as a catalyst in the synthesis of homochiral 2-hydroxy acids", J. Am. Chem. Soc.. 110. 2959-64.
H.K.W. Kallwass, 1992. "Potential of R-2-hydroxyisocaproate dehydrogenase from lactobacillus casei foe stereospecific reductions". Enzyme Microb. Technol.. 14. 28-35.
G. Krix, A.S. Bommarius. K. Drauz, M. Kottenbahn. M. Schwarm and M.- R. Kula, 1997. "Enzymatic reduction of α-keto acids leading to L-amino acids or D-hydroxy Acids", J. Biotechnology, 53, 29-39.
Y. Asano, A. Yamada. Y. Kato. K. Yamaguchi. Y. Hibino. K. Hirai and K. Kondo. 1990. "Enantioselective synthesis of (S)-amino acids by phenylalanine dehydrogenase from *Bacillus sphaericus*: Use of natural and recombinant enzymes". J. Org. Chem., 55. 5567-5571.
C.W. Bradshaw, C.II. Wong, W. Hummel and M.-R. Kula, 1991, "Enzyme-catalyzed asymmetric synthesis of (S)-2-amino-4-phenylbutanoic acid and (R)-2-hydroxy-4-phenylbutanoic acid", Biorg. Chem., 19. 29-39.
R.L. Ilanson. J.M. Howell. T.L. LaPorte. M.J. Donovan. D.L. Cazzulino, V.V. Zannella, M.A. Montana, V.B. Nanduri. S.R. Schwartz, R.F. Eiring, S.C. Durand, J.M. Wasylyk. W.L. Parker, M.S. Liu. B.J. Okuniewicz, B. Chen, J.C. Harris, K.J. Natalie, K. Ramig, S. Swaninathan. V.W. Rosso. S.K. Pack, B.T. Lotz, P.J. Bernot. A. Rusowicz, D.A. Lust, K.S. Tse, J.J. Venit. L.J. Szarka, and R.N. Patel, 2000. "Synthesis of allysine ethylene acetal using phenylalanine dehydrogenase from Thermoactinomyces intermedius", Enzyme Microb Technol, 26. 348-358.

(Continued)

*Primary Examiner*—Rebecca E. Prout
*Assistant Examiner*—Mohammad Meah
(74) *Attorney, Agent, or Firm*—Troutman Sanders LLP

(57) ABSTRACT

The present invention is directed to compositions and methods comprising NAD(P)H oxidases, particularly bacterial oxidases, nucleic acids, recombinant plasmid vectors and recombinant proteins therein encoded, and host cells comprising the oxidases and nucleic acids. The present invention also comprises an isolated bacterial oxidase that oxidizes both NADH and NADPH. Methods for producing the enzymes and enzymatic reactions comprising use of NAD(P)H oxidases and products of such reactions are also disclosed.

9 Claims, 11 Drawing Sheets

OTHER PUBLICATIONS

R.L. Hanson, M. D. S.. A. Bancrjee. D.B. Brzozowski, B.-C. Chen, B.P. Patel, C.G. McNamee. G.A. Kodersha, D.R. Kronenthal. R.N. Patel and L.J. Szarka. Bioorganic & Medicinal Chemistry 1999. 7, 2247-2252.

A. Willetts, 1997. "Structural studies and synthetic applications of Baeyer-Villiger monooxygenases". Trends Biotechnol., 15. 55-62.

H.K. Chenault. G.M. Whitesides. Appl. Biochem. Biotechnol. 1987, 14, 147-97.

E. Keinan, K.K. Seth. R.J. Lamed. Ann. NY Acad. Sciences (Enzyme Engineering 8) 1987. 501. 130-150.

W. Hummel. M.-R. Kula. Eur. J. Biochem. 1989. 184. 1-13.

R. Wichmann. C. Wandrey. A.F. Bueckmann. M.-R. Kula, J. Biotechnol. 1981. 23. 2789-2802.

U. Kragl, D. Vasie-Racki, C. Wandrey. Chem. Ing. Tech, 1992, 64. 499-509.

V.I. Tishkov, A.G. Galkin. V.V. Fedorchuk, P.A. Savitsky, A.M. Rojkova, H. Gieren, M.-R. Kula, Biotechnol. Bioeng. 1999, 64, 187-93.

K. Seelbach, B. Riebel, W. Hummel, M.-R. Kula. V.I. Tishkov, A.M. Egorov. C Wandrey, U. Kragl. Tetrahedron Letters 1996, 37. 1377-80.

C.-H. Wong, G.M. Whitesides, J. Amer. Chem. Soc. 1981, 103. 4890-4899.

C.-H. Wong, D.G. Drueckhammer. Bio/technology 1985. 3, 649-651.

M. Kataoka, L.P. Rohani. K. Yamamoto. M. Wada. H. Kawabata. K. Kita. H. Yanase, S. Shimizu, Appl. Microbiol. Biotechnol. 1997, 48, 699-703.

R.P. Ross. A. Claiborne, J. Mol. Biol. 1992, 227, 658-71.

J. Matsumoto. M. Higushi. M. Shimada. Y. Yamamoto, Y. Kamio, Biosci. Biotechnol Biochem. 1996. 60. 39-43.

D.E. Ward, C.J. Donnelly, M.E. Mullendore, J. van der Oosi, W.M. de Vos. and E.J. Crane 3rd. Eur. J. Biochem. 2001. 268, 5816-23.

Y. Yamamoto. Y. Kamio, Tanpakushiisu Kakusan Koso 2001, 46, 726-32.

T. Ohshima and K. Soda, 1990, "Biochemistry and biotechnology of amino acid dehydrogenases", Adv. Biochem. Eng./Biotech., 42. 187-209.

W. Hummel. "Large-scale applications of NAD(P)-dependent oxidoreductases: recent developments", TIBTECH 1999. 17. 487-492.

M.-R. Kula and C. Wandrey. 1987, "Continuous enzymatic transformation in an enzyme-membrane-reactor with simultaneous NADH regeneration". Meth. Enzymol. 136. 9-21.

G.L. Lemiére. J.A. Lepoivre and F.C. Alderweireldt. 1985, "HLAD-catalyzed oxidations of alcohols with acetaldehyde as a coenzyme recycling substrate". Tetrahedron Lett., 26, 4527-28.

M.D. Bednarski, H.K. Chenault, E.S. Simon and G.M. Whitesides, 1987. "Membrane-enclosed enzymic catalysis (MEEC): a useful, practical new method for the manipulation of enzymes in organic synthesis", J. Amer. Chem. Soc., 109, 1283-85.

H.K. Chenault and G.M. Whitesides. 1989, "Lactate dehydrogenase-catalyzed regeneration of NAD from NADH for use in enzyme-catalyzed synthesis", Bioorg. Chem.,17. 400-9.

G. Carrea, R. Bovara, R. Longhi and S. Riva, 1985. "Preparation of 12-ketochenodeoxycholic acid from cholic acid using coimmobilized 12α-hydroxysteroid dehydrogenase and glutamate dehydrogenase with NADP+ cycling at high efficiency", Enz. Microb. Technol. 7. 597-600.

L.G. Lee and G.M. Whitesides, 1985, "Enzyme-catalyzed organic synthesis: a comparison of strategies for in situ regeneration of NAD from NADH", J. Am. Chem. Soc., 107, 6999-7008.

H.J. Park. C.O. Reiser, S. Kondruweit, H. Erdmann, R.D. Schmid and M. Sprinzl. 1992. "Purification and characterization of a NADH oxidase from the thermophile Thermus thermophilus IIB8", Eur. J. Biochem., 205, 881-5.

R.E. Altomare, J. Kohler, P.F. Greenfield and J.R. Kittrell, 1974, "Deactivation of immobilized beef liver catalase by hydrogen peroxide", Biotechnol. Bioeng.. 16. 1659-73.

K. Koike, T. Kobayashi, S. Ito and M. Saitoh. 1985, "Purification and characterization of NADH Oxidase from a strain of Leuconostoc mescrentoides", J. Biochem., 97, 1279-1288.

R.P. Ross and A. Claiborne. 1991, "Cloning, sequence and overexpression of NADH peroxidase from Streptococcus faccalis 10Cl. Structural relationship with the flavoprotein disulfide reductases", J. Mol. Biol., 221, 857-871.

R.P. Ross and A. Claiborne, 1992, "Molecular Cloning and Anaylsis of the Gene Encoding the NADH-Oxidase from Streptococcus laecalis 10C1. Comparison with NADH-Peroxidase and the Flavoprotein Disulfide Reductases", J. Mol. Biol., 227, 658-671.

S.N. Peterson, P.C. Hu. K.F. Bott and C.A. Hutchinson 3rd. 1993. "A survey of the Mycoplasma genitalium genome by using random sequencing", J. Bacteriol., 175, 7918-7930.

J. Matsumoto. M. Higushi, M. Shimada, Y. Yamamoto and Y. Kamio, 1996, "Molecular cloning and sequence anaylsis of the gene encoding the H2O-Forming NADH Oxidase from Streptococcus mutans". Biosci. Biotech. Biochem., 60, 39-43.

C.J. Bult, O. White, G.J. Olsen, L. Zhou. R.D. Fleischmann, G.G. Sutton, J.A. Blake. L.M. FitzGerald, R.A. Clayton, J.D. Gocayne, A.R. Kerlavage, B.A. Dougherty, J.F. Tomb, M.D. Adams, C.I. Reich, R. Overbeek, E.F. Kirkness, K.G. Weinstock, J.M. Merrick. A. Glodek. J.L. Scott, N.S. Geoghagen, J.C. Venter, 1996, "Complete genome sequence of the methanogenic archaeon. methanococcus jannaschii", Science, 273, 1058-1073.

V. Natarajan, S.M. Cramer. J. Chromatography A 2000. 876, 63-73.

A. Kundu, S. Vunnum, S.M. Cramer, J. Chromatography A 1995, 707, 57-67.

M. Wolberg, W. Hummel, M. Mueller, Chemistry 2001, 7, 4562-71.

J. Haberland, A. Kriegesmann, E. Wolfram, W. Hummel, A. Liese, Appl. Microbiol Biotechnol, 2002, 58.595-9.

S. Lindsay, D. Brosnahan and G.D. Watt. 2001, "Hydrogen peroxide formation during iron deposition in horse spleen ferritin using O2 as an oxidant". Biochemistry. 40. 3340-7.

M. Zhou. Z. Diwu, N. Panchuk-Voloshina, R.P. Haugland. 1997. "A stable nonfluorescent derivative of resorulin for the fluorometric determination of trace hydorgen peroxide: applications in detecting the activity of phagocyte NADPH oxidase and other oxidases". Anal. Biochem., 253, 162-168.

J.G. Mohanty, J.S. Jaffe, E.S. Schulman and D.G. Raible, 1997, "A highly sensitive fluorescent micro-assay of H2O2 release from activated human leukocytes using a dihydroxyphenoxazine derivative", J. Immunol. Methods, 202, 133-141.

B.R. Riebel. P.R. Gibbs. W.B. Wellborn and A.S. Bommarius, "Cofactor regeneration of NAD+ from NADH: novel water-forming NADH oxidases", Adv. Synth. Catal. 2002, 344, 1156-1168.

B.R. Riebel, P.R. Gibbs, W.B. Wellborn and A.S. Bommarius, "Cofactor regeneration of both NAD+ from NADH and NADP+ from NADPH: NADH oxides from Lactobacillus sanfranciscensis", Adv. Synth. Catal. 2003, 345, 707-712.

Wright et al., Gene 1992, 113. 55-65.

Firestine et al., Chemistry & Biology 1996, 3, 779-783.

Balbas, P. and Bolivar F. "Design and construction of expression plasmid vectors in E. coli". Methods Enzymology 185. 14-37.

Riley J. Butler R, Finniear R, Jenner D. Powell S. Anand R. Smith J C. Markahm A F (1990). "A novel. rapid method for the isolation of terminal sequences from yeast artificial chromosome (YAC) clones." Nucl Acids Res. 18, 8186.

Triglia T. Peterson M G. Kemp D J (1988). "A procedure-for in vitro amplification of DNA segments that lie outside the boundaries of known sequences." Nucleic Acids Res. 16, 8186.

Dordick et al. J. Am. Chem. Soc. 194, 1994, 116, 5009-5010.

Okahata et al. Tetrahedron Lett. 1997. 38, 1971-1974.

Adlercreutz et al. Bicatalysis 1992, 6, 291-305.

Goto et al. Biotechnol. Techniques 1997. 11, 375-378.

St Clair et al. Angew Chem Int Ed Engl Jan. 2000 39(2). 380-383.

Eigen M. and Gardinger W. (1984) "Evolutionary molecular engineering based on RNA replication." Pure & Appl. Chem. 56(8). 967-978.

Chen & Arnold (1991) "Enzyme engineering for nonaqueous solvents: random mutagenesis to enhance activity of subtilisin E in polar organic media." Bio/Technology 9, 1073-1077.

Horwitz, M. and L. Loeb (1986) "Promoters Selected From Random DNA-Sequences" Proc Natl Acad Sci USA. 83(19): 7405-7409.

Dube, D. and L. Loeb (1989) "Mutants Generated By The Insertion Of Random Oligonucleotides Into The Active-Site Of The Beta-Lactamase Gene" Biochemistry 28(14): 5703-5707.

Stemmer PC (1994) "DNA shuffling by random fragmentation and reassembly: In vitro recombination for molecular evolution." Proc Natl Acad Sci USA. 91: 10747-10751.

Stemmer PC (1994). "Rapid evolution of a protein in vitro by DNA shuffling." Nature. 370:389-391.

Roberts J., Stella V.J. and Decedue C.J. (1985) "A colorimetric assay of pancreatic lipase: rapid detection of lipase and colipase separated by gel filtration." Lipids 20(1): 42-45.

Pratt R.F. Faraci W.S. and Govardhan C.P. (1985) "A direct spectrophotometric assay for D-alanine carboxypeptidases and for the esterase activity of beta-lactamases." Anal. Biochem. 44(1):204-206.

* cited by examiner

METHODS AND COMPOSITIONS FOR NAD(P)(H) OXIDASES

CROSS-REFERENCE TO RELATED APPLICATIONS

This application, filed Jan. 28, 2005, is a continuation of PCT/US2003/024067, filed Jul. 31, 2003, which claims the priority of U.S. Provisional Patent Application Ser. No. 60/399,850, filed Jul. 31, 2002.

FIELD OF THE INVENTION

The present invention relates to bacterial NAD(P)H oxidases, their purification, nucleic acids coding for them and vehicles and constructs comprising the nucleic acids or expressed products of the nucleic acids, and products made from enzymatic reactions using the oxidases.

BACKGROUND OF THE INVENTION

Enantiomerically pure compounds (EPCs), especially amino and hydroxy acids as well as alcohols, amines, and lactones are increasingly useful in the pharmaceutical, food, and crop protection industries as building blocks for novel compounds not accessible through fermentation [1–4] as well as for asymmetric synthesis templates.[5–6] One very advantageous route to a wide variety of EPCs is the use of dehydrogenases, to afford either reduction of keto compounds or oxidation of alcohol or amine groups. The repertoire of dehydrogenases useful for synthesis of EPCs encompasses alcohol dehydrogenases (ADHs) [7], D- and L-lactate dehydrogenases (LDHs) [8], D- or L-hydroxyisocaproate dehydrogenases (D- or L-HicDHs) [9,10], or amino acid dehydrogenases such as leucine dehydrogenase (LeuDH) [10], phenylalanine dehydrogenase (PheDH) [11–13] or glutamate dehydrogenase (GluDH).[14] Monooxygenases have been used to synthesize, regio- and enantioselectively, lactones from cyclic ketones useful in the flavor and fragrance industries.[15]

Dehydrogenases and monooxygenases need nicotinamide-based cofactors, such as $NAD^+$ and $NADP^+$ or their reduced equivalents, NADH and NADPH, to function. Economic use of dehydrogenases and cofactor necessitates cofactor regeneration.[16] Cofactor costs, for example, $90 per gram for NAD+ have to be considered and having cofactors regenerated [17] would cut costs by the turnover number for such cofactors, between 100 and up to 600,000 [18].

Cofactor regeneration with alcohol dehydrogenases can be performed by using the same enzyme for in-situ substrate conversion and cofactor regeneration, usually employing isopropanol as co-substrate, as demonstrated with (S)-ADH from *Thermoanaerobium brockii* for both NADH and NADPH [19] and with (R)-ADH from *L. brevis* [20] for NADPH; this coupled-substrate approach, however, suffers from equilibrium limitations. The more common coupled-system approach, employing a separate second enzyme for regeneration, has been developed for reducing oxidized cofactors, $NAD^+$ or $NADP^+$, to NADH or NADPH. By far the most successful regeneration enzyme is formate dehydrogenase (FDH) for regeneration to either NADPH [24–25] or NADH, the latter even up to industrial scale [20–23]. Other options include the use of glucose 6-phosphate dehydrogenase [26] (to NADPH only) or of glucose dehydrogenase, GluDH [27–29]. For the opposite direction of regeneration, however, from NAD(P)H to oxidized cofactors $NAD^+$ or $NADP^+$, no universally accepted system exists.

There are some currently known NADH oxidases that are able to oxidize NADH to $NAD^+$ with simultaneous reduction of $O_2$ to either $H_2O_2$ or $H_2O$ [30–34]. Four-electron reduction to benign $H_2O$ is preferred over two-electron reduction to $H_2O_2$, which, even in small amounts, can deactivate either enzyme of the production-regeneration cycle. Addition of catalase as a possible remedy, to degrade the $H_2O_2$, increases complexity of the system to the point where three enzymes have to be coupled and adjusted as to their activity over time.

For reductive reactions with dehydrogenases or for monooxygenases, NAD(P)H has to be regenerated from $NAD(P)^+$. For this problem, the system formate dehydrogenase (FDH)/formate is now used almost universally [35–37

$$HCOOH + NAD^+ \rightarrow NADH + H^+ + CO_2 \qquad (1)$$

FDH functions as a universal regeneration enzyme in tandem with dehydrogenases catalyzing extremely enantioselective reduction reactions.[38–39]

For oxidative reactions requiring regeneration of NAD $(P)^+$ from NAD(P)H, prior to the present invention, no universal cofactor regeneration system was known. Alcohol dehydrogenase (ADH) itself can be utilized to catalyze both the oxidative production reaction as well as the reductive regeneration reaction by adding isopropanol which is oxidized to acetone, but such a scheme tends to be equilibrium-limited and plagued by deactivation of ADH.[40] Both the ADH and the lactate dehydrogenase (LDH) systems [41] cannot take NADPH, in contrast to glutamate dehydrogenase (GluDH), which has been utilized to reduce α-ketoglutarate to L-glutamate.[42,43] NADH oxidases from thermophiles have been employed which regenerate NAD+ from NADH by reducing $O_2$ to $H_2O_2$.[44]

What is needed are enzymes that regenerate NAD(P)H to oxidized cofactors NAD+ and NADP+ and synthesis methods that employ such enzymes alone or in coupled reactions. What is also needed are enzymes that perform the oxidation of NADH to $NAD^+$ with the concomitant reduction of molecular oxygen to water as a solution to the cofactor regeneration problem from NADH to $NAD^+$. Further, what is needed are methods for efficiently isolating the enzymes.

SUMMARY OF THE INVENTION

The present invention comprises methods and compositions comprising NAD(P)H oxidases (NOX). Compositions of the present invention comprise NOX that have activity in NAD+ regeneration and that have activity for both NAD+ and NADP+ regeneration. Additionally, the NOX show concomitant reduction of molecular oxygen to water. NOX is expected to be produced easily and be available in sufficient amounts for large-scale use. Compositions of the present invention also include isolated NOX from *Borrelia burgdorferi* (BNOX) and from *Lactobacillus sanfranciscensis* (SFNOX).

Further compositions comprise nucleic acids that encode the NOX, and recombinant plasmid vectors, and cells comprising the NOX-encoding nucleic acids. Such compositions include recombinant plasmid vectors and cells where the NOX-encoding nucleic acids are found alone or are found in combination with other enzyme-encoding nucleic acids. For example, compositions of the present invention comprise a cell comprising at least one plasmid comprising an enzyme-encoding nucleic acid, wherein in at least one encoding nucleic acid expresses at least one NOX of the present invention. The vectors of the present invention may be separate, under the control of one or more promoters, i.e., functioning like an individual plasmid, or may be intercalated with other vector constructs or genomic sequences.

Compositions of the present invention comprise whole cell catalysts, wherein the cells comprise NOX proteins and/or NOX-encoding nucleic acids and also comprise other enzymes or nucleic acids encoding such enzymes, so that all or part of a coupled enzymatic reaction can occur under the correct conditions. For example, a whole cell catalyst could comprise at least NOX and/or NOX-encoding nucleic acids and a dehydrogenase and/or dehydrogenase-encoding nucleic acids.

Compositions of the present invention further comprise nucleic acids and proteins encoded thereby that are derived by mutation or alteration of the nucleic acids taught herein. Such mutated sequences encode proteins that have NAD(P)H activity and are used in the vectors, plasmids, constructs and whole cell catalysts taught herein. Additionally, such mutated sequences are contemplated in the methods steps taught herein, for example, in isolating or using the NOX sequences or proteins.

Methods of the present invention comprise methods for isolating NOX from cells and methods for producing recombinant NOX from cells. Novel methods for isolation of NOX from cells are provided herein that has utility for large-scale production of such enzymes. Methods for producing a recombinant NOX comprise cultivating a cell containing a construct comprising NOX encoding nucleic acid, and collecting the NOX produced by the cell.

The present invention also comprises methods of use of the NOX described herein in enzymatic reactions, and compositions of the products of such reactions. Some enzymatic reactions contemplated by the present invention comprise methods of producing one or more chiral enantiomer-enriched organic compounds in reactions comprising one or more NOX. Such enzymatic reactions may be performed in in vitro systems or in in vivo, living cell systems.

BRIEF DESCRIPTION OF THE DRAWINGS

FIG. 2A-2F are sequence comparisons for BNOX (A–C) and SFNOX (D–F).

DETAILED DESCRIPTION OF THE INVENTION

Figure 1A:
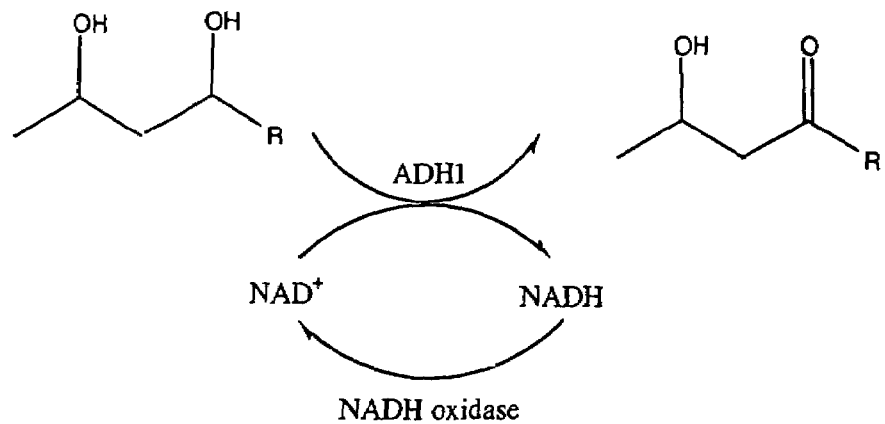
FIGS. 1A and 1B are schematic drawings of enzyme reactions of NOX.

The present invention comprises compositions and methods comprising novel NAD(P)H oxidases (NOX) from bacterial sources, and is particularly directed to SFNOX and BNOX. In summary, the compositions comprising NOX of the present invention include isolated enzymes, recombinantly produced enzymes, nucleic acids encoding the NOX, NOX sequences, proteins and recombinant constructs wherein the altered sequences are derived by mutational methods, vectors and plasmids comprising the NOX nucleic acids, and cells comprising the enzymes or nucleic acids encoding the NOX proteins. Compositions also include products made in enzymatic reactions in which NOX participates and enantiomer-enriches an unreacted racemate. SFNOX reacts with both NADH and NADPH, whereas BNOX reacts with NADH. Both enzymes reduce oxygen to water. As used herein, the term "NAD(P)H" means NADH or NADPH is the cofactor and, for enzymes capable of using both cofactors, means both NADH and NADPH.

The methods of the present invention include isolation of NOX proteins, and methods for enzymatic reactions comprising NOX. As used herein, NOX is understood to include the NAD(P)H oxidases disclosed herein, including bacterial oxidases that use NADH and NADPH as a cofactor, the enzymes that were isolated from $Borrelia$ $burgdorferi$ (BNOX) and from $Lactobacillus$ $sanfranciscensis$, any recombinant sequences derived from bacterial oxidases that use NADH and NADPH as a cofactor and those found in $Borrelia$ $burgdorferi$ (BNOX) and in $Lactobacillus$ $sanfranciscensis$ (SFNOX) and recombinant proteins expressed by those sequences in heterologous hosts, and any nucleic acid or amino acid variants with the oxidase activity of SFNOX and BNOX, and any mutants of bacterial oxidases that use NADH and NADPH as a cofactor and those found in $Borrelia$ $burgdorferi$ (BNOX) and in $Lactobacillus$ $sanfranciscensis$ or nucleic acids thereof.

In general, NADH oxidases (E.C. 1.6.-.-) catalyze the oxidation of NADH by simultaneously reducing molecular $O_2$ to either hydrogen peroxide, $H_2O_2$, in a two-electron reduction (reaction 2), or directly to water in a four-electron reduction (reaction 3).

$$NADH + O_2 + H^+ \rightarrow NAD^+ + H_2O_2 \quad (2)$$

$$2NADH + O_2 + 2H^+ \rightarrow 2NAD^+ + 2H_2O \quad (3)$$

NADH oxidases contain a second cofactor, presumably covalently bound FAD, as evidenced by the consensus sequence GXT(HS)AG near the N-terminus, and are widespread among different, evolutionary distinct organisms, such as humans, vertebrates, plants, $Drosophila$ and different strains of bacteria. Bacteria harbor both $H_2O_2$-forming and $H_2O$-forming NADH-oxidases. Owing to the deactivation of almost all proteins upon the exposure to $H_2O_2$, the $H_2O$-forming enzymes are superior as biocatalysts. Addition of catalase could potentially destroy the $H_2O_2$ formed, however, catalase itself features a very high $K_M$-value of 1.1 M [45], so that the enzyme is not particularly active at low $H_2O_2$ concentrations. Thermophilic bacteria usually only feature peroxide-producing NADH oxidases, which, despite their superior stability, renders them unfavorable for catalytic purposes. Water-producing NADH-oxidases can be found in various organisms, such as $Streptococcus$, $Enterococcus$, $Lactobacillus$, $Mycobacterium$, $Methanococcus$, or $Leuconostoc$. These organisms can contain both water- as well as peroxide-producing enzymes.

Various $H_2O$-producing NADH-oxidases have been found and described in the literature (see Table 1). None of them, however, has been characterized with respect to all of the properties relevant to use as a biocatalyst. In most cases, kinetic properties have not been reported.

TABLE 1

NADH oxidases

| Bacteria | Enzyme | Accession Code | Sequence data | Reference |
|---|---|---|---|---|
| Leuconostoc mesenteroides | Nox, H$_2$O | | | Koike, 1985 [46] |
| Enterococcus faecalis | NPX | P37062 (SwissProt) | Protein, Nucleotide | Ross et al. 1991 [47] |
| Enterococcus faecalis | Nox, H$_2$O | P37061 (SwissProt) | Protein, Nucleotide | Ross et al., 1992 [48] |
| Mycoplasma genitalis | Nox, H$_2$O | Q49408 (EMBL) | Protein, Nucleotide | Peterson, 1993 [49] |
| Streptococcus mutans | Nox, H$_2$O | D49951 (EMBL) | Protein, Nucleotide | Matsumoto, 1996 [50] |
| Mycoplasma pneumoniae | Nox, H$_2$O | P75389 (SwissProt) | Protein, Nucleotide | |
| Methanococcus japanicus | Nox, H$_2$O | Q58065 (EMBL) | Protein, Nucleotide | Bult, 1996 [51] |

Sequence analysis of the water-producing enzymes in all the organisms listed above reveals the same highly conserved cysteine residue, compared to a rather modest overall sequence similarity. This suggests that all these flavoproteins constitute a distinct class of FAD-dependent oxidoreductases, different from others such as glutathione reductase and thioredoxin reductase. Other properties of the enzymes listed above are similar: the molecular weight of the subunit hovers around 50 kD, all enzymes are dimers and contain 1 FAD per subunit, and all are inactivated by hydrogen peroxide.

Figure 1B:
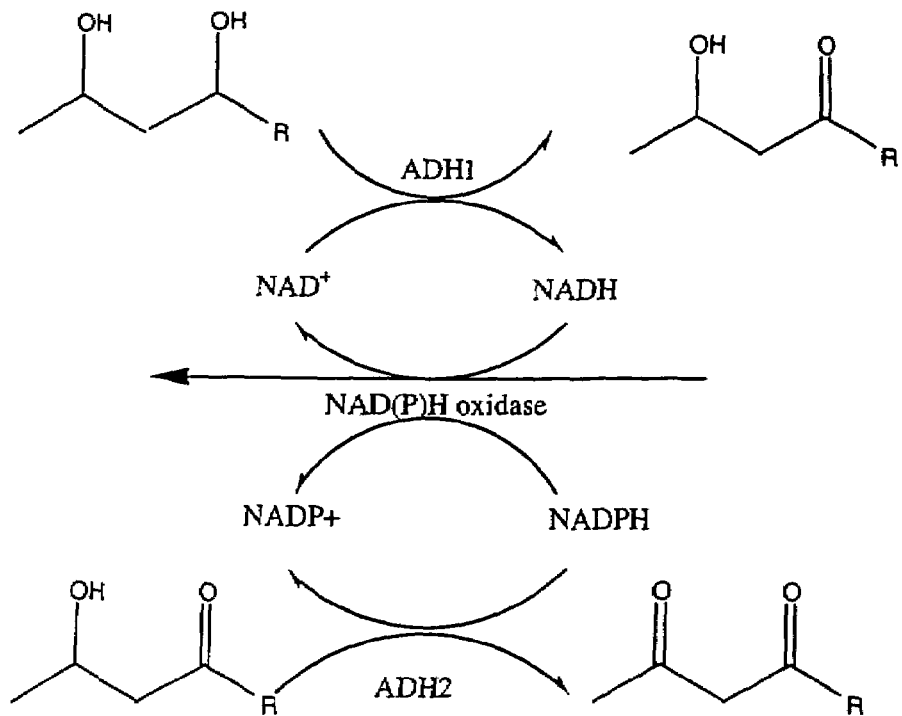

The present invention comprises compositions comprising NOX and methods of making and using NOX, wherein the NOX comprise bacterial oxidases that use NADH and NADPH as a cofactor, and NOX that were isolated from *Borrelia burgdorferi* (BNOX) and from *Lactobacillus sanfranciscensis*, (SFNOX). As NAD(P)H oxidases, both BNOX and SFNOX function to regenerate NAD+, (See FIG. 1A) and SFNOX has both NAD+ and NADP+ regeneration activity (See FIG. 1B). The ability of SFNOX to oxidize both cofactors renders it an extremely useful catalyst for coupled enzymatically-catalyzed oxidations. The present invention comprises bacterial oxidases that regenerate both NADP+ and NAD+. The present invention comprises novel NAD(P)H oxidases that reduce oxygen directly to water, which also makes them useful in coupled enzymatic reactions.

The NOX of the present invention participate in reactions where there is a complete conversion of one of the enantiomers in a racemic mixture, such as an alcohol to a ketone, leaving a highly enantiomer-enriched unreacted optical antipode of the original molecule, such as an alcohol. Dehydrogenases are capable of very specific enantiomeric selection and are used to prepare enantiomerically pure alcohols, hydroxy acids and amino acids as well as the corresponding ketones and keto acids. The dehydrogenase reaction requires the regeneration of the NADH or NADPH for cofactor activity, and thus, the NOX of the present invention have utility in coupled reactions with dehydrogenases including, but not limited to, alcohol dehydrogenase, lactate dehydrogenase and amino acid dehydrogenase. Products from such reactions include the resolution of racemic mixtures, such resolution dependent on the selectivity of the dehydrogenase used, and resulting in the unreacted racemate from the original racemic mixture, and the product of the enzyme reaction. For example, from a racemic mixture of an R/S-alcohol, in a reaction with an S-alcohol dehydrogenase, the resulting products are the unreacted enantiomer, the R-alcohol, and the resulting product, e.g, a ketone.

The NOX of the present invention are important in synthesis methods comprising enzyme reactions where the reactants have one or more chiral centers. An embodiment of the present invention comprises methods for enzyme reactions, comprising reacting at least one enzyme selective for one enantiomer of at least one chiral center of a compound with one or more chiral centers, with a reactant composition comprising the compound with one or more chiral centers, wherein the at least one enzyme requires a nicotinamide-based cofactor, and reacting the nicotinamide-based cofactor with one or more of the NOX of the present invention. In such methods where NAD+ is the cofactor, both SFNOX and BNOX individually or in combination could be used. In such methods where NADP+ is the cofactor, bacterial oxidases that use NADH and/or NADPH as a cofactor, such as SFNOX, could be used. Bacterial oxidases that use NADH and/or NADPH as a cofactor, including SFNOX, could be also used alone in methods where NADP+ and NAD+ are cofactors, as well as combinations of enzymes, such as bacterial oxidases that use NADH and NADPH as a cofactor, SFNOX and BNOX could be used in reactions where NAD+ and NADP+ are cofactors for enzymes in the reactions.

Embodiments of the present invention comprise isolated bacterial oxidases that use NADH and NADPH as a cofactor. Embodiments of the present invention also comprise SFNOX (SEQ ID NOs 2, 4 and 6) and BNOX (SEQ ID NOs 8, 10 and 12). The present invention also comprises nucleic acids of SFNOX (SEQ ID NOs 1, 3 and 5) and BNOX (SEQ ID NOs 7, 9 and 11).

```
SEQ ID 1 SFNOX
ATGAAAGTTATTGTAGTAGGTTGTACTCACGCTGGCACTTTTGCAGTTAAGCAAACGATT

GCCGATCACCCCGATGCAGATGTGACTGCATATGAAATGAATGATAACATTTCCTTTTTA

TCATGTGGAATCGCCCTTTACTTAGGTAAAGAAATTAAAA

ACAATGATCCCCGAGGGCTTTTCTACTCAAGTCCAGAAGAATTAAGCAATCTTGGAGCTAACGTCCAA

ATGCGTCATCAA

GTTACAAACGTTGATCCAGAAACAAAAACAATCAAAGTTAAAGATTTAATCACCAACGAAGAAAAAAC

AGAAGCATATGA

CAAATTAATTATGACCACTGGTTCTAAGCCTACTGTTCCTCCAATCCCTGGAATCGATAGTAGTCGCG

TTTACCTTTGTA
```

-continued

```
AAAACTATAACGATGCTAAAAAGTTATTTGAAGAAGCTCCCAAAGCTAAAACGATTACTATCATTGGT
TCTGGTTATATT
GGTGCCGAACTGGCTGAAGCCTACTCAAACCAAAATTATAACGTTAATTTAATTGATGGTCATGAACG
AGTTCTTTACAA
GTATTTTGATAAAGAATTTACTGATATTTTAGCCAAAGATTATGAAGCTCATGGTGTTAACCTGGTTC
TTGGTTCAAAAG
TAGCTGCTTTTGAAGAAGTCGATGATGAAATTATCACTAAAACCCTAGATGGTAAAGAAATTAAATCT
GATATTGCAATT
CTTTGTATCGGTTTCCGCCCTAACACTGAATTACTTAAAGGTAAAGTTGCCATGTTGGATAACGGTGC
AATCATTACTGA
TGAATACATGCATTCATCAAATCGCGACATTTTTGCTGCTGGTGATAGTGCCGCCGTTCACTACAACC
CCACTAATTCTA
ACGCCTACATTCCTTTAGCTACCAACGCCGTACGCCAAGGGAGATTAGTTGGCCTAAATCTGACTGAA
GACAAAGTAAAA
GACATGGGAACCCAATCTTCATCTGGTCTTAAACTATACGGTCGGACTTATGTCTCAACTGGAATCAA
TACGGCTCTTGC
TAAAGCCAATAATTTAAAAGTTAGCGAAGTAATCATAGCTGATAATTATCGTCCAGAATTTATGTTAT
CAACGGATGAAG
TTTTAATGTCATTAGTGTATGATCCTAAGACTCGTGTAATTTTGGGAGGGGCGCTTTCAAGTATGCAC
GATGTTTCGCAA
TCAGCGAACGTCTTATCAGTATGTATTCAAAATAAAAACACGATTGACGATTTAGCAATGGTGGATAT
GTTATTCCAACC
ACAATTTGATCGTCCGTTTAACTACTTAAACATTCTAGGCCAAGCTGCTCAAGCACAAGCTGACAAAG
CACATAAAtaa
SEQ ID 2 SF
MKVIVVGCTHAGTFAVKQTI
ADHPDADVTAYEMNDNISFL
SCGIALYLGKEIKNNDPRGLFYSSPEELSNLGANVQMRHQ
VTNVDPETKTIKVKDLITNEEKTEAYDKLIMTTGSKPTVPPIPGIDSSRVYLCKNYNDAKKLFEEAPK
AKTITIIGSGYI
GAELAEAYSNQNYNVNLIDGHERVLYKYFDKEFTDILAKDYEAHGVNLVLGSKVAAFEEVDDEIITKT
LDGKEIKSDIAI
LCIGFRPNTELLKGKVAMLDNGAIITDEYMHSSNRDIFAAGDSAAVHYNPTNSNAYIPLATNAVRQGR
LVGLNLTEDKVK
DMGTQSSSGLKLYGRTYVSTGINTALAKANNLKVSEVIIADNYRPEFMLSTDEVLMSLVYDPKTRVIL
GGALSSMHDVSQ
SANVLSVCIQNKNTIDDLAMVDMLFQPQFDRPFNYLNILGQAAQAQADKAHK
SEQ ID 3 SFNOXK2
ATGAAAGTTATTGTAGTAGGTTGTACTCACGCTGGCACTTTTGCAGTTAAGCAAACGATTGCCGATCA
CCCCGATGCAGA
TGTGACTGTATATGAAATGAATGATAACATTTCCTTTTTATCATGTGGAATCGCCCTTTACTTAGGTA
```

```
AAGAAATTAAAA
ACAATGATCCCCGAGGGCTTTTCTACTCAAGTCCAGAAGAATTAAGCAATCTTGGAGCTAACGTCCAA
ATGCGTCATCAA
GTTACAAACGTTGATCCAGAAACAAAAACAATCAAAGTTAAAGATTTAATCACCAACGAAGAAAAAAC
AGAAGCATATGA
CAAATTAATTATGACCACTGGCTCTAAGCCTACTGTTCCTCCAATCCCTGGAATCGATAGTAGTCGCG
TTTACCTTTGTA
AAAACTATAACGATGCTAAAAAGTTATTTGAAGAAGCTCCCAAAGCTAAAACGATTACTATCATTGGT
TCCGGTTATATT
GGTGCCGAACTGGCTGAAGCCTACTCAAACCAAAATTATAACGTTAATTTAATTGATGGTCATGAACG
AGTTCTTTACAA
GTATTTTGATAAAGAATTTACTGATATTTTAGCCAAAGATTATGAAGCTCATCGTGTTAACCTGGTTC
TTGGTTCAAAAG
TAGCTGCTTTTGAAGAAGTCGATGATGAAATTATCACTAAAACCCTAGATGGTAAAGAAATTAAATCT
GATATTGCAATT
CTTTGTATCGGTTTCCGCCCTAACACTGAATTACTTAAAGGTAAAGTTGCCATGTTGGATAACGGTGC
AATCATTACTGA
TGAATACATGCATTCATCAAATCGCGACATTTTTGCTGCTGGTGATAGTGCCGCCGTTCACTACAACC
CCACTAATTCTA
ACGCCTACATTCCTTTAGCTACCAACGCCGTACGCCAAGGGAGATTAGTTGGCCTAAATCTGACTGAA
GACAAAGTAAAA
GACATGGGAACCCAATCTTCATCTGGTCTTAAACTATACGGTCGGACTTATGTCTCAACTGGAATCAA
TACGGCTCTTGC
TAAAGCCAATAATTTAAAAGTTAGCGAAGTAATCATAGCTGATAATTATCGTCCAGAATTTATGTTAT
CAACGGATGAAG
TTTTAATGTCATTAGTGTATGATCCTAAGACTCGTGTAATTTTGGGAGGGGCGCTTTCAAGTATGCAC
GATGTTTCGCAA
TCAGCGAACGTCTTATCAGTATGTATTCAAAATAAAAACACGATTGACGATTTAGCAATGGTGGATAT
GTTATTCCAACC
ACAATTTGATCGTCCGTTTAACTACTTAAACATTCTAGGCCAAGCTGCTCAAGCACAAGCTGACAAAG
CACATAAAtaa
SEQ ID 4 SFNOXK2
MKVIVVGCTHAGTFAVKQTIADHPDADVTVYEMNDNISFLSCGIALYLGKEIKNNDPRGLFYSSPEEL
SNLGANVQMRHQ
VTNVDPETKTIKVKDLITNEEKTEAYDKLIMTTGSKPTVPPIPGIDSSRVYLCKNYNDAKKLFEEAPK
AKTITIIGSGYI
GAELAEAYSNQNYNVNLIDGHERVLYKYFDKEFTDILAKDYEAHGVNLVLGSKVAAFEEVDDEIITKT
LDGKEIKSDIAI
LCIGFRPNTELLKGKVAMLDNGAIITDEYMHSSNRDIFAAGDSAAVHYNPTNSNAYIPLATNAVRQGR
LVGLNLTEDKVK
DMGTQSSSGLKLYGRTYVSTGINTALAKANNLKVSEVIIADNYRPEFMLSTDEVLMSLVYDPKTRVIL
```

GGALSSMHDVSQ

SANVLSVCIQNKNTIDDLAMVDMLFQPQFDRPFNYLNILGQAAQAQADKAHK

SEQ ID NO.:5 SFNOX K6
ATGAAAGTTATTGTAGTAGGTTGTACTCACGCTGGCACTTTTGCAGTTAAGCAAACGATTGCCGATCA

CCCCGATGCAGA

TGTGACTGTATATGAAATGAATGATAACATTTCCTTTTTATCATGTGGAATCGCCCTTTACTTAGGTA

AAGAAATTAAAA

ACAATGATCCCCGAGGGCTTTTCTACTCAAGTCCAGAAGAATTAAGCAATCTTGGAGCTAACGTCCAA

ATGCGTCATCAA

GTTACAAACGTTGATCCAGAAACAAAAACAATCAAAGTTAAAGATTTAATCACCAACGAAGAAAGAAC

AGAAGCATATGA

CAAATTAATTATGACCACTGGTTCTAAGCCTACTGTTCCTCCAATCCCTGGAATCGATAGTAGTCGCG

TTTACCTTTGTA

AAAACTATAACGATGCTAAAAAGTTATTTGAAGAAGCTCCCAAAGCTAAAACGATTACTATCATTGGT

TCTGGTTATATT

GGTGCCGAACTGGCTGAAGCCTACTCAAACCAAAATTATAACGTTAATTTAATTGATGGTCATGAACG

AGTTCTTTACAA

GTATTTTGATAAAGAATTTACTGATATTTTAGCCAAAGATTATGAAGCTCATGGTGTTAACCTGGTTC

TTGGTTCAAAAG

TAGCTGCTTTTGAAGAAGTCGATGATGAAATTATCACTAAAACCCTAGATGGTAAAGAAATTAAATCT

GATATTGCAATT

CTTTGTATCGGTTTCCGCCCTAACACTGGATTACTTAAAGGTAAAGTTGCCATGTTGGATAACGGTGC

AATCATTACTGA

TGAATACATGCATTCATCAAATCGCGACATTTTTGCTGCTGGTGATAGTGCCGCCGTTCACTACAACC

CCACTAATTCTA

ACGCCTACATTCCTTTAGCTACCAACGCCGTACGCCAAGGGAGATTAGTTGGCCTAAATCTGACTGAA

GACAAAGTAAAA

GACATGGGAACCCAATCCTCATCTGGTCTTAAACTATACGGTCGGACTTATGTCTCAACTGGAATCAA

TACGGCTCTTGC

TAAAGCCAATAATTTAAAAGTTAGCGAAGTAATCATAGCTGATAATTATCGTCCAGAATTTATGTTAT

CAACGGATGAAG

TTTTAATGTCATTAGTGTATGATCCTAAGACTCGTGTAATTTTGGGAGGGGCGCTTTCAAGTATGCAC

GATGTTTCGCAA

TCAGCGAACGTCTTATCAGTATGTATTCAAAATAAAAACACGATTGACGATTTAGCAATGGTGGATAT

GTTATTCCAACC

ACAATTTGATCGTCCGTTTAACTACTTAAACATTCTAGGCCAAGCTGCTCAAGCACAAGCTGACAAAG

CACATAAAtaa

SEQ ID NO.: 6 SFNOXK6
MKVIVVGCTHAGTFAVKQTIADHPDADVTVYEMNDNISFLSCGIALYLGKEIKNNDPRGLFYSSPEEL

SNLGANVQMRHQ

VTNVDPETKTIKVKDLITNEERTEAYDKLIMTTGSKPTVPPIPGIDSSRVYLCKNYNDAKKLFEEAPK

-continued

AKTITIIGSGYI

GAELAEAYSNQNYNVNLIDGHERVLYKYFDKEFTDILAKDYEAHGVNLVLGSKVAAFEEVDDEIITKT

LDGKEIKSDIAI

LCIGFRPNTGLLKGKVAMLDNGAIITDEYMHSSNRDIFAAGDSAAVHYNPTNSNAYIPLATNAVRQGR

LVGLNLTEDKVK

DMGTQSSSGLKLYGRTYVSTGINTALAKANNLKVSEVIIADNYRPEFMLSTDEVLMSLVYDPKTRVIL

GGALSSMHDVSQ

SANVLSVCIQNKNTIDDLAMVDMLFQPQFDRPFNYLNILGQAAQAQADKAHK

SEQ ID NO.:7 BNOX
ATGATGAAAATAATAATTATTGGGGGCACATCAGCAGGAACTAGTGCCGCAGCTAAAGCA

AACCGCTTAAACAAAAAGCTAGACATTACTATCTATGAAAAAACAAATATTGTATCTTTT

GGAACCTGTGGCCTGCCTTACTTTGTGGGGGATTCTTTGACAACCCCAATACAATGATC

TCAAGAACACAAGAAGAATTCGAAAAAACTGGAATCTCTGTTAAAACTAACCACGAAGTT

ATCAAAGTAGATGCAAAAAACAATACAATTGTAATAAAAAATCAAAAAACAGGAACCATT

TTTAACAATACTTACGATCAACTTATGATAGCAACTGGTGCAAAACCTATTATTCCACCA

ATCAATAATATCAATCTAGAAAATTTTCATACTCTGAAAAATTTAGAAGACGGTCAAAAA

ATAAAAAAATTAATGGATAGAGAAGAGATTAAAAATATAGTGATAATTGGTGGTGGATAC

ATTGGAATTGAAATGGTAGAAGCAGCAAAAAATAAAAGAAAAAATGTAAGATTAATTCAA

CTAGATAAGCACATACTCAT

AGATTCCTTTGACGAAGAAATAGTCACAATAATGGAAGAAGAACTAACAAAAAAGGGGGTTAATCTTC

ATACAAATGAGT

TTGTAAAAAGTTTAATAGGAGAAAAAAAGGCAGAAGGAGTAGTAACAAACAAAAATACTTATCAAGCT

GACGCTGTTATA

CTTGCTACCGGAATAAAACCTGACACTGAATTTTTAGAAAACCAGCTTAAAACTACTAAAAATGGAGC

AATAATTGTAAA

TGAGTATGGCGAAACTAGCATAAAAAATATTTTTTCTGCAGGAGATTGTGCAACTATTTATAATATAG

TAAGTAAAAAAA

ATGAATACATACCCTTGGCAACAACAGCCAACAAACTTGGAAGAATAGTTGGTGAAAATTTAGCTGGG

AATCATACAGCA

TTTAAAGGCACATTGGGCTCAGCTTCAATTAAAATACTATCTTTAGAAGCTGCAAGAACAGGACTTAC

AGAAAAAGATGC

AAAAAAGCTCCAAATAAAATATAAAACGATTTTTGTAAAGGACAAAAATCATACAAATTATTATCCAG

GCCAAGAAGATC

TTTATATTAAATTAATTTATGAGGAAAATACCAAAATAATCCTTGGGCACAAGCAATAGGAAAAAAT

GGAGCCGTAATA

AGAATTCATGCTTTATCAATTGCAATCTATTCAAAACTTACAACAAAAGAGCTAGGGATGATGGATTT

CTCATATTCCCCACCCTTCTCAAGAACTTGGGATATATTAAATATTGCTGGCAATGCTGCCAAAtag

SEQ ID NO.: 8 BNOX
MMKIIIGGTSAGTSAAAKA

NRLNKKLDITIYEKTNIVSF

GTCGLPYFVGGFFDNPNTMI

-continued

SRTQEEFEKTGISVKTNHEV

IKVDAKNNTIVIKNQKTGTI

FNNTYDQLMIATGAKPIIPP

INNINLENFHTLKNLEDGQK

IKKLMDREEIKNIVIIGGGY

IGIEMVEAAKNKRKNVRLIQ

LDKHILIDSFDEEIVTIMEE

ELTKKGVNLHTNEFVKSLIGEKKAEGVVTNKNTYQADAVI

LATGIKPDTEFLENQLKTTKNGAIIVNEYGETSIKNIFSAGDCATIYNIVSKKNEYIPLATTANKLGR

IVGENLAGNHTA

FKGTLGSASIKILSLEAARTGLTEKDAKKLQIKYKTIFVKDKNHTNYYPGQEDLYIKLIYEENTKIIL

GAQAIGKNGAVI

RIHALSIAIYSKLTTKELGMMDFSYSPPFSRTWDILNIAGNAAK

SEQ ID NO.: 9 BNOX K1
ATGATGAAAATAATAATTATTGGGGGCACATCAGCAGGAACTAGTGCCGCAGCTAAAGCAAACCGCTT

AAACAAAAAGCT

AGACATTACTATCTATGAAAAAACAAATATTGTATCTTTTGGAACCTGCGGCCTGCCTTACTTTGTGG

GGGGATTCTTTG

ACAACCCCAATACAATGATCTCAAGAACACAAGAAGAATTCGAAAAAACTGGAATCTCTGTTAAAACT

AACCACGAAGCT

ATCAAAGTAGATGCAAAAAACAATACAATTGTAATAAAAAATCAAAAAACAGGAACCATTTTTAACAA

TACTTACGATCA

ACTTATGATAGCAACTGGTGCAAAACCTATTATTCCACCAATCAATAATATCAATCTAGAAAATTTTC

ATACTCTGAAAA

ATTTAGAAGACGGTCAAAAAATAAAAAAATTAATGGATAGAGAAGAGATTAAAAATATAGCGATAATT

GGTGGTGGATAC

ATTGGAATTGAAATGGTAGAAGCAGCAAAAAATAAAAGAAAAAATGTAAGATTAATTCAACTAGATAA

GCACATACTCAT

AGATTCCTTTGACGAAGAAATAGTCACAATAATGGAAGAAGAACTAACAAAAAAGGGGGTTAATCTTC

ATACAAATGAGT

TTGTAAAAAGTTTAATAGGAGAAAAAAAGGCAGGAGGAGTAGTAACAAACAAAAATACTTATCAAGCT

GACGCTGTTATA

CTTGCTACCGGAATAAAACCTGACACTGAATTTTTAGAAAACCAGCTTAAAACTACTAAAAATGGAGC

AATAATTGTAAA

TGAGTATGGCGAAACTAGCATAAAAAATATTTTTTCTGCAGGAGATTGTGCAACTATTTATAATATAG

TAAGTAAAAAAA

ATGAATACATACCCTTGGCAACAACAGCCAACAAACTTGGAAGAATAGTTGGTGAAAATTTAGCTGGG

AATCATACAGCA

TTTAAAGGCACATTGGGCTCAGCTTCAATTAAAATACTATCTTTAGAAGCTGCAAGAACGGGACTTAC

AGAAAAAGATGC

-continued

```
AAAAAGGCTCCAAATAAAATATAAAACGATTTTTGTAAAGGACAAAAATCATACAAATTATTATCCAG

GCCAAGAAGATC

TTTATATTAAATTAATTTATGAGGAAAATACCAAAATAATCCTTGGAGCACAAGCAACAGGAAAAAAT

GGAGCCGTAATG

AGAATTCATGCTTTATCAATTGCAATCTATTCAAAACTTACAACAAAAGAGCTAAGGATGATGGATTT

CTCATATTCCCCACCCTTCTCAAGAACTTGGGATATATTAAATATTGCTGGCAATGCTGCCAAAtag

SEQ ID NO.: 10 BNOX K1
MMKIIIIGGTSAGTSAAAKA

NRLNKKLDITIYEKTNIVSF

GTCGLPYFVGGFFDNPNTMI

SRTQEEFEKTGISVKTNHEA

IKVDAKNNTIVIKNQKTGTIFNNTYDQLMIATGAKPIIPPINNINLENFHTLKNLEDGQKIKKLMDRE

EIKNIAIIGGGY

IGIEMVEAAKNKRKNVRLIQLDKHILIDSFDEEIVTIMEEELTKKGVNLHTNEFVKSLIGEKKAGGVV

TNKNTYQADAVI

LATGIKPDTEFLENQLKTTKNGAIIVNEYGETSIKNIFSAGDCATIYNIVSKKNEYIPLATTANKLGR

IVGENLAGNHTA

FKGTLGSASIKILSLEAARTGLTEKDAKRLQIKYKTIFVKDKNHTNYYPGQEDLYIKLIYEENTKIIL

GAQATGKNGAVM

RIHALSIAIYSKLTTKELRMMDFSYSPPFSRTWDILNIAGNAAK

SEQ ID NO.: 11 BNOX K6
ATGATGAAAATAATAATTATTGGGGGCACATCAGCAGGAACTAGTGCCGCAGCTAAAGCAAACCGCTT

AAACAAAAAGCT

AGACATTACTATCTATGAAAAAACAAATATTGTATCTTTTGGAACCTGTGGCCTGCCTTACTTTGTGG

GGGGATTCTTTG

ACAACCCCAATACAATGATCTCAAGAACACAAGAAGAATTCGAAAAAACTGGAATCTCTGTTAAAACT

AACCACGAAGTT

ATCAAAGTAGATGCAAAAAACAATACAATTGTAATAAAAAATCAAAAAACAGGAACCATTTTTAACAA

TACTTACGATCA

ACTTATGATAGCAACTGGTGCAAAACCTATTATTCCACCAATCAATAATATCAATCTAGAAAATTTTC

ATACTCTGAAAA

ATTTAGAAGACGGTCAAAAAATAAAAAAATTAATGGATAGAGAAGAGATTAAAAATATAGTGATAATT

GGTGGTGGATAC

ATTGGAATTGAAATGGTAGAAGCAGCAAAAAATAAAAGAAAAAGTGTAAGATTAATTCAACTAGATAA

GCACATACTCAT

AGATTCCTTTGACGAAGAAATAGTCACAATAATGGAAGAAGAACTAACAAAAAAGGGGGTTAATCTTC

ATACAAATGAGT

TTGTAAAAAGTTTAATAGGAGGAAAAAAGGCAGAAGGAGTAGTAACAAACAAAAATACTTATCAAGCT

GACGCTGTTATA

CTTGCTACCGGAATAAAACCTGACACTGAATTTTTAGAAAACCAGCTTAAAACTACTAAAAATGGAGC

AATAATTGTAAA
```

```
-continued
TGAGTATGGCGAAACTAGCATAAAAAATATTTTTTCTGCAGGAGATTGTGCAACTATTTATAATATAG

TAAGTAAAAAAA

ATGAATACATACCCTTGGCAACAACAGCCAACAAACTTGGAACAATAGTTGGTGAAAATTTAGCTGGG

AATCATACAGCA

TTTAAAGGCACATTGGGCTCAGCTTCAATTAAAATACTATCTTTAGAAGCTGCAAGAACAGGACTTAC

AGAAAAAGATGC

AAAAAAGCTCCAAATAAAATATAAAACGATTTTTGTAAAGGACAAAAATCATACAAATTATTATCCAG

GCCAAGAAGATC

TTTATATTAAATTAATTTATGAGGAAAATACCAAAATAATCCTTGGGGCACAAGCAATAGGAAAAAAT

GGAGCCGTAATA

AGAATTCATGCTTTATCAATTGCAATCTATTCAAAGCTTACAACAAAAGAGCTAGGGATGATGGATTT

CTCATATTCCCCACCCTTCTCAAGAACTTGGGATATATTAAATATTGCTGGCAATGCTGCCAAAtag

SEQ ID NO.: 12 BNOX K6
B6 protein sequence
MMKIIIGGTSAGTSAAAKA

NRLNKKLDITIYEKTNIVSF

GTCGLPYFVGGFFDNPNTMI

SRTQEEFEKTGISVKTNHEV

IKVDAKNNTIVIKNQKTGTIFNNTYDQLMIATGAKPIIPPINNINLENFHTLKNLEDGQKIKKLMDRE

EIKNIVIIGGGY

IGIEMVEAAKNKRKSVRLIQLDKHILIDSFDEEIVTIMEEELTKKGVNLHTNEFVKSLIGGKKAEGVV

TNKNTYQADAVI

LATGIKPDTEFLENQLKTTKNGAIIVNEYGETSIKNIFSAGDCATIYNIVSKKNEYIPLATTANKLGR

IVGENLAGNHTA

FKGTLGSASIKILSLEAARTGLTEKDAKKLQIKYKTIFVKDKNHTNYYPGQEDLYIKLIYEENTKIIL

GAQAIGKNGAVI

RIHALSIAIYSKLTTKELGMMDFSYSPPFSRTWDILNIAGNAAK
```

SFNOX and BNOX disclosed herein only share a modest 32% amino acid sequence identity in between themselves and only 34% identity to the NOXs of either *Enterococcus faecalis* [48] or *Streptococcus mutans* [50], except for 55% between SFNOX and *E. faecalis*. The NOX coding genes from *Borrelia burgdorferi* (BNOX) and *Lactobacillus sanfranciscensis* (SFNOX) were isolated from the genomic DNA using gene specific primers derived from the coding sequence, SEQ. ID. NO.: 13–16.

Figure 2A:
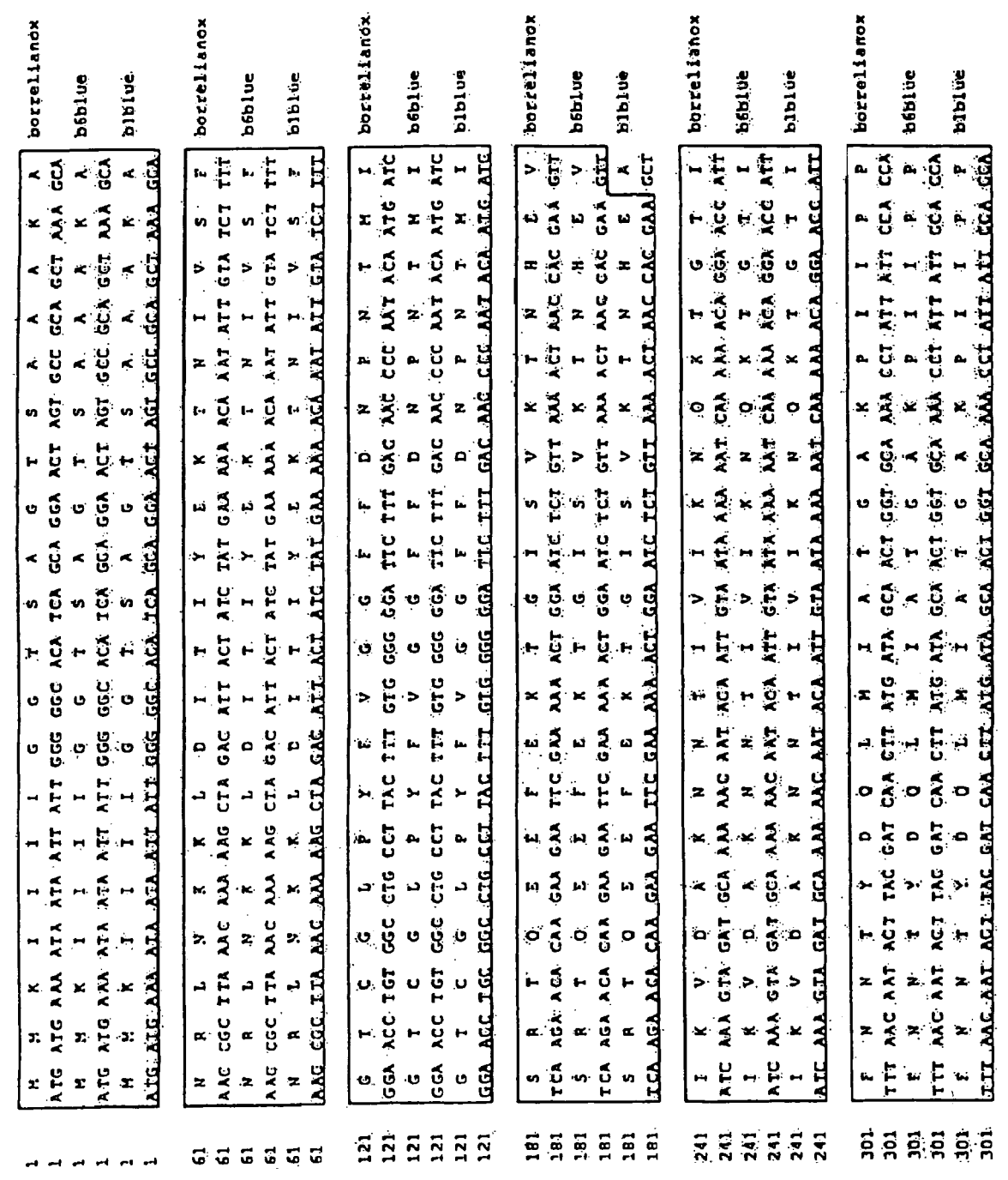
Figure 2B:
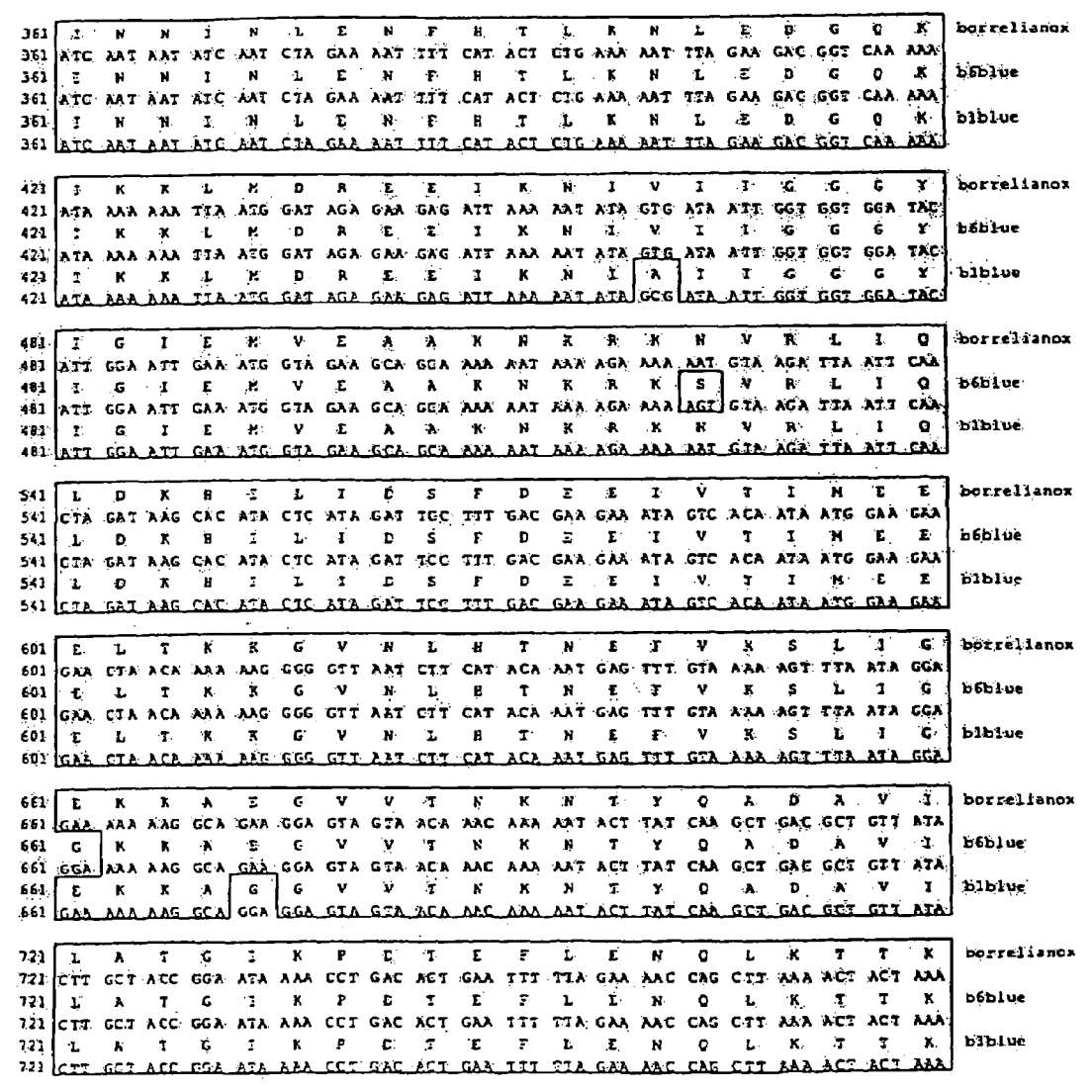
Figure 2C:
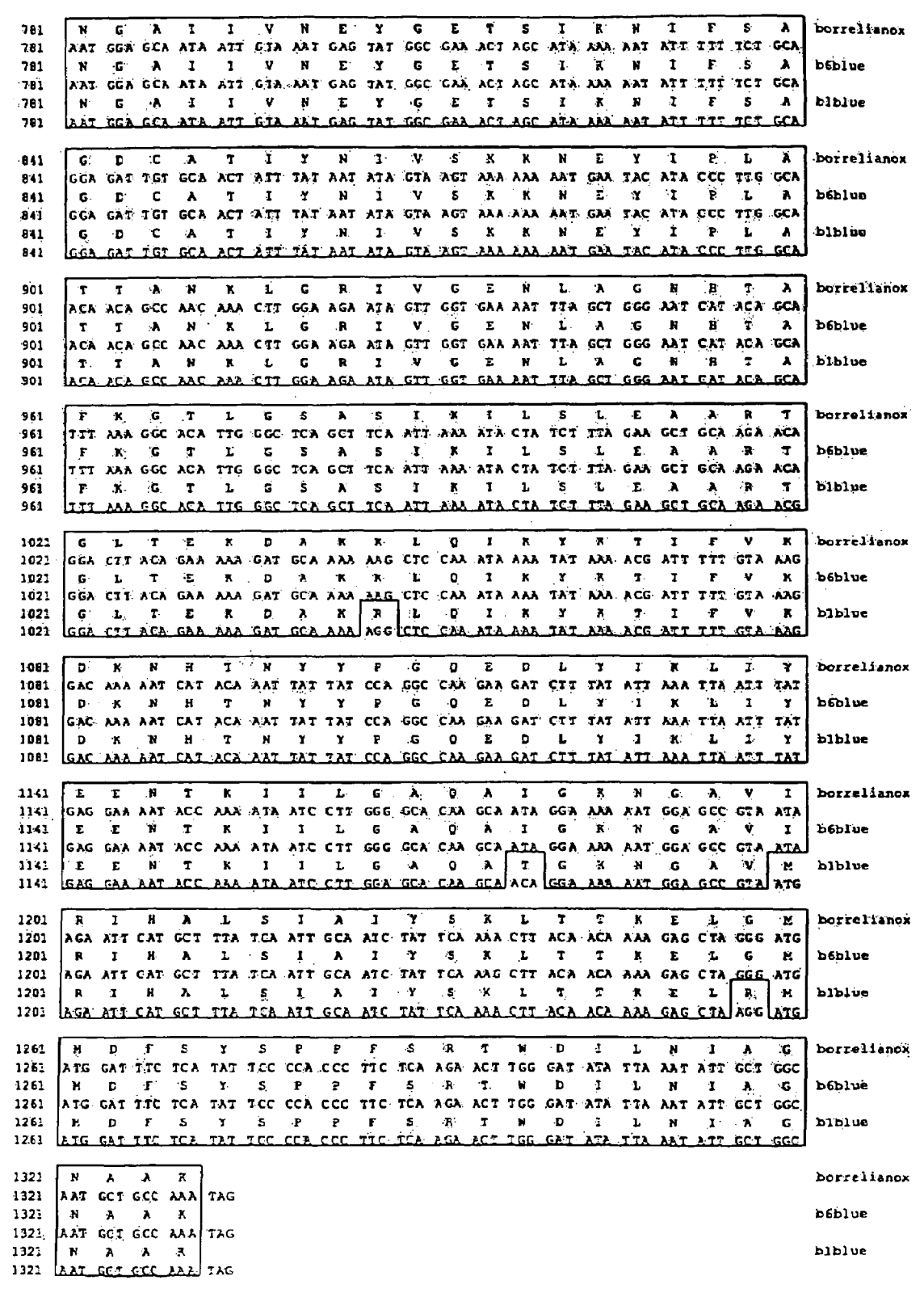
Figure 2D:
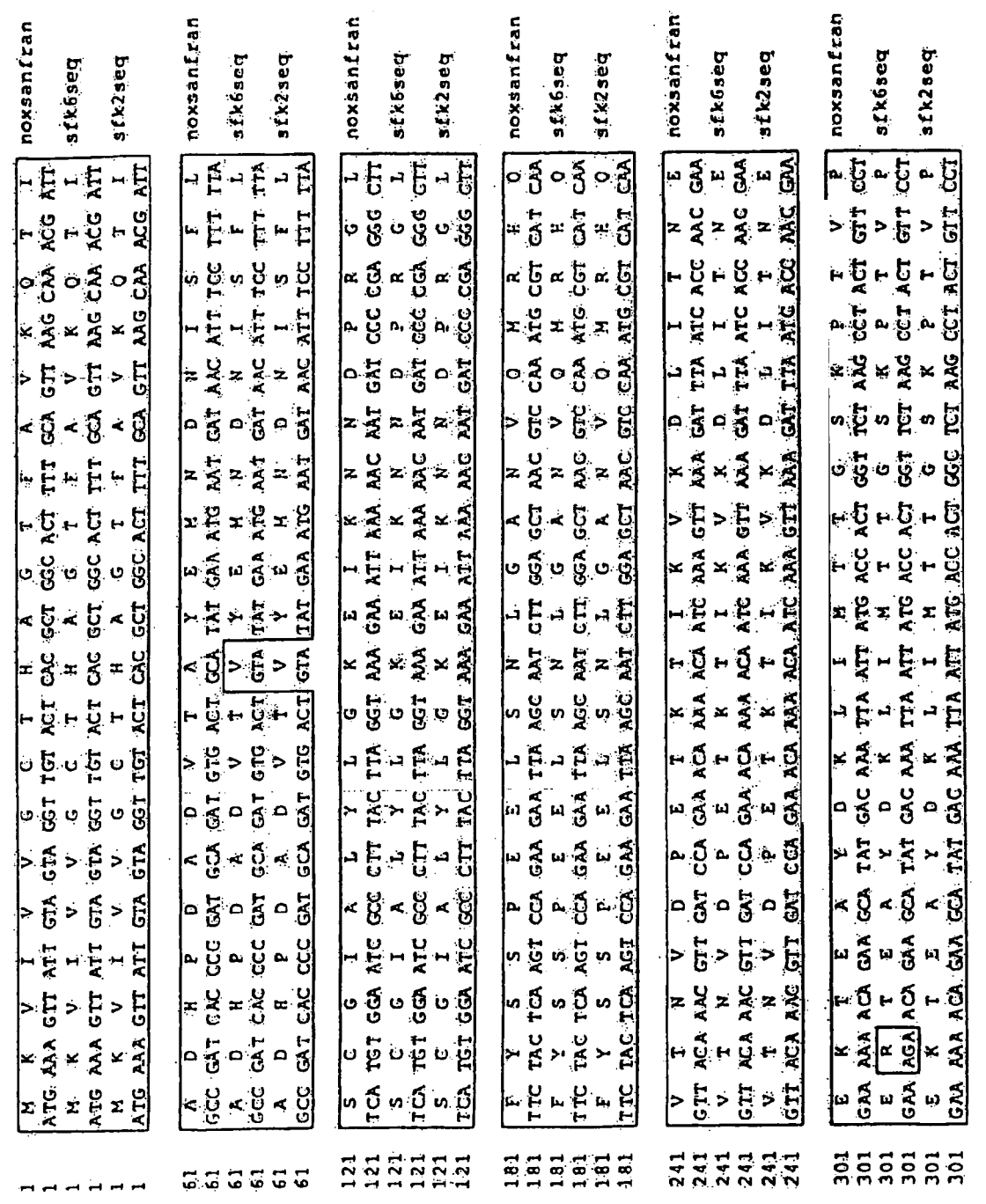
Figure 2E:
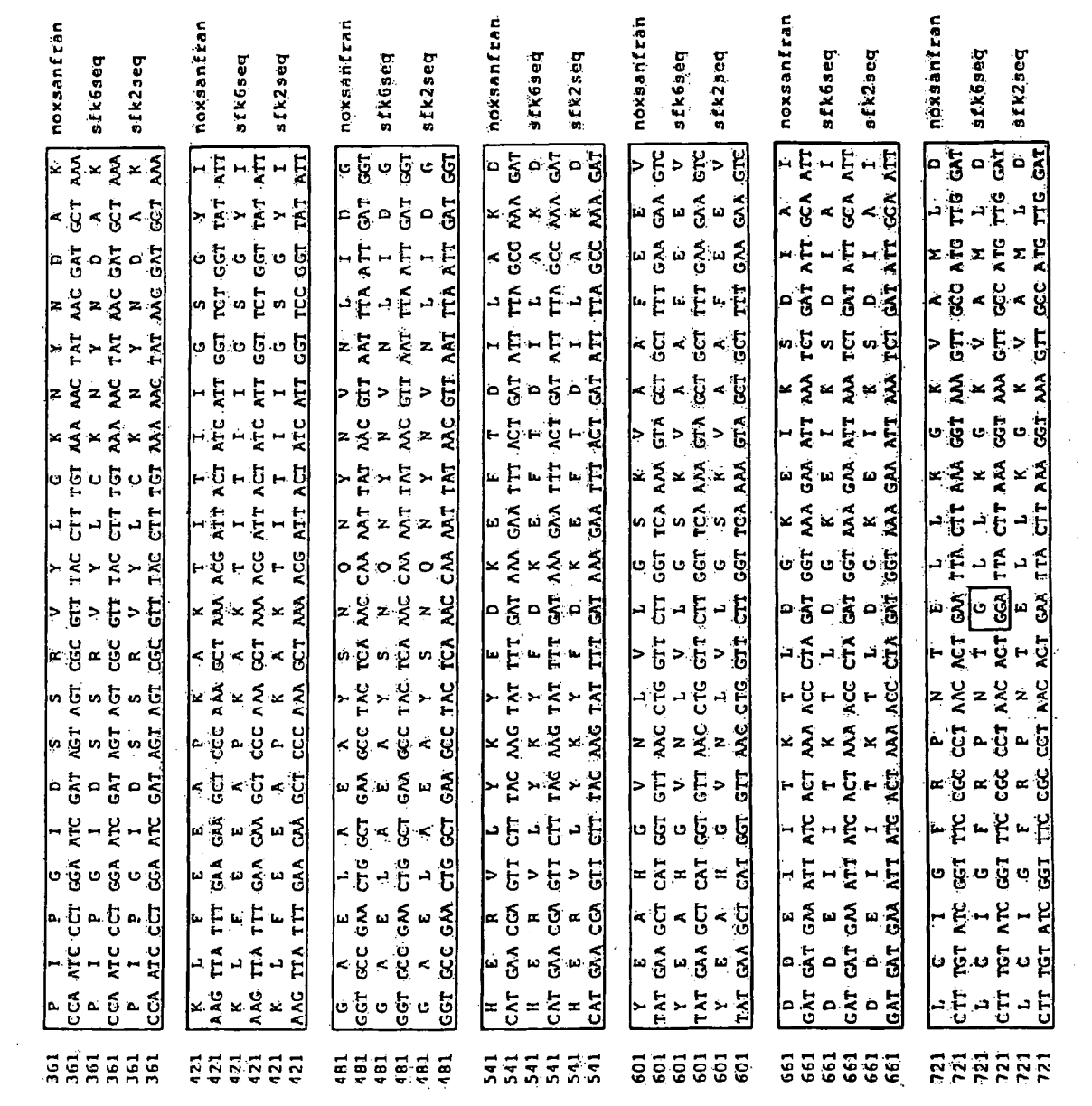
Figure 2F:
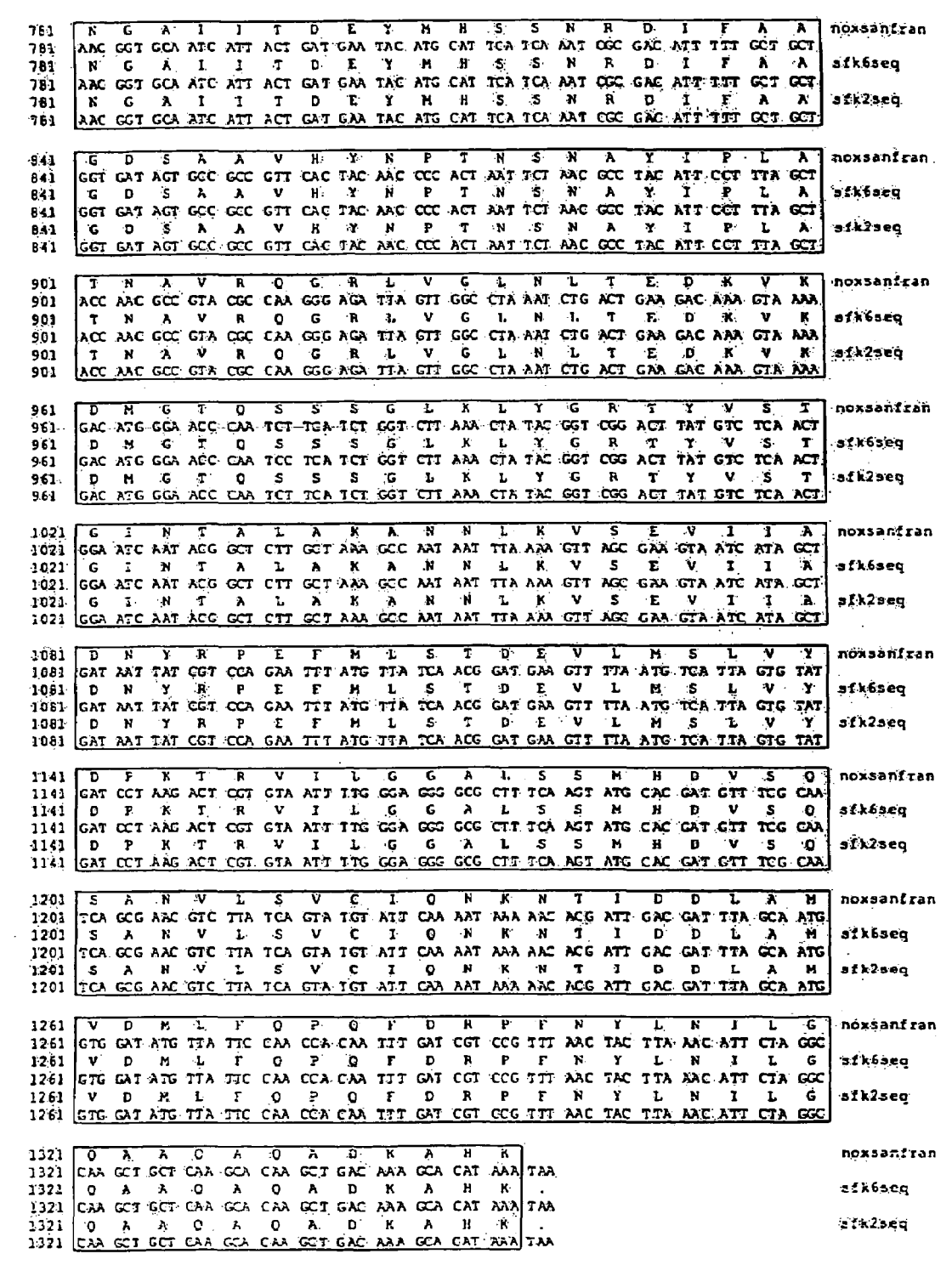

In FIG. 2A-2C, the complete nucleotide sequences of BNOX, BNOXK1 and BNOXK6 (SEQ ID NO.: 7, 9 and 11) as well as the respective deduced amino acid sequences (SEQ ID NO.: 8, 10 and 12) are shown. The nucleotide sequences are compared to the annotated sequence available in the data bank, BNOX. In FIG. 2D-2F, both nucleotide (SEQ ID NO.: 1, 3 and 5) and deduced amino acid sequences (SEQ ID NO.: 2, 4 and 6) of SFNOX, SFNOXK2 and SFNOXK6 (SEQ ID NO.: 1, 3 and 5) are shown and are similarly compared to the annotated nucleotide sequence in the data bank, SFNOX. The decoration box indicates an exact match to the annotated sequences.

Comparison of the amino acid sequences between SFNOX and BNOX revealed a rather modest sequence identity of 32%. The consensus sequences are the FAD-binding site motif GXT(H/S)AG in position 8–14 (counted from the BNOX N-terminus), the putative catalytic cysteine residue in position 42, and the NAD-binding site GXGYIG in positions 156–161. Alignment with the sequences of the NADH oxidases of *Enterococcus faecalis* [48] and *Streptococcus mutans* [50] demonstrated at most 34% identity between any two including the two novel proteins, except for 55% between SFNOX and the enzyme from *E. faecalis*.

The present invention also comprises nucleic acids that hybridize under stringent conditions with the single-stranded (ss) nucleic acids or their complementary ss nucleic acids of the present invention. Stringent conditions are well known to those skilled in the art; see Sambrook et al., (Molecular Cloning, A Laboratory Manual, Cold Spring Harbor Laboratory Press (1989), 1.101–1.104). Stringent conditions are established by conditions such as salt concentrations, temperature and amount of time for washing of the hybridized nucleic acids. For example, conditions include washing of hybridized nucleic acids in 0.1% SDS and 1.0× to 0.2×SSC, at temperatures from 50° C. to 68° C., for times of 0.5 to 1.0 hours.

The present invention also comprises protein and nucleic acid sequences that exhibit a homology (exclusive of natural degeneration) greater than 80%, preferably greater than 90%, 91%, 92%, 93% or 94%, more preferably greater than 95% or 96%, and most preferably greater than 97%, 98% or 99% with SEQ. ID. NO.: 1–16, provided that the enzymatic activity is retained or the purpose of the sequence is retained, e.g. coding for a protein having this specific enzymatic activity or a protein fragment having a particular binding capability or immunogenic capability. Homology is defined by the equation $H(\%)=[1-V/X]\times100$, where H is homology, X is the total number of nucleotide bases or amino acids of the comparison sequence, and V is the number of different nucleotide sequences or amino acids of the sequence of the comparison sequence. The term "nucleic acids coding for amino acid sequences" includes all nucleic acid sequences that could code for the amino acid sequences according to the degeneration of the genetic code. Additionally, nucleic acid sequences comprising modified, complexed or rare replacement nucleotides are comprised within the term nucleic acids. Nucleic acids comprise all types of nucleic acids, including single-stranded, double-stranded, nucleoproteins, sequences made with either deoxyribose or ribose (DNA or RNA) or mixtures thereof. Nucleic acids also comprise all corresponding interfering sequences, such as RNAi sequences, and antisense molecules.

In other embodiments, the present invention comprises primers for producing the gene sequences disclosed herein, for example, by amplification using methods known to those skilled in the art such as polymerase chain reaction. The primers include the sense and antisense primers coding for the corresponding amino acid sequences. Suitable primers may in principle be obtained by methods known to the person skilled in the art. The discovery of primers according to the invention is carried out by comparison with known DNA sequences or by translation of the visually detected amino acid sequences into the codon of the organism under consideration (e.g. for *Streptomyces*: Wright et al., Gene 1992, 113, 55–65). Common features in the amino acid sequence of proteins of so-called superfamilies are also of use for this purpose (Firestine et al., Chemistry & Biology 1996, 3, 779–783). Further information relating to the above may be found in "Oligonucleotide synthesis: a practical approach", edited by M. J. Gait, IRL Press Ltd, Oxford Washington D.C., 1984; PCR Protocols: A guide to methods and applications, edited by M. A. Innis, D. H. Gelfound, J. J. Sninsky and T. J. White. Academic Press, Inc., San Diego, 1990. The following primers are most preferred: Restriction sites used are underlined.

Primer Sequences:

sequences having at least all or a portion of SFNOX (SEQ. ID NO.: 1, 3 and 5) or BNOX (SEQ.ID NO.: 7, 9 and 11), or all or a portion of a combination of any of SEQ ID NO.: 1, 3, 5, 7, 9 and 11. Such constructs may also have other sequences such as antibiotic resistance, the same or different promoters for SFNOX or BNOX, and other sequences known to those skilled in the art.

Use of plasmids, vectors or constructs and different types of plasmids, vectors or constructs are well known in the art and the present invention contemplates inclusion of these uses and types with the sequences disclosed herein. Such art includes, but is not limited to, Sambrook, supra, or brochures from companies such as Novagen, Promega, New England Biolabs, Clontech or Gibco BRL. Well known plasmids include pBTac (Roche Biochemicals), pKK-223 (Stratagene) or pET (Novagen).

The compositions of the present invention also comprise combinations of all or a portion of SEQ ID NO.: 1, 3, 5, 7, 9 and 11 with other nucleic acid sequences to encode chimera proteins, or the nucleic acids of NOX combined with proteins or attached to solid supports such as beads. Such chimera proteins or other combinations may or may not retain the enzyme activity of SFNOX and/or BNOX. For example, a nucleic acid construct that codes for a chimera protein is constructed from SEQ. ID NO.: 1 and sequences for an antibody protein or binding fragment thereof. Such a chimera is used in antibody labeling experiments.

The present invention also comprises compositions comprising the NOX enzymes disclosed herein that include immobilization of the enzymes on heterogeneous substrates. For example, the enzymes may be immobilized or attached to other proteins, through methods such as chemical linking of the proteins, attached to inert substrates such as microtiter plates, chromatography materials, balls, beads or other substances. The invention contemplates the use of such immobilized enzymes in methods of synthesis, measurement, analysis or other methods wherein enzymes are used. These methods for immobilizing and using such immobilized enzymes are known to those skilled in the art.

The compositions of the present invention also comprise antibodies and other specific binding partners, such as substrates, of SFNOX and BNOX, and immunogenic epitopes thereof. Such antibodies may be polyclonal or monoclonal, and include fragments such as Fab, FC, heavy chains, light chains, constant, variable, or hypervariable fragments or regions, and any type of antibody include but are not limited to IgM, IgG, IgA, IgD, and IgE.

The compositions of the present invention also contemplate the inclusion of any cofactors, metals or other com-

```
N- and C-terminal primers for L. sanfranciscensis
SEQ ID NO.:13 5' gcg c gaattc atg aaa gtt att  sanfranseco,   Tm 67.2° C.
              gta gta ggt tgt act 3'

SEQ ID NO.:14 5' gcg c aagctt tta ttt atg tgc  Sanfranashind, Tm 62.8° C.
              ttt gtc agc ttg tgc 3'

N- and C-terminal primers for B. burgdorferi
SEQ ID NO.:15 5' gcg c gg atc c at gat gaa aat Borrnoxs,     Tm 69.5° C.
              aat aat tat tgg ggg 3'

SEQ ID NO.:16 5' gcg c aa gct t ct att tgg cag Borrnoxas,    Tm 70.6° C.
              cat tgc cag caa tat t 3'
```

The compositions of the present invention comprise vectors, plasmids or constructs comprising one or more of the NOX of the present invention. The terms vectors, plasmids or constructs are used interchangeably to mean nucleic acid pounds or molecules necessary for activity or stability of the NOX of the present invention.

The present invention also comprises microorganisms comprising the nucleic acids disclosed herein, particularly SEQ ID NO.: 1, 3, 5, 7, 9 and 11. The microorganisms in which the nucleic acids are cloned are useful for propagation and production of a sufficient amount of the recombinant enzyme or enzymes. The methods for cloning, propagating and producing recombinant proteins in cellular systems are well known in the art. Examples of such microorganisms include, but are not limited to, prokaryotes or eucaryotes, such as *Pseudomonas, Streptomyces, Arthrobacter, Bacillus, Staphylococcus, Enterococcus*, especially *E. coli, Candida, Hansenula, Pichia* and baculovirus systems. Plasmids, vectors or constructs containing the gene constructs of SEQ.ID.NO.: 1 and/or 3 are cloned into host organisms, such as those above.

The nucleic acids disclosed herein that code for the NAD(P)H oxidase (NOX) as described herein, are preferably suitable for the production of whole-cell catalysts. The invention provides a whole-cell catalyst containing a cloned gene for a dehydrogenase and a cloned gene for an NAD(P)H oxidase. The whole-cell catalyst according to the invention should contain an NAD(P)H oxidase (NOX), preferably a bacterial oxidase that can regenerate NAD+ and NADP+. More preferably, the NAD(P)H oxidase is one or more of the NOX disclosed herein and coded for by SEQ ID NO.: 1, 3, 5, 7, 9 and 11. The production of such an organism is known to the person skilled in the art (PCT/EP00/08473; PCT/US00/08159).

The advantage of such an organism is the simultaneous expression of at least two different enzymes, and then only the whole cell catalyst recombinant organism is used for the enzymatic reaction. In order to match the expression of the enzymes with respect to their reaction rates, the coding nucleic acids may be carried on various plasmids having different copy numbers and/or promoters of different strengths may be used. In one embodiment, the enzymes are encoded on plasmids with similar copy numbers in a host cell; and/or under the control of promoters of similar strength. With enzyme systems matched in this way there is advantageously no accumulation of a possible inhibiting intermediate compound(s), and the reaction under consideration may proceed at an optimal overall rate. This is described in PCT/EP00/08473; and Gellissen et al., Appl. Microbiol. Biotechnol. 1996, 46, 46–54.

Methods of the present invention comprise methods for growing and isolating NOX proteins, particularly bacterial oxidases capable of regenerating NAD+ and NADP+. One embodiment comprises growing host organisms, *Lactobacillus sanfranciscensis* or *Borrelia burgdorferi*, and isolating the NOX enzyme by methods known to those skilled in the art, such as ammonium or acid precipitation, or chromatography, and other protein purification techniques. An embodiment comprises growing bacteria and isolating bacterial NOX that are capable of regenerating NAD+ and NADP+. Another embodiment comprises growing and isolating recombinant NOX proteins.

The nucleic acids according to the invention can be used for the production of recombinant (rec) NAD(P)H oxidase, which is included herein in the term NOX. Recombinant techniques known in the art can be used to produce the enzymes described herein in an amount sufficient for an industrial process from host cells carrying the nucleic acids encoding the enzyme. The production of the rec-enzymes according to the invention is carried out by genetic engineering processes as described in, for example, Sambrook supra, Balbas P & Bolivar F. 1990; Design and construction of expression plasmid vectors in *E. coli*, Methods Enzymology 185, 14–37; Vectors: A Survey of Molecular Cloning Vectors and Their Uses. R. L. Rodriguez & D. T. Denhardt, Eds: 205–225). With regard to the general procedure (PCR and fusion PCR, inverse PCR, cloning, expression etc.), reference may be made to the following literature and the references cited therein: Riley J, Butler R, Finniear R, Jenner D, Powell S, Anand R, Smith J C, Markham A F (1990). A novel, rapid method for the isolation of terminal sequences from yeast artificial chromosome (YAC) clones. Nucl Acids Res. 18, 8186; Triglia T, Peterson M G, Kemp D J (1988). A procedure for in vitro amplification of DNA segments that lie outside the boundaries of known sequences. Nucleic Acids Res. 16, 8186; Sambrook J, Fritsch E F, Maniatis T (1989). Molecular Cloning. Cold Spring Harbour Laboratory Press; Vectors: A Survey of Molecular Cloning Vectors and Their Uses. R. L. Rodriguez & D. T. Denhardt, II.

The bacterial oxidase enzymes described herein may be used in the free form as homogeneously purified compounds, or as enzymes produced by recombinant technology. Furthermore the enzymes may also be employed as a constituent of an intact host organism or in conjunction with the macerated cell mass of the host organism purified to an arbitrarily high degree. It is also possible to use the enzymes in immobilized form (Bhavender P. Sharma, Lorraine F. Bailey and Ralph A. Messing, "Immobilisierte Biomaterialien—Techniken und Anwendungen", Angew. Chem. 1982, 94, 836–852). The immobilization is preferably carried out by lyophilisation (Dordick et al. J. Am. Chem. Soc. 194, 116, 5009–5010; Okahata et al. Tetrahedron Lett. 1997, 38, 1971–1974; Adlercreutz et al. Biocatalysis 1992, 6, 291–305). It is most particularly preferred to carry out the lyophilisation in the presence of surfactants such as aerosol OT, polyvinylpyrrolidone, polyethylene glycol (PEG) or Brij 52 (diethyleneglycolmonocetyl ether) (Goto et al. Biotechnol. Techniques 1997, 11, 375–378). The use as CLECs is also possible (St Clair et al. Angew Chem Int Ed Engl 2000 January, 39(2), 380–383).

The present invention comprises methods for isolating NOX. One embodiment comprises methods of isolation comprising the purification table shown in Table 2. The procedure results in a strong single prominent band at 50 kDa in the protein gel analysis, is scalable, and results in high yields. Acid precipitation as the first resolution eliminates buffer/salt exchanges and leaves the final protein preparation in stabilizing levels of ammonium sulfate. [63]

TABLE 2

Purification table resulting in scalability and high yield

| Step | Vol (ml) | Activity (U/ml) | Protein (mg/ml) | Specific Activity (U/mg) | Yield (%) | Purification factor | Σ U |
| --- | --- | --- | --- | --- | --- | --- | --- |
| Lysate (pH 5.0) | 10.2 | 424.4 | 14.3 | 29.7 | 100.0 | 1.0 | 4329.3 |
| Dialysis (60 kDa MWCO)/Acid Precip pH 4.8 | 10.5 | 277.4 | 5.4 | 51.8 | 67.3 | 1.7 | 2912.7 |

TABLE 2-continued

Purification table resulting in scalability and high yield

| Step | Vol (ml) | Activity (U/ml) | Protein (mg/ml) | Specific Activity (U/mg) | Yield (%) | Purification factor | Σ U |
|---|---|---|---|---|---|---|---|
| Mono-Q | 1.0 | 476.7 | 5.1 | 93.1 | 57.8* | 3.1 | 476.7 |
| 45% ammonium sulfate dialysis | 0.35 | 1114.1 | 8.4 | 132.6 | 47.3* | 4.5 | 390.0 |

*estimated theoretical yield for entire preparation.

Another embodiment comprises the steps in a different sequence (lysate—45% ammonium sulfate precipitation—acid precipitation (pH 5, 30° C.)—Q-Sepharose FF) which, in one experiment, resulted in the same specific activity to within 0.5% The yield of this alternative purification sequence was 33.6%.

Another embodiment for isolation of NOX comprises displacement chromatography after dialysis and acid precipitation, (like that described above). The displacer was naphthalene-1,3,6-trisulfonic acid, which provides for a method of isolation that can be scaled-up for industrial use. As the results in Table 3 reveal, purity in excess of 95% at 26% yield was achieved with a specific activity of 221 U/mg protein. The highly pure and active fractions can then be pooled and stored in 45% ammonium sulfate solution at 4° C. to preserve the enzyme's stability. Displacement chromatography generally improves at higher loadings [52] and the novel displacer, naphthalene-1,3,6-trisulfonic acid, is an inexpensive reagent in contrast to many other reported displacers [53].

A method for isolating NOX comprises, a) precipitating with an acid solution of pH 4.5 to 6.0, a bacterial cellular lysate; and b) isolating NOX proteins from the solution of b) after precipitation occurs. In general, precipitation in an acid solution inactivates most proteins in the cellular lysate, but not the NOX proteins. Precipitation begins as soon as the lysate is placed in the acidic solution. The range of pH of the acidic solution is from approximately 4.5 to approximately 6.0, preferably pH 4.5 to 5.5, and more preferably pH 5.0. The time for precipitation can be in a range from minutes to hours, including 10 minutes to 24 hours. Precipitating activity can occur at the same time as other activities such as salt removal in dialysis systems. The precipitated material contains inactivated proteins and the resulting solution contains the NOX proteins. Isolation of the NOX protein from the solution can be accomplished any number of different methods known to those skilled in the art. For example, NOX may be isolated by centrifugation of the solution, or centrifugation followed by other techniques such as displacement chromatography, sizing chromatography, affinity chromatography, molecular sieving, cofactor binding, or other techniques that isolate the NOX from the solution. These isolation methods are well known in the art and all applicable methods are contemplated as part of the present invention.

TABLE 3

Purification of NADH oxidase from *L. sanfranciscensis*

| Step | Activity (U/ml) | Protein (mg/ml) | Specific Activity (U/mg) | Yield (%) | Σmg | ΣU | Purification Factor |
|---|---|---|---|---|---|---|---|
| Lysate (pH 5.0) | 768.6 | 21.7 | 35.4 | — | 661.9 | 23,443 | 1.0 |
| Dialysis (60 kDa MWCO membrane)/Acid precip pH 5.0 | 582.2 | 9.0 | 65.0 | 79.5 | 286.7 | 18,629 | 1.8 |
| Displacement Source 30Q | 136.2 | 0.6 | 220.9 | 26.2 | 27.75 | 6,131 | 6.2 |

The ability of bacterial oxidases, such as SFNOX, to oxidize both cofactors, NADPH and NADH, renders such enzymes as an extremely useful catalyst for coupled enzymatically-catalyzed oxidations. To demonstrate the regeneration to either NAD$^+$ or NADP$^+$ by NAD(P)H oxidase SFNOX, the enzyme was combined with (R)-ADH from *L. brevis* to produce acetophenone and (S)-phenylethanol from racemic (RS)-phenylethanol. (R)-ADH from *L. brevis* [54] was picked for the following advantages: i) (R)-1-phenylethanol is a very good substrate, on a par with the best substrates of the enzyme, ii) whereas the wildtype is mainly NADPH-dependent, the G37D mutant strongly prefers NADH over NADPH [55], albeit at reduced specific activity; iii) lastly, (R)-ADH from *L. brevis* has been explored extensively for the enzymatic generation of several pharmaceutically interesting chiral alcohols [56–59,25].

In experiments described herein, after 12 h, nearly complete conversion (maximally 50% of racemic phenylethanol) was achieved in all but the case of the G37D mutant ADH with NAD$^+$. The very high $K_M$-value of the mutant ADH for NAD$^+$ in comparison with the wildtype for NADP$^+$ is a possible explanation for the lower rate (less than $v_{max}$) and thus lower conversion after 12 hr. The number of turnovers ([acetophenone]/[cofactor]) of up to more than 100 clearly demonstrates catalysis by both enzymes involved.

Methods of the present invention comprise coupled enzymatic reactions wherein bacterial oxidases, including but not limited to, SFNOX, provide both NAD+ and NADP+ to one or more enzymes. An embodiment of methods of using bacterial oxidases, including but not limited to, SFNOX, comprises use in analytical determinations such as in measuring the total amount of reducing equivalents from NAD+ and NADP+ in a cell by measuring the reactions of bacterial oxidases, including but not limited to, SFNOX, and NAD/NADP. Such measurements can be important to estimate the ability of a cell to achieve reduction of a given substrate. The reducing equivalent amount can provide an identifying characteristic of a cell or cell types. For example, such measurement could differentiate between normal, precancerous and cancerous cells, or between normal cells and cells entering apoptosis, or between different cellular types. Another embodiment comprises using bacterial oxidases, including but not limited to, SFNOX as a standard in NAD/NADP experiments.

One embodiment of the present invention comprises methods and compositions comprising recombinant NOX and nucleic acids encoding recombinant NOX that have been altered from genomic or recombinant sequences by mutation. One method comprises the production of improved rec-NOX and rec-NOX obtained thereby or nucleic acids coding therefor, starting from the nucleic acids according to the invention coding for an NAD(P)H oxidase (NOX), such method comprising, a) mutating nucleic acids,
b) cloning the nucleic acids obtained from a) in a vector, plasmid or construct; and
c) isolating the proteins expressed.

This process may be executed once or any desired number of times in succession. Preferably, the mutated nucleic acids code for proteins having a property different from the proteins encoded by the nucleic acids disclosed herein, more preferably, the mutated rec-NOX have enhanced desired properties such as faster cofactor turnover or more stability in reaction conditions.

Embodiments of mutations of the present invention comprise individual amino acid substitutions, and its concomitant changes in the nucleic acid sequence. Preferred embodiments comprise mutated sequences comprising at least a substitution at position 42 of SFNOX. For example, mutations of position of 42 of C to S, C to M, C to A and C to F. (for example, SEQ ID NO. 17–20), and the nucleic acids, including degenerate bases, that encode such amino acids. Embodiments of the present invention comprise other amino acid substitutions at this site, and such mutations include substitution or unnatural amino acids, such as homoserine, or unnatural nucleic acids.

```
SEQ ID NO. 17
MKVIVVGCTHAGTFAVKQTI

ADHPDADVTAYEMNDNISFL

SSGIALYLGKEIKNNDPRGLFYSSPEELSNLGANVQMRHQ

VTNVDPETKTIKVKDLITNEEKTEAYDKLIMTTGSKPTVPPIPGIDSSRVYLCKNYNDAKKLFEEAPK

AKTITIIGSGYI

GAELAEAYSNQNYNVNLIDGHERVLYKYFDKEFTDILAKDYEAHGVNLVLGSKVAAFEEVDDEIITKT

LDGKEIKSDIAI

LCIGFRPNTELLKGKVAMLDNGAIITDEYMHSSNRDIFAAGDSAAVHYNPTNSNAYIPLATNAVRQGR

LVGLNLTEDKVK

DMGTQSSSGLKLYGRTYVSTGINTALAKANNLKVSEVIIADNYRPEFMLSTDEVLMSLVYDPKTRVIL

GGALSSMHDVSQ

SANVLSVCIQNKNTIDDLAMVDMLFQPQFDRPFNYLNILGQAAQAQADKAHK

SEQ ID NO.18
MKVIVVGCTHAGTFAVKQTI

ADHPDADVTAYEMNDNISFL

SMGIALYLGKEIKNNDPRGLFYSSPEELSNLGANVQMRHQ

VTNVDPETKTIKVKDLITNEEKTEAYDKLIMTTGSKPTVPPIPGIDSSRVYLCKNYNDAKKLFEEAPK

AKTITIIGSGYI

GAELAEAYSNQNYNVNLIDGHERVLYKYFDKEFTDILAKDYEAHGVNLVLGSKVAAFEEVDDEIITKT

LDGKEIKSDIAI

LCIGFRPNTELLKGKVAMLDNGAIITDEYMHSSNRDIFAAGDSAAVHYNPTNSNAYIPLATNAVRQGR

LVGLNLTEDKVK

DMGTQSSSGLKLYGRTYVSTGINTALAKANNLKVSEVIIADNYRPEFMLSTDEVLMSLVYDPKTRVILGGALSSM

HDVSQ

SANVLSVCIQNKNTIDDLAMVDMLFQPQFDRPFNYLNILGQAAQAQADKAHK

SEQ ID NO. 19
```

-continued

MKVIVVGCTHAGTFAVKQTI

ADHPDADVTAYEMNDNISFL

SAGIALYLGKEIKNNDPRGLFYSSPEELSNLGANVQMRHQ

VTNVDPETKTIKVKDLITNEEKTEAYDKLIMTTGSKPTVPPIPGIDSSRVYLCKNYNDAKKLFEEAPK

AKTITIIGSGYI

GAELAEAYSNQNYNVNLIDGHERVLYKYFDKEFTDILAKDYEAHGVNLVLGSKVAAFEEVDDEIITKT

LDGKEIKSDIAI

LCIGFRPNTELLKGKVAMLDNGAIITDEYMHSSNRDIFAAGDSAAVHYNPTNSNAYIPLATNAVRQGR

LVGLNLTEDKVK

DMGTQSSSGLKLYGRTYVSTGINTALAKANNLKVSEVIIADNYRPEFMLSTDEVLMSLVYDPKTRVIL

GGALSSMHDVSQ

SANVLSVCIQNKNTIDDLAMVDMLFQPQFDRPFNYLNILGQAAQAQADKAHK

SEQ ID NO. 20
MKVIVVGCTHAGTFAVKQTI

ADHPDADVTAYEMNDNISFL

SFGIALYLGKEIKNNDPRGLFYSSPEELSNLGANVQMRHQ

VTNVDPETKTIKVKDLITNEEKTEAYDKLIMTTGSKPTVPPIPGIDSSRVYLCKNYNDAKKLFEEAPK

AKTITIIGSGYI

GAELAEAYSNQNYNVNLIDGHERVLYKYFDKEFTDILAKDYEAHGVNLVLGSKVAAFEEVDDEIITKT

LDGKEIKSDIAI

LCIGFRPNTELLKGKVAMLDNGAIITDEYMHSSNRDIFAAGDSAAVHYNPTNSNAYIPLATNAVRQGR

LVGLNLTEDKVK

DMGTQSSSGLKLYGRTYVSTGINTALAKANNLKVSEVIIADNYRPEFMLSTDEVLMSLVYDPKTRVIL

GGALSSMHDVSQ

SANVLSVCIQNKNTIDDLAMVDMLFQPQFDRPFNYLNILGQAAQAQADKAHK

Embodiments of mutations of the sequences and resulting proteins disclosed herein also include, but are not limited to, substitutions at other sites, insertions, deletions, additions and reversions, changes due to recombination of NOX sequences or sequences comprising NOX sequences with other nucleic acids, and other mutations known to those skilled in the art.

The procedure for mutating the enzymes of the present invention by mutagenesis methods has long been known to the person skilled in the art. As mutagenesis methods there may be used all methods for this purpose available to the person skilled in the art. In particular these include saturation mutagenesis, random mutagenesis, shuffling methods as well as site-directed mutagenesis (Eigen M. and Gardinger W. (1984) Evolutionary molecular engineering based on RNA replication. Pure & Appl. Chem. 56(8), 967–978; Chen & Arnold (1991) Enzyme engineering for nonaqueous solvents: random mutagenesis to enhance activity of subtilisin E in polar organic media. Bio/Technology 9, 1073–1077; Horwitz, M. and L. Loeb (1986) "Promoters Selected From Random DNA-Sequences" Proceedings Of The National Academy Of Sciences Of The United States Of America 83(19): 7405–7409; Dube, D. and L. Loeb (1989) "Mutants Generated By The Insertion Of Random Oligonucleotides Into The Active-Site Of The Beta-Lactamase Gene" Biochemistry 28(14): 5703–5707; Stemmer P C (1994). Rapid evolution of a protein in vitro by DNA shuffling. Nature. 370; 389–391 and Stemmer P C (1994) DNA shuffling by random fragmentation and reassembly: In vitro recombination for molecular evolution. Proc Natl Acad Sci USA. 91; 10747–10751).

The new nucleic acid sequences that are obtained are cloned according to the methods known to those skilled in the art in a host organism and the expressed enzymes are detected and then isolated using suitable screening methods (Roberts J., Stella V. J. and Decedue C. J. (1985) A colorimetric assay of pancreatic lipase: rapid detection of lipase and colipase separated by gel filtration. Lipids 20(1): 42–45; Pratt R. F., Faraci W. S. and Govardhan C. P. (1985) A direct spectrophotometric assay for D-alanine carboxypeptidases and for the esterase activity of beta-lactamases. Anal. Biochem. 144(1): 204–206; Bruckner, H., R. Wittner, and H. Godel (1991) Fully automated high-performance liquid chromatographic separation of DL-amino acids derivatized with o-Phthaldialdehyde together with N-isopropyl-cysteine. Application to food samples).

The present invention also comprises using NAD(P)H oxidase (NOX), bacterial oxidases with NAD+ and NADP+ regeneration activity, SFNOX, BNOX and the proteins encoded by SEQ ID NOs 1–12 and 17–20 and any mutations thereof, for the production of chiral enantiomer-enriched organic compounds such as, for example, alcohols or amino acids, in coupled enzymatic reactions. Such compounds are useful in pharmaceutical preparations, in agricultural uses, for food, and crop protection industries as well as building blocks for novel compounds not accessible through fermentation and for asymmetric synthesis templates. Embodiments of such methods comprise a method of organic synthesis, comprising, reacting a bacterial NAD(P)H oxidase with NADH or NADPH in a coupled enzyme reaction, and isolating the products of the reaction. Such methods of use include the synthesis of enantiomerically-enriched chiral compounds, synthesis of chiral compounds, synthesis of physiologically effective compounds that are used in treatments of humans, animals, plants, insects, microbiological organisms, and other eukaryotes and prokaryotes. For example, compounds are produced that are effective in treatment of humans and other animals for hypertension, diabetes, cardiovascular disease, cancer, and conditions involving the brain, eyes, heart, lungs, liver, immune system, urinary organs, reproductive organs, integumentary system, nervous system and other conditions where pharmaceutical agents are effective. Compositions that are effective in such methods include compositions comprising at least a bacterial oxidase that regenerates NADP+ or NAD+, and preferably comprise at least a bacterial oxidase that regenerates NADP+ and NAD+.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

The present application claims priority to U.S. Provisional Patent Application 60/399, 850, the entire contents of which are incorporated herein by reference. Additionally, the references cited herein are each hereby incorporated by reference in its entirety.

Having generally described this invention, a further understanding can be obtained by reference to certain specific examples. The examples are not intended to limit, and should not be interpreted as limiting, the scope of what the inventors regard as their invention.

EXAMPLES

Example 1

Bacterial Strains, Media and Growth Conditions

The genomic DNA from *Borrelia burgdorferi* (ATCC 35210) and the strain *Lactobacillus sanfranciscensis* (ATCC 27651) were obtained from ATCC and grown in MRS medium (Gibco) at pH 6.5 under facultatively anaerobic conditions at 30° C. in quiescent culture. For expression of wild-type NADH oxidase, the *L. sanfranciscensis* strain was grown in the same medium, but under aeration with 120 rpm in an Infors shaker at 30° C.

Host strains of *E. coli* were grown in Luria-Bertani medium at pH 7.5 and 37° C., for cloning purposes or routine growth and plasmid production the host strain XL1 blue (Stratagene, La Jolla) was used. For expression purposes an HB101 strain (Stratagene, La Jolla) or M15 strain including the pREP4 plasmid (Qiagen, Hilden) was employed. These *E. coli* strains were grown at 30° C. under agitation for optimized expression levels. Ampicillin was added to the medium at a final concentration of 100 µg/ml to maintain selection pressure. To the M15 strain, 25 µg/ml kanamycin was added to maintain the additional helper plasmid.

Plasmids used: for cloning and sequencing, target genes were cloned into pBluescript (Stratagene, La Jolla); for expression either the pkk223-3 (Amersham) or pBTac2 (Roche) were chosen.

Example 2

Manipulation and Amplification of DNA

The nox DNA sequences were identified using a search of the NCBI Genebank (Accession files AB035801 for SFNOX and NC_001318 for BNOX). The corresponding specific 5' and 3' primers were synthesized at MWG Biotech (High Point, N.C.). Primer optimization was performed using a primer design program (webbased design, http:/genome-www2.stanford.edu/cgi-bin/SGD/web-primer). The nox genes from *L. sanfranciscensis* and *B. burgdorferi* were amplified using PCR and the gene-specific primers. Restriction sites used are underlined.

Primer Sequences:

```
N- and C-terminal primers for L. sanfranciscensis
5' gcg c gaattc atg aaa    sanfranseco    Tₘ 67.2° C.
gtt att gta gta ggt tgt
act 3'

5' gcg c aagctt tta ttt    sanfranashind  Tₘ 62.8° C.
atg tgc ttt gtc agc ttg
tgc 3'

N- and C-terminal primers for B. burgdorferi
5' gcg c gg atc c at gat    borrnoxs      Tₘ 69.5° C.
gaa aat aat aat tat tgg
ggg 3'

5' gcg c aa gct t ct att    borrnoxas     Tₘ 70.6° C.
tgg cag cat tgc cag caa
tat t 3'
```

Amplification of the target DNA was performed using the protocol from the failsafe PCR kit (Epicentre, Madison). Twelve reactions using 12 different buffers were set up and tested for optimal conditions. Setting up the PCR reactions involved final DNA concentration of 100 ng (*L. sanfranciscensis*) and 3.4 ng (*B. burgdorferi*), 200 µM of each dNTP, 10 µM of each primer and 1 U of Taq polymerase (Epicentre, Madison) in a final volume of 25 µl. To each of these reactions, 25 µl of each of the twelve doubly concentrated reaction buffer was added. DNA was amplified successfully for 30 cycles in an Eppendorf Gradient Thermocycler (Eppendorf, Hamburg) using the following conditions: each cycle involved a denaturing step at 30 sec 94° C., an annealing step at 30 sec 60° C. or 68° C., and an extension step at 2 min 72° C. Of the final reaction mixture, 50 µl was analyzed on 1% agarose gels stained with 0.05% ethidium bromide. Prior to any further use, these PCR products were gel purified using the gel extraction kit (Qiagen, Hilden).

Amplification in PCR succeeded using the PCR failsafe kit (Epicentre, Madison) to yield products of the predicted size of 1335 bp for bnox and 1356 bp for sfnox in several of the 12 buffers provided with the kit. The primers were designed to contain convenient restriction sites (EcoR1 and HindIII for SFNOX and BamH1+HindIII as well for BNOX) at both ends to facilitate the following cloning step.

DNA electrophoresis on a 1% agarose gel demonstrates amplification of the nox genes under different PCR-buffer conditions. As expected, single bands in each lane were found at around the 1300 bp band for BNOX and between 1300 and 1400 bp for the SFNOX. Depending on buffer conditions, strong or weak amplification was observed with both NOX genes. Each one of the strongest bands was cut out of the 1% agarose gel and purified using the gel purification kit (Qiagen, Hilden).

Both gene products as well as the pbluescript vector (Stratagene) were restricted with the following enzymes: BNOX with BamH1 and HindIII and SFNOX with EcoR1 and HindIII. Following restriction, the genes and the vector were purified through gel electrophoresis and subsequent elution (gel purification kit, Qiagen, Hilden). Both genes were separately cloned into the pbluescript vector (Stratagene, La Jolla) and transformed into the *E. coli* XL1blue strain (Stratagene, La Jolla). Positive clones were screened using colony PCR and restriction analysis.

Nucleotide data corresponding to the 1335 bp of BNOX and 1356 bp for SFNOX, starting with ATG, were obtained through cycle sequencing using an ABI prism sequencer. Nucleotide sequence and deduced open reading frames are shown in FIG. 2. Sequencing templates were the pbluescript-constructs. The open reading frame for both noxes is capable of encoding a protein with a molecular mass of 48.8 kD for SFNOX and 48 kD for BNOX. SDS-PAGE of the proteins derived from the expressed genes exhibited a prominent band at around 45–50 kD. The GC content of the genes coding for BNOX and SFNOX are very low, 32% and 37%, respectively, consistent with the range reported by Ross and Claiborne (1992).[48]

Example 3

Cloning

Nox-specific DNA from *L. sanfranciscensis* was ligated into pBluescript (Stratagene, La Jolla) using EcoR1 (5') and HindIII (3') restriction sites and accordingly, nox from *B. burgdorferi* with BamH1(5') and HindIII (3') restriction sites. For all necessary ligations the Rapid Ligation kit protocol (Roche, Penzberg) was followed. The same pmol amounts of DNA were ligated, concentrations were calculated accordingly using the spectrophotometrically determined 260/280 nm ratio. Wildtype or mutant expression clones were constructed with the same restriction sites of Nox-*L-sanfranciscensis* (Lsfnox) into pkk223-3 (Amersham, Piscataway, N.J.) and nox-B-burgdorferi (Bnox) into pBtac2 (Roche, Penzberg). Positive clones were tested either through colony PCR or restriction digest after plasmid preparation using the Miniprep Spin kit (Qiagen, Hilden).

Example 4

Colony PCR

Colonies of the transformation plate were picked and first transferred onto a master plate, then suspended into 50 µl of lysis buffer containing Triton-X-100 (20 mM Tris pH 8.5+5 mM EDTA+1% Triton X-100). After denaturing at 95° C. for 15 min, the solution was vortexed for 10 seconds and then 5 µl of the extract was tested in PCR (total volume 50 µl) using the gene specific primers.

Example 5

Plasmid Preparation 5 ml $LB_{amp}$ was inoculated with a colony and grown overnight at 37° C. Cells were harvested by centrifugation (10000 rpm, 5 min, Eppendorf centrifuge, Hamburg) and plasmid DNA was isolated following the manufacturer's protocol (Miniprep Spin Kit, Qiagen, Hilden). Plasmid DNA was eluted into 50 µl water and 5 µl were digested with the corresponding restriction enzymes at the sites used for cloning and ligating.

Example 6

Sequencing

20 µg of plasmid DNA (using the pBluescript vector) was sent off for sequencing using the same primers as for amplification in PCR. The templates were labeled with Applied Biosystems' "BigDye Terminator v3.0 Cycle Sequencing Ready Reaction" Kit for 25 cycles. Excess dye terminator molecules were removed with Qiagen Dye-Ex Spin Columns (Qiagen, Hilden). The samples were analyzed on the Applied Biosystems 3100 Genetic Analyzer (Perkin-Elmer-AB, Boston).

Sequence analysis of both SFNOX and BNOX genes revealed differences when compared to the annotated nucleotide sequences derived from the NCBI databank (accession files AB035801 for SFNOX and NC_001318 for BNOX). Both fully sequenced SFNOX clones, SFNOXK2 and SFNOXK6, featured an amino acid change from alanine to valine at position 30 (A30V). SFNOXK6 showed an additional change from lysine to arginine at position 102 (K102R). Both constructs, when overexpressed, showed comparable activity. Though not wishing to be bound by any particular theory, it is believed that position 102 does not diminish enzyme activity and that SFNOXK2 with its sequence difference in position 30 shows the correct sequence for a NADH oxidase from *L. sanfranciscensis* rather than the sequence annotated in the databases.

Example 7

Expression of the nox Genes

The pbluescript constructs were used to cut out the desired gene and subclone it into the expression vector pkk223-3 (Amersham) or pBTac2 (Roche), respectively. With this method no additional PCR was required and risk for additional PCR errors was avoided. Subcloning was successful using the Rapid DNA ligation kit (Roche) and the ligation was transformed into competent HB101 (Stratagene, La Jolla) or M15 *E. coli* strains (Qiagen, Hilden). Colonies formed were tested for successful incorporation through colony PCR.

Two successful clones of each construct were expressed at 37° C. and harvested after 4 h of IPTG induction (SFNOXK2 and SFNOXK6 for *L. sanfranciscensis* and BNOXK1 and BNOXK6 for *B. burgdorferi*). Cell density was equalized to an $OD_{600}$ of 5.0 and then ultrasonicated in 200 µl of 100 mM TEA pH 7.5 buffer. Equal amounts of each fraction, soluble and unsoluble, induced and uninduced, were loaded onto a 12.5% SDS-PAGE. At 37° C., the SFNOXK6 clone demonstrates a high level of overexpression in the insoluble fraction, possibly owing to the additional mutation. BNOXK1 does not show an overexpression, and the expression level of BNOXK6 is slightly lower than that of SFNOXK2. In the case of SFNOXK2, the addition of helper plasmid pREP4 resulted in less uninduced expression when compared to the same clone without the helper plasmid.

Heterologous expression of the nox genes in *E. coli* was performed as follows: 5 ml starter $LB_{amp}$ cultures were inoculated with aliquots from frozen stock cultures containing either bnox-pBTac2 or sfnox-pkk223-3 and grown overnight at 37° C. These starter cultures were used to inoculate 200 ml cultures (1% v/v) or 1 L cultures (1% v/v), which were vigorously aerated until $A_{600}$ reached 0.5–0.6, at which point the cultures were induced with 1 mM IPTG (final concentration) and protein expression was performed for 4 h. Cells were harvested and pellets frozen away at −20° C. or used directly for enzyme activity assays.

For SDS-PAGE, 5 ml cultures were grown up to $A_{600}$ of 0.5 and then induced with 1 mM IPTG for 4 h. Cells were harvested, resuspended in 200 µl TE50/50 (50 mM Tris, 50 mM EDTA pH 8.0), and sonicated for 2×15 sec with ice cooling. Supernatant (representing the soluble fraction) was separated after centrifugation and the insoluble fraction was resuspended in 200 µl TE 50/50 and shortly sonicated (5 sec) to dissolve the pellet. 10% SDS sample buffer was added (10% Glycerol, 2% SDS, 0.063 M Tris/HCl pH 6.8, 0.1% Bromphenolblue+either 10% β-Mercaptoethanol or 75 mM DTT) and 30 µl analyzed on a 12.5% SDS-PAGE, stained with Coomassie blue (Pierce gel code staining solution, Pierce, Rockford, Ill.). Standard proteins used for molecular mass determination were obtained from New England Biolabs (Beverly, Mass.; broad range molecular weight markers, prestained).

Protein Gel Analysis

Prior to SDS-PAGE, protein samples were diluted to 2 mg/mL concentration in deionized water if the initial concentration was above 2 mg/mL. The 50 µL diluted samples were then mixed with 50 µL of 2× sample buffer composed of 125 mM Tris-HCl, pH 6.8, 4% SDS, 50% glycerol, 0.02% bromophenol blue, and 10% 2-mercaptoethanol. Mixed samples were incubated at 100° C. for 5 minutes and then placed on ice. 10 to 20 µL of the samples were loaded onto a 12% PAGEr™ Gold precast gel and run in a Hoefer SE260 chamber at 125V for 2 hours (running buffer: 25 mM Tris base, 192 mM glycine, 0.1% SDS) with chilling water circulating at 4° C. Molecular weight standards ProSieve® from BMA or Precision Plus Protein™ standards from Bio-Rad were added to lanes immediately adjacent to the sample lanes.

Determination of Protein Concentration

Protein concentration was determined by the Bradford method utilizing Coomassie Plus Protein assay reagent and pre-diluted protein assay standards-BSA (Pierce Chemical) for the calibration curve. Coomassie blue from Pierce (gelcode blue stain reagent, Pierce, Rockford, Ill.) were used in staining.

Example 8

Enzyme Assays

Nox activity assay: Cell-free extracts of the recombinant sfnox and bnox *E. coli* strains were prepared using ultrasonication described above in 0.1 M TEA pH 7.5+5 mM DTT or β-mercaptoethanol. Nox activities were assayed at 30° C. in a total volume of 1 mL at 340 nm using the following conditions: in 0.1 M TEA pH 7.5 a final concentration of 0.2 mM NADH was dissolved and 10 µl enzyme solution was added. Enzyme reaction was followed for 1 min, activity was calculated using an extinction coefficient ε of NADH of 6.22 L/(mol-cm).

Example 9

Fermentation

Production strains were grown in 5 ml cultures at 37° C. and 250 rpm in 15 ml disposable culture tubes to 1.0 OD 600 nm in LB media+100 ug/ml ampicillin. One liter cultures of LB medium supplemented with 5 g/L glycerol were seeded with 1 ml of the starter culture and grown at 30° C. and 200 rpm. Both baffled and unbaffled Fernbach shake flask were used for fermentation. When the cultures reached 1.0 OD 600 nm the flask were induced by addition of 0.5 mM IPTG and grown for an additional 3–4 hours. Additional ampicillin, 200 µg/ml, was added at induction and every hour thereafter to maintain selection pressure on the culture. When helper plasmids were present in the strains 50 µg/ml kanamycin was also added to the culture. Cultures were harvested by centrifugation at 5000 rpm in 1 L centrifuge containers (Beckman J2-M) and the resulting cell pellet was frozen at −80 C.

Example 10

Purification of sfnoxK2 Enzyme

Frozen cell pellets were thawed and resuspended in 10 ml of 100 mM potassium phosphate buffer pH 6.8+1 mM EDTA+5 mM DTT+5 mM spermine. The cell slurry was then sonicated with a Fisher Scientific 60 Sonic dismembrator for 6×2 minutes while floating the tube in ice water for cooling. The resulting lysate was centrifuged at 18,000 rpm in a Beckman J2-21M for 45 minutes at 4° C. The clarified lysate was then loaded into Spectro/Por® regenerated cellulose dialysis membrane tubing (60K MWCO) and dialyzed against 1 L of 45% ammonium sulfate+50 mM potassium phosphate buffer pH 6.8+1 mM EDTA+5 mM DTT. After four hours the sample was transferred to a second freshly prepared 45% ammonium sulfate solution. Following an additional 8 hours of dialysis (overnight), the sample was centrifuged at 18,000 rpm for 15 minutes at 4° C. The resulting solution was transferred to a Pierce Slide-A-Lyzer® dialysis cassette (10K MWCO) and dialyzed versus 20 mM 1-methylpiperazine buffer pH 5.0 and 30° C.+5 mM DTT. The sample was dialyzed versus a liter of buffer for two hours at 30° C. with stirring (200 rpm) on a digital magnetic stirplate/heater with a temperature probe to maintain the solution at 30° C. A buffer exchange was performed after one hour of dialysis. The sample was then transferred and centrifuged at 18,000 rpm for 15 minutes at 4° C. The resulting solution was then loaded onto a Amersham Pharmacia HiPrep 16/10 Q FF column on an AKTA system at 4° C. A gradient separation was performed from 0 to 100% 1 M NaCl with the running buffer 20 mM 1-methylpiperazine buffer pH 5.0 at 4° C. 5 ml fractions were collected over the course of the run and the nine most active fractions were pooled.

A second purification protocol utilized 100 mM 1-methylpiperazine buffer pH 5.0 in the lysis buffer. Frozen cell pellets were thawed and resuspended in 10 ml of 100 mM—methylpiperazine buffer pH 5.0+1 mM EDTA+5 mM DTT+5 mM spermine. The cell slurry was then sonicated with a Fisher Scientific 60 Sonic dismembrator for 6×2 minutes while floating the tube in ice water for cooling. The resulting lysate was centrifuged at 18,000 rpm in a Beckman J2-21M for 45 minutes at 4° C. The clarified lysate was then loaded into Spectro/Por® regenerated cellulose dialysis membrane tubing (60K MWCO) and dialyzed with 1 L of 20 mM 1-methylpiperazine buffer pH 5.0 at 35° C.+5 mM DTT. The sample was dialyzed versus 1 L of buffer for two hours at 35° C. with stirring (200 rpm) on a digital magnetic stirplate/heater with a temperature probe to maintain the solution at 35° C. A buffer exchange was performed after one hour of dialysis. The sample was then transferred and centrifuged at 18,000 rpm for 15 minutes at 4° C. The resulting solution was then loaded onto a Amersham Pharmacia Mono-Q column on an AKTA system at 4° C. A gradient separation over 10 column volumes was performed from 0 to 100% 1M NaCl with the running buffer 20 mM 1-methylpiperazine buffer pH 5.0 at 4° C. 1 mL fractions were collected over the course of the run and the most active fraction was dialyzed versus 45% ammonium sulfate+50 mM potassium phosphate buffer pH 6.2+1 mM EDTA+5 mM DTT. After four hours the sample was transferred to a second freshly prepared 1.5 liters of 45% ammonium sulfate solution. Following an additional 4 hours of dialysis the sample was centrifuged at 18,000 rpm for 15 minutes at 4° C.

Example 11

Hydrogen Peroxide Assay

A novel use of an assay for $H_2O_2$, based on fluorescence of resorufin rather than on UV-VIS spectroscopy of ABTS (2,2'-azino-bis[3-ethylbenzthiazoline-6-sulfonic acid])or o-dianisidine, has been employed successfully to demonstrate that both NADH oxidases of the present invention form $H_2O$ instead of $H_2O_2$ as co-product. With its detection limit of 100 nM, the test based on 9-acetyl-resorufin ("Amplex Red") is much more sensitive than the other assays mentioned. Horseradish peroxidase (HRP)-catalyzed oxidation of 9-acetyl resorufin ("Amplex Red") to fluorescent resorufin was the assay. Amplex Red reacts with $H_2O_2$ according to a strict 1:1 stoichiometry. The resorufin assay ($\lambda_{max}$: 587 nm (emission), $\epsilon$=54,000 L(mol-cm)$^{-1}$) with its extremely low detection limit of 100 nM resorufin product is much more sensitive than other assays, such as ABTS or o-dianisidine. [60–62].

For the sensitive assay of putative hydrogen peroxide formation during the reaction of NADH oxidase the horseradish peroxidase-catalyzed oxidation of 9-acetyl resorufin was employed. The Amplex Red hydrogen peroxide assay kit (A-22188) from molecular probes was utilized for these assays. Following the protocols outlined in the kit instructions, a standard curve of $H_2O_2$ was prepared in the reaction buffer (50 mM sodium phosphate buffer pH 7.4) from the peroxide stock. The prepared concentrations were 20, 10, 5, and 2.5 μM $H_2O_2$ and 0 as a control. A working solution of 100 μM Amplex Red reagent and 0.2 U/ml horseradish peroxidase (HRP) was prepared in the reaction buffer as per kit instructions. As NADH and other reducing reagents are known to interfere with the amplex red assay, the NADH oxidase enzymes were allowed to react with the substrate immediately prior to the Amplex Red analysis. Reaction buffer from the kit was utilized in running enzyme test with 300 μM NADH as well as the controls without NADH. The enzyme conversions were performed by adding 3 μl of enzyme prep to 3 ml of reaction buffer with 300 μM NADH, mixing, and following the conversion until completion by absorbance at 340 nm. 50 μl of the final reaction mixture and standard curve solutions were added to each well in a 96 well fluorescence plate (costar, black, pp). Five replicates were made per sample and standard curve point. 50 μl of the Amplex Red reagent was added to each well and incubated for 30 minutes at 30° C. Fluorescence readings were performed in a BMG FLUOstar Galaxy micro plate reader with 544ex/590em filter settings.

0.6 μM resorufin above background was detected (and thus an equal concentration of $H_2O_2$ formed) upon conversion of 300 μM NADH with SFNOX (0.2% yield) but could not detect any resorufin above background in our experiment with BNOX. The value found for SFNOX was above the detection limit of 0.25 μM [60] so it might indicate leakage of $H_2O_2$ which is formed during the operation of NADH oxidase. Nevertheless, any $H_2O_2$ formed only constitutes a very minor component of the product flux of SFNOX, showing that water indeed is the co-product formed during the NADH oxidase reaction of SFNOX and BNOX.

Example 12

Kinetics of Cofactor Substrates

The kinetic analysis was performed on ammonium sulfate fractions from both the sfnox and bnox strains in 50 mM HEPES buffer pH 7.0 at 30° C. The initial enzyme fractions were diluted in 25 mM HEPES pH 7.0 at 30° C.+25% glycerol+5 mM DTT to approximately –0.05 A340 nm/min and retained on ice during analysis. Conversion of NAD(P)H was followed by change of absorbance at 340 nm in a Jasco V-530 spectrophotometer. 3 mL methylacrylate disposable cuvettes were used for all experiments and all runs were performed in triplicate at 30° C. Reactions with NADH were started by adding 3 μL of enzyme preparation, 9 μL for NADPH, to the cuvette and mixing by inversion with parafilm three times. Varying concentrations of NAD(P)H substrate were made my preparing 100 mL of a 300 μM solution in a volumetric flask. Dilutions of this solution were then made to provide the differing substrate concentrations for the kinetic profile.

Regarding the kinetics SFNOX, it was found that both NADH and NADPH bind rather tightly, as judged by the low $K_M$ value of 6.7 μM. Surprisingly, however, NADPH turned out to be almost as good a substrate as NADH: its $v_{max}$ of 11 U/mg (at pH 7.0) is about a quarter of the value for NADH with 39.3 U/mg. SFNOX is much more active in comparison with BNOX: at comparable degree of purity, the latter only has a $v_{max}$ of 2.03 U/mg, and furthermore does not accept NADPH as a substrate.

Figure 3A:
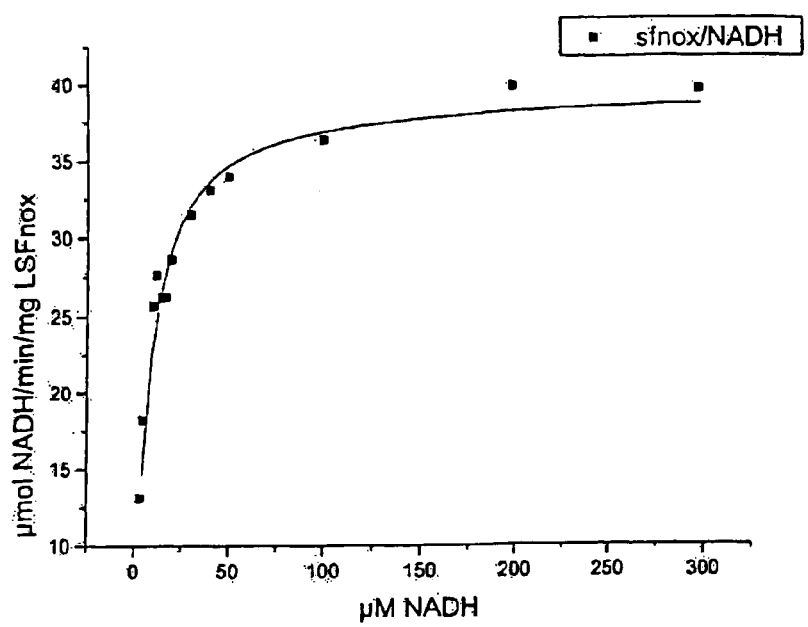
FIG. 3A-3C are graphs of the kinetics of SFNOX and BNOX with NAD(P)H cofactor in air-saturated solution at pH 7 and 30° C.
Figure 3B:
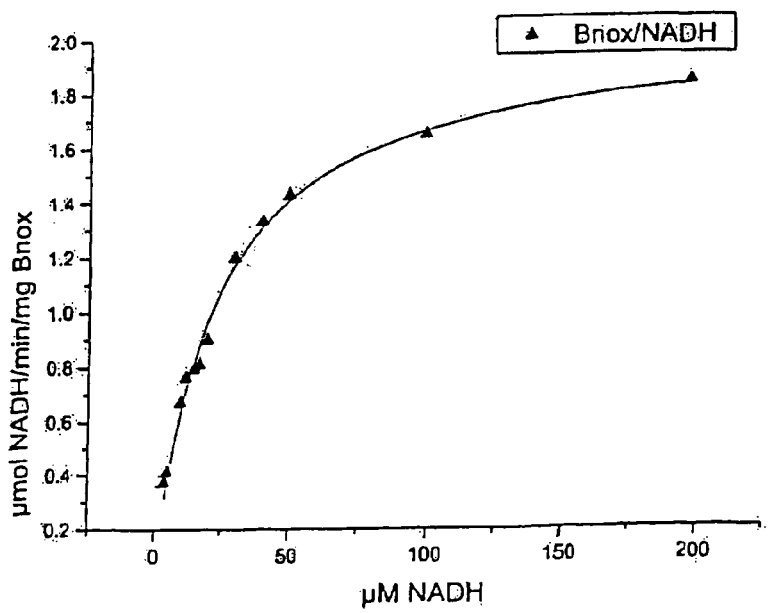
Figure 3C:
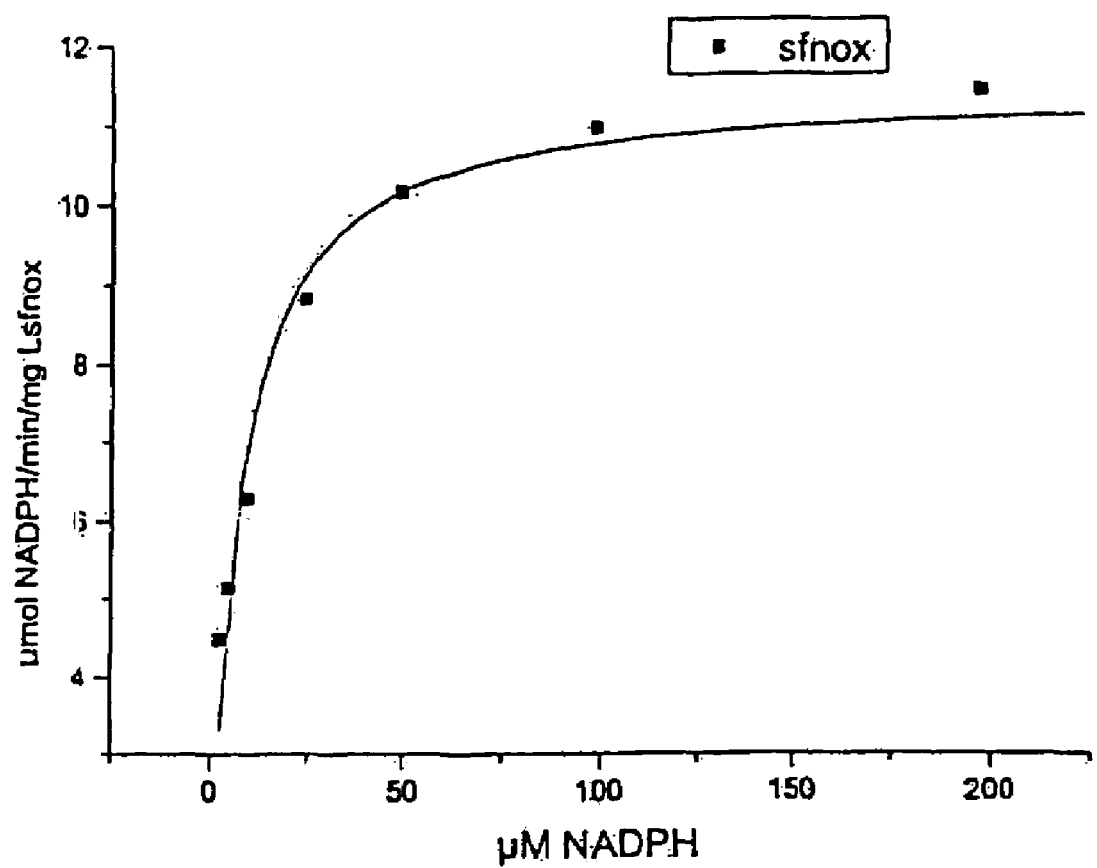

Investigation of kinetic parameters with NADH and NADPH cofactors as substrates was performed with the supernatant of the 45% ammonium sulfate cut (40% for BNOXK6) in air-saturated solution at 30° C. and pH 7.0 in 0.1 M HEPES buffer. FIG. 3A-C demonstrates that not only does the SFNOX accept NADPH as a substrate with good reactivity ($v_{max}$=11 U/mg), about 30% of activity towards NADH ($v_{max}$=39.3 U/mg), but nearly identical $K_M$ values of 6.7 and 6.1 μM indicate similar binding affinity. In contrast, BNOX only accepts NADH and at a higher $K_M$ value of 22.0 μM than SFNOX. Chi values and error bars reveal high accuracy with <10% error in most cases. FIG. 3A-C shows the kinetics of SFNOX and BNOX with NAD(P)H cofactor in air-saturated solution at pH 7 and 30° C.

The activity profile as a function of pH showed a surprising feature: instead of a bell-shaped curve a bimodal curve with a minimum around pH 5.5 was found. As this pH value is very close to the calculated pI value of pH 5.4, it is believed that the enzyme is not active and/or not stable at its pI value. As a pH optimum in the acidic range is not very common, the superposition of pH optimum and pI does not happen frequently.

Figure 4:
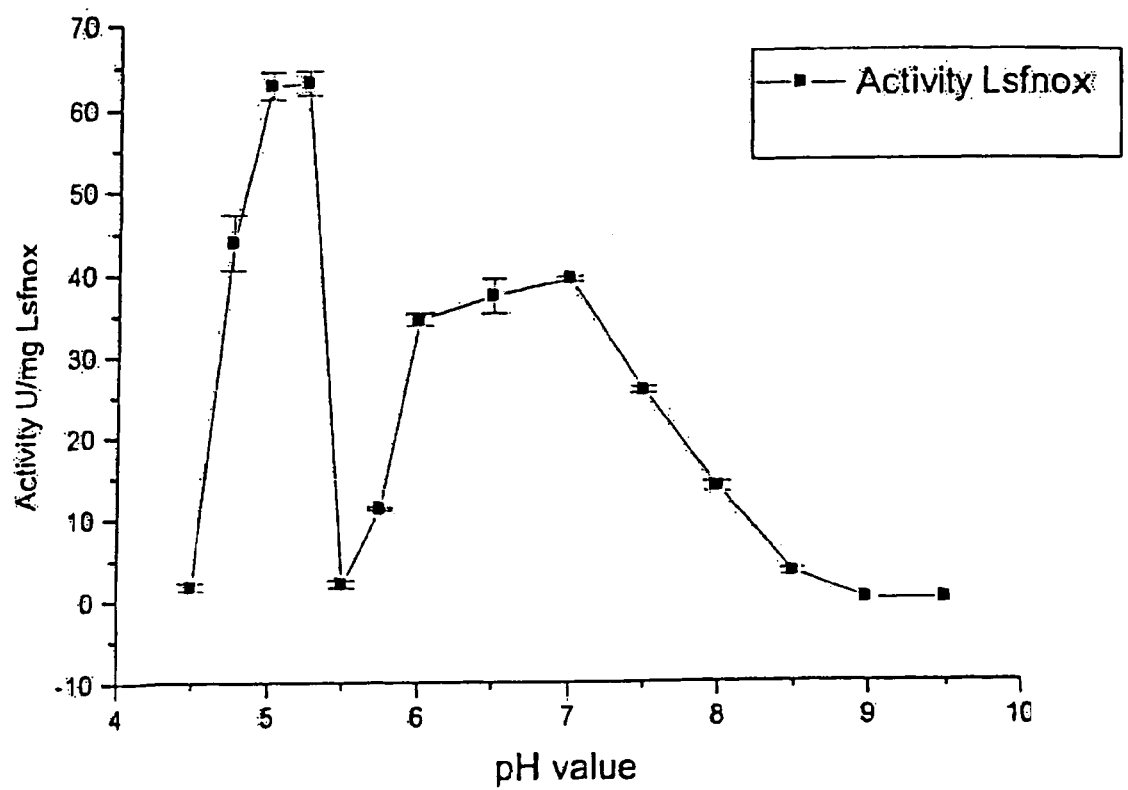
FIG. 4 is a graph showing activity-pH-profile of $L.$ $sanfranciscensis$ NADPH oxidase

With the supernatant of the 45% ammonium sulfate cut, an activity—pH profile was measured for SFNOX (FIG. 4). The pH optimum of activity was found at pH 5.2. Below pH 5, activity decreased markedly and reached zero at pH 4.5. Rates at pH 4.5 to 5.2 are reported as net rates, with the chemical decomposition rate at low pH subtracted. At pH values above 5.2, activity falls off sharply before recovering significantly at pH 6.0, reaching a peak at pH 7.0, and then gradually leveling off up to pH 8.5. The sharp activity decline between pH 5.2 and 6.0 coincides with the enzyme's pI, calculated to be pH 5.4. At pH 5.5, samples instantaneously lose activity, except for a very small residual activity.

Example 13

Activity-pH Profile of sfnoxK2

The pH profile was performed on ammonium sulfate fractions from the sfnoxK2. 100 mM buffer solutions at 30° C. and 200 µM NADH were used for activity analysis as monitored by absorbance at 340 nm. All samples were tested in triplicate in 3 mL methylacrylate disposable cuvettes. The following buffers were utilized within the buffering range of 1 pH unit from their pKa: acetate, N-methylpiperazine, MES (2-[N-morpholino]ethanesulfonic acid hydrate), and bis-tris-propane. Sodium hydroxide or hydrochloric acid were used in preparation of the respective buffers.

Example 14

Purification of NADH Oxidase

A modified purification strategy was employed to obtain highly purified NADH oxidase. Frozen cell pellets, 13 g WCP, were thawed and resuspended in 30 mL of 100 mM 1-methylpiperazine buffer pH 5.0+1 mM EDTA+5 mM DTT+5 mM Spermine. The resulting cell slurry was sonicated with a Fisher Scientific 60 Sonic dismembrator for 6×2 minutes while floating the tube in ice/water for cooling. The resulting lysate was centrifuged at 20,000 rpm in a Beckman J2-21M for 45 minutes at 4° C. The clarified lysate was then loaded into Specto/Por® regenerated cellulose dialysis membrane tubing (60 K MWCO) and dialyzed with 1.5 L of 20 mM 1-methylpiperazine pH 5.0 at 30° C.+1 mM EDTA+ 10 mM β-mercaptoethanol. This step comprises the acid precipitation step along with concurrent dialysis for salt removal. The sample was dialyzed versus 1.5 L of buffer for two hours at 30 C and 200 rpm stirring before exchanging the dialysis buffer and dialyzing for two more hours under the same conditions. Temperature and stirring conditions were maintained by a digital stir plate with and external temperature probe. The sample was then transferred and centrifuged at 20,000 rpm for 45 minutes at 4° C. The resulting clarified solution was then loaded onto a Amersham Pharmacia Hiprep 16/10 Source™ 30Q column on an AKTAexplorer system at 4° C. The protein was then eluted with displacement chromatography utilizing 5 mM naphthalene-1,3,6-trisulfonic acid. After sample loading the column was washed with 10 column volumes of 20 mM 1-methylpiperazine pH 5.0 at 4° C.+5 mM DTT. The protein elution phase was then started by switching to 20 mM 1-methylpiperazine pH 5.0 at 4° C.+5 mM DTT+5 mM naphthalene-1, 3,6-trisulfonic acid. 5 mL factions were collected at a flow rate of 5 ml/min. Fractions with a tested specific activity of over 200 were pooled and dialyzed at 4° C. against 2 L of 45% Ammonium sulfate+50 mM potassium phosphate buffer pH 6.8+1 mM EDTA+10 mM β-mercaptoethanol using Specto/Por® regenerated cellulose dialysis membrane tubing (14 kD MWCO). The total dialysis time was 12 hours with one buffer exchange after 6 hours. The resulting concentrated preparation of 23 mL total volume and 1.3 mg/mL was stored at 4° C. No additional purification or loss of activity was apparent in the 45% ammonium sulfate preparation. The preparation was measured to have an activity of 137 U/mL or 221 U/mg protein on NADH on the day the coupled experiments were started.

Samples of the purified enzyme preparations were run on a 12% Tris-Glycine SDS-PAGE gel (PAGEr® gold precast gel). The running buffer and sample were prepared according to the manufacturers protocol. The NADH oxidase sample was diluted 1:10 in DI water prior to mixing with sample loading buffer. 20 µL of the wildtype ADH, G37D ADH mutant, and NADH oxidase (dil) samples were mixed with an equal volume of 2× sample loading buffer, vortexed, and then incubated in a water bath at 95° C. for fifteen minutes. Due to the presence of 50% glycerol in the purified wildtype ADH and G37D ADH mutant samples, sample-loading buffer without glycerol was utilized. Samples were then centrifuged at 14,000 g for 5 minutes and placed on ice prior to loading on the gel. 15 to 30 µL of each sample was loaded into the wells with blank sample buffer added to the empty wells. The gel was run on a Hoefer Mighty Small™ (SE260) with circulated cooling water at 4° C. The gel was run under constant voltage (125V) for 2.5 hours. At the completion of the electrophoresis run, the gel was washed with three changes of DI water. The gel was then stained with Pierce Gelcode blue for 1 hour and then transferred to DI water to destain for an additional hour. Images were taken in an Alpha Innotech Alphalmager 3300 for gel documentation.

Example 15

Cofactor Regenerating Assay:

Application of NADH oxidase in cofactor regeneration is performed using a batch conversion with R-ADH as the production enzyme. All reactions were run at 30° C. with standard buffer composed: 50 mM HEPES pH 7.0 at 30° C. and 150 mM total ionic strength by addition of 138 mM NaCl, 5 mM DTT, 1 mM $MgCl_2$, and 100 mM racemic phenylethanol. Cofactors and enzymes were then added to 100 µL of buffer as outlined in Table 3 and vortexed. 30 µL of the mixed solution was then added to 0.65 mL polypropylene PCR reaction tubes, capped, and floated in a water bath. Three identical vials were prepared for each condition. Time point samples were taken by centrifuging for 1 min at 14,000 rpm in a Microfuge and adding 270 µL methanol to the reaction vial.

Figure 5:
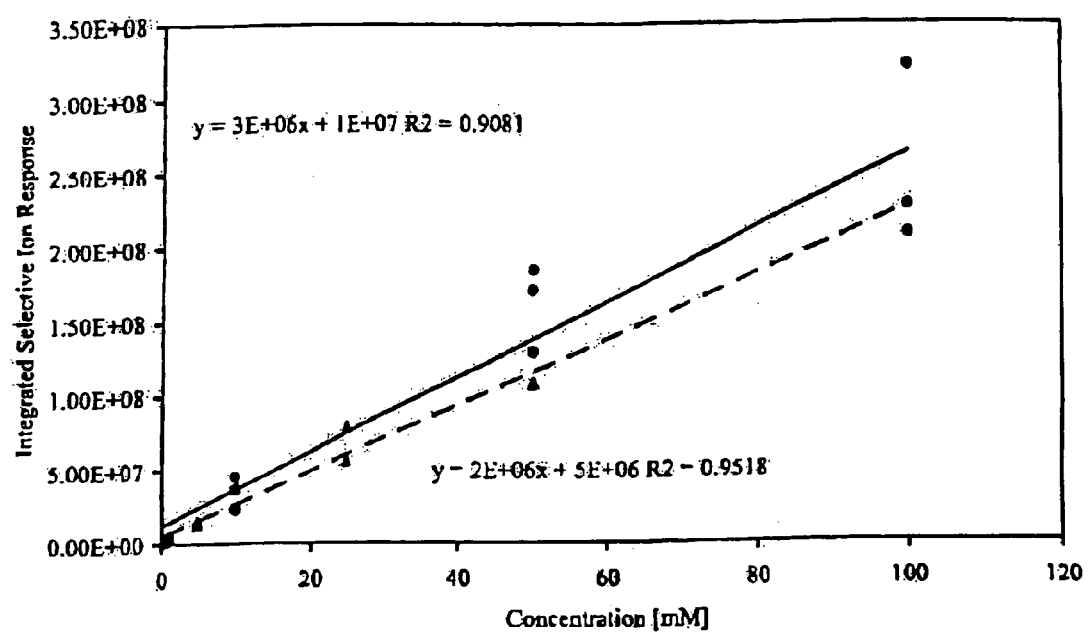
FIG. 5 is a graph of the standard curve for selective ion monitoring of phenylethanol (● mass 122) acetophenone (▲ mass 120)

The results of coupled reactions after 12 hours, as analyzed by selective ion monitoring (SIM) mass spectrometry, are shown in Table 4. The standard curves used for SIM mass spectrometry are shown in FIG. 5. Measured degrees of conversion values were normalized using the mass balance of acetophenone and phenylethanol to correct for manual injection error. Satisfactory linearity was obtained for both phenylethanol and acetophenone up to 100 mM concentration.

TABLE 4

Coupled alcohol-ketone conversion with cofactor regeneration

| Sample# | Cofactor (4 mM) | ADH (U/ml) | ADH mut (U/ml) | NADH ox (U/ml) | Normalized Conversion (%) | Turnovers |
|---|---|---|---|---|---|---|
| 1 | NAD | | 2.0 | 8.0 | 43.6 | 10.9 |
| 2 | NADH | | 2.0 | 8.0 | 35.0 | 8.7 |
| 3 | NADP | 2.0 | | 8.0 | 38.2 | 9.5 |
| 4 | NADPH | 2.0 | | 8.0 | 40.1 | 10.0 |
| 5 | NAD | | | 8.0 | −2.3 | −0.6 |
| 6 | NAD | | 2.0 | | 1.7 | 0.4 |
| 7 | NADP | | | 8.0 | −0.7 | −0.2 |
| 8 | NADP | 2.0 | | | 2.3 | 0.6 |
| 9 | NAD* | | 2.0 | 8.0 | 43.6 | 109.0 |
| 10 | NADP* | 2.0 | | 8.0 | 40.2 | 100.5 |
| 11 | NAD* | | 2.0 | 4.0 | 27.9 | 69.8 |
| 12 | NADP* | 2.0 | | 4.0 | 41.7 | 104.1 |

*These samples utilized 0.4 mM concentrations of cofactor.

Standard Conditions:

30° C., pH 7.0 (50 mM HEPES), 5 mM DTT, 1 mM $MgCl_2$, 150 mM total ionic strength (addition of 138 mM NaCl), and 100 mM racemic phenylethanol.

The coupled reaction results shown in Table 4 are consistent with expected results from successfully coupled reactions. The comparison of reduced versus oxidized cofactor (runs 1 & 2 a well as 3 & 4) indicate that the starting oxidation state of the cofactor does not significantly impact the results. Given the higher stability and lower cost, the oxidized cofactor would be the reagent of choice for typical coupled reactions. The controls (runs 5–8) demonstrated that no conversion occurs without ADH (runs 5 & 7) and that slightly less than stoichiometric conversion was observed in the absence of NADH oxidase (runs 6 & 8) to regenerate the cofactor. Conversions in excess of stoichiometry would have indicated a potential NAD(P)H-oxidizing impurity in the ADH preparations. Reducing the cofactor concentration to 0.4 mM (runs 9–12) still indicated effective conversion with concomitant higher number of turnovers of cofactor; however, a lower degree of conversion was observed for the mutant ADH in the presence of 4 U/mL instead of 8 U/mL NADH oxidase. After 12 h, nearly complete conversion (maximally 50% of racemic phenylethanol) was achieved in all but the case of the mutant ADH with NAD+.

Example 16

GC/MS Analysis

Samples and a prepared standard curve were submitted to the IBB central mass spectroscopy facility for GC/selective ion analysis. The separate standard curves were prepared for the ±phenylethanol and acetophenone. The ±phenylethanol curve consisted of 100 mM, 10 mM, and 1 mM in the coupled reaction base buffer, diluted 1:10 in methanol. The acetophenone curve consisted of 50 mM, 10 mM, and 1 mM in the coupled reaction base buffer, diluted 1:10 in methanol. Total mass areas were reported for ions of mass 120 (acetophenone) and 122 (±phenylethanol). Sample concentrations from the coupled reaction were estimated by interpolation on these standard curves ($R^2$ for both curves>0.90).

Whereas this invention has been described in detail with particular reference to its most preferred embodiments, it will be apparent to those skilled in the art that various modifications and variations can be made in the present invention in light of the above teachings without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

[1] A. Zaks, "Industrial biocatalysis", Curr. Opin. Chem. Biol. 2001, 5, 130–136

[2] A. Liese and M. V. Filho, "Production of fine chemicals using biocatalysis", Curr. Opin. Biotechnol. 1999, 10, 595–603

[3] J. D. Rozzell, "Biocatalysis at commercial scale: Myths and realities", Chimica Oggi 1999, 42–47

[4] A. S. Bommarius, M. Schwarm and K. Drauz, "Comparison of Different Chemoenzymatic Process Routes to Enantiomerically Pure Amino Acids", Chimia 2001, 55, 50–59

[5] D. A. Evans, T. C. Britton, J. A. Ellman and R. L. Dorow, 1990, "The asymmetric synthesis of α-amino acids. Electrophilic azidation of chiral imide enolates, a practical approach to the synthesis of (R)- and (S)-α-azido carboxylic acids", J. Am. Chem. Soc., 112, 4011–4030

[6] U. Groth, C. Schmeck and U. Schöllkopf, 1993, "Asymmetric synthesis of α-amino acid benzyl esters via the bisbenzyl bislactim ether of cyclo(-L-Val-Gly-)", Liebigs Ann. Chem., 321–323

[7] W. Hummel, 1997, "New alcohol dehydrogenases for the synthesis of chiral compounds", Adv. Biochem. Eng. Biotechnol., 58, 145–84

[8] M. J. Kim and G. M. Whitesides, 1988, "L-Lactate dehydrogenase: substrate specificity and use as a catalyst in the synthesis of homochiral 2-hydroxy acids", J. Am. Chem. Soc., 110, 2959–64

[9] H. K. W. Kallwass, 1992, "Potential of R-2-hydroxyisocaproate dehydrogenase from *Lactobacillus casei* for stereospecific reductions", Enzyme Microb. Technol., 14, 28–35

[10] G. Krix, A. S. Bommarius, K. Drauz, M. Kottenhahn, M. Schwarm and M.-R. Kula, 1997, "Enzymatic reduction of α-keto acids leading to L-amino acids or D-hydroxy Acids", J. Biotechnology, 53, 29–39

[11] Y. Asano, A. Yamada, Y. Kato, K. Yamaguchi, Y. Hibino, K. Hirai and K. Kondo, 1990, "Enantioselective synthesis of (S)-amino acids by phenylalanine dehydrogenase from *Bacillus sphaericus*: Use of natural and recombinant enzymes", J. Org. Chem., 55, 5567–5571

[12] C. W. Bradshaw, C. H. Wong, W. Hummel and M.-R. Kula, 1991, "Enzyme-catalyzed asymmetric synthesis of (S)-2-amino-4-phenylbutanoic acid and (R)-2-hydroxy-4-phenylbutanoic acid", Biorg. Chem., 19, 29–39

[13] R. L. Hanson, J. M. Howell, T. L. LaPorte, M. J. Donovan, D. L. Cazzulino, V. V. Zannella, M. A. Montana, V. B. Nanduri, S. R. Schwarz, R. F. Eiring, S. C. Durand, J. M. Wasylyk, W. L. Parker, M.S. Liu, F. J. Okuniewicz, B. Chen, J. C. Harris, K. J. Natalie, K. Ramig, S. Swaminathan, V. W. Rosso, S. K. Pack, B. T. Lotz, P. J. Bernot, A. Rusowicz, D. A. Lust, K. S. Tse, J. J. Venit, L. J. Szarka, and R. N. Patel, 2000, "Synthesis of allysine ethylene acetal using phenylalanine dehydrogenase from Thermoactinomyces intermedius", Enzyme Microb Technol, 26, 348–358

[14] R. L. Hanson, M. D. S., A. Banerjee, D. B. Brzozowski, B.-C. Chen, B. P. Patel, C. G. McNamee, G. A. Kodersha, D. R. Kronenthal, R. N. Patel and L. J. Szarka, Bioorganic & Medicinal Chemistry 1999, 7, 2247–2252

[15] A. Willetts, 1997, "Structural studies and synthetic applications of Baeyer-Villiger monooxygenases", Trends Biotechnol., 15, 55–62

[16] M.-R. Kula, 1994, "Enzyme catalyzed reductions of carbonyl groups", Chiral Europe, Nice, France, Spring Innovations, Ltd., Stockport UK

[17] H. K. Chenault, G. M. Whitesides, Appl. Biochem. Biotechnol. 1987, 14, 147–97

[18] C. Wandrey, in: Proceedings of the 4th European Congress on Biotechnology (eds.: O. M. Neijssel, R.R. van der Meer, and K. Ch. A. M. Luyben), Amsterdam, 1987, vol. 4, 171–188

[19] E. Keinan, K.K. Seth, R. J. Lamed, Ann. NY Acad. Sciences (Enzyme Engineering 8) 1987, 501, 130–150

[20] W. Hummel, M.-R. Kula, Eur. J. Biochem, 1989, 184, 1–13

[21] R. Wichmann, C. Wandrey, A. F. Bueckmann, M.-R. Kula, J. Biotechnol, 1981, 23, 2789–2802

[22] U. Kragl, D. Vasic-Racki, C. Wandrey, Chem. Ing. Tech, 1992, 64, 499–509

[23] A. S. Bommarius, Habilitation thesis, RWTH Aachen, Aachen, Germany, 2000

[24] V. I. Tishkov, A. G. Galkin, V. V. Fedorchuk, P. A. Savitsky, A. M. Rojkova, H. Gieren, M.-R. Kula, Biotechnol. Bioeng. 1999, 64, 187–93

[25] K. Seelbach, B. Riebel, W. Hummel, M.-R. Kula, V. I. Tishkov, A. M. Egorov, C. Wandrey, U. Kragl, Tetrahedron Letters 1996, 37, 1377–80

[26] C.-H. Wong, G. M. Whitesides, J. Amer. Chem. Soc. 1981, 103, 4890–4899

[27] C.-H. Wong, D. G. Drueckhammer, Bio/technology 1985, 3, 649–651

[28] D. G. Drueckhammer, PhD Thesis, Texas A and M Univ., College Station/TX, USA, 1987

[29] M. Kataoka, L. P. Rohani, K. Yamamoto, M. Wada, H. Kawabata, K. Kita, H. Yanase, S. Shimizu, Appl. Microbiol. Biotechnol. 1997, 48, 699–703

[30] R. P. Ross, A. Claiborne, J. Mol. Biol. 1992, 227, 658–71

[31] J. Matsumoto, M. Higushi, M. Shimada, Y. Yamamoto, Y. Kamio, Biosci. Biotechnol. Biochem. 1996, 60, 39–43

[32] D. E. Ward, C. J. Donnelly, M. E. Mullendore, J. van der Oost, W. M. de Vos, and E. J. Crane 3rd, Eur. J. Biochem. 2001, 268, 5816–23

[33] Y. Yamamoto, Y. Kamio, Tanpakushitsu Kakusan Koso 2001, 46, 726–32

[34] B. R. Riebel, P. R. Gibbs, W. B. Wellborn, A. S. Bommarius, Adv. Synth. Cat. 2002, 344, 1156–1169

[35] W. Hummel and M.-R. Kula, 1989, "Dehydrogenases for the synthesis of chiral compounds", Eur. J. Biochem., 184, 1–13

[36] T. Ohshima and K. Soda, 1990, "Biochemistry and biotechnology of amino acid dehydrogenases", Adv. Biochem. Eng./Biotech., 42, 187–209

[37] W. Hummel, "Large-scale applications of NAD(P)-dependent oxidoreductases: recent developments", TIBTECH 1999, 17, 487–492

[38] R. Wichmann, C. Wandrey, A. F. Bïckmann and M.-R. Kula, 1981, "Continuous enzymatic transformation in an enzyme membrane reactor with simultaneous NADH regeneration", Biotechnol. Bioeng., 23, 2789–2802

[39] M.-R. Kula and C. Wandrey, 1987, "Continuous enzymatic transformation in an enzyme-membrane-reactor with simultaneous NADH regeneration", Meth. Enzymol. 136, 9–21

[40] G. L. Lemière, J. A. Lepoivre and F. C. Alderweireldt, 1985, "HLAD-catalyzed oxidations of alcohols with acetaldehyde as a coenzyme recycling substrate", Tetrahedron Lett., 26, 4527–28

[41] a) M. D. Bednarski, H. K. Chenault, E. S. Simon and G. M. Whitesides, 1987, "Membrane-enclosed enzymic catalysis (MEEC): a useful, practical new method for the manipulation of enzymes in organic synthesis", J. Amer. Chem. Soc., 109, 1283–85; b) H. K. Chenault and G. M. Whitesides, 1989, "Lactate dehydrogenase-catalyzed regeneration of NAD from NADH for use in enzyme-catalyzed synthesis", Bioorg. Chem., 17, 400–9

[42] G. Carrea, R. Bovara, R. Longhi and S. Riva, 1985, "Preparation of 12-ketochenodeoxycholic acid from cholic acid using coimmobilized 12$\alpha$-hydroxysteroid dehydrogenase and glutamate dehydrogenase with NADP+ cycling at high efficiency", Enz. Microb. Technol., 7, 597–600

[43] L. G. Lee and G. M. Whitesides, 1985, "Enzyme-catalyzed organic synthesis: a comparison of strategies for in situ regeneration of NAD from NADH", J. Am. Chem. Soc., 107, 6999–7008

[44] H. J. Park, C. O. Reiser, S. Kondruweit, H. Erdmann, R. D. Schmid and M. Sprinzl, 1992, "Purification and characterization of a NADH oxidase from the thermophile *Thermus thermophilus* HB8", Eur. J. Biochem., 205, 881–5

[45] R. E. Altomare, J. Kohler, P. F. Greenfield and J. R. Kittrell, 1974, "Deactivation of immobilized beef liver catalase by hydrogen peroxide", Biotechnol. Bioeng., 16, 1659–73

[56] K. Koike, T. Kobayashi, S. Ito and M. Saitoh, 1985, "Purification and characterization of NADH Oxidase from a strain of *Leuconostoc meserentoides*", J. Biochem., 97, 1279–1288

[47] R. P. Ross and A. Claiborne, 1991, "Cloning, sequence and overexpression of NADH peroxidase from *Streptococcus faecalis* 10CI. Structural relationship with the flavoprotein disulfide reductases", J. Mol. Biol., 221, 857–871

[48] R. P. Ross and A. Claiborne, 1992, "Molecular Cloning and Analysis of the Gene Encoding the NADH-Oxidase from *Streptococcus faecalis* 10CI. Comparison with NADH-Peroxidase and the Flavoprotein Disulfide Reductases", J. Mol. Biol., 227, 658–671

[49] S. N. Peterson, P. C. Hu, K. F. Bott and C. A. Hutchinson 3rd, 1993, "A survey of the *Mycoplasma genitalium* genome by using random sequencing", J. Bacteriol., 175, 7918–7930

[50] J. Matsumoto, M. Higushi, M. Shimada, Y. Yamamoto and Y. Kamio, 1996, "Molecular cloning and sequence analysis of the gene encoding the H₂O-Forming NADH Oxidase from *Streptococcus mutans*", Biosci. Biotech. Biochem., 60, 39–43

[51] C. J. Bult, O. White, G. J. Olsen, L. Zhou, R. D. Fleischmann, G. G. Sutton, J. A. Blake, L. M. FitzGerald, R. A. Clayton, J. D. Gocayne, A. R. Kerlavage, B. A. Dougherty, J. F. Tomb, M. D. Adams, C. I. Reich, R. Overbeek, E. F. Kirkness, K. G. Weinstock, J. M. Merrick, A. Glodek, J. L. Scott, N. S. Geoghagen, J. C. Venter, 1996, "Complete genome sequence of the methanogenic archaeon, *Methanococcus jannaschii*", Science, 273, 1058–1073

[52] V. Natarajan, S. M. Cramer, J. Chromatography A 2000, 876, 63–73

[53] A. Kundu, S. Vunnum, S. M. Cramer, J. Chromatography A 1995, 707, 57–67

[54] W. Hummel, Adv. Biochem. Eng. 1997, 58, 145–184

[55] B. Riebel, W. Hummel, A. Bommarius, Eur. Pat. Appl. EP 1,176,203, 2002

[56] W. Hummel, Trends Biotechnol, 1999, 17, 487–92

[57] B. Riebel, PhD thesis, University of Düsseldorf, Düsseldorf, Germany, 1997

[58] M. Wolberg, W. Hummel, M. Mueller, Chemistry 2001, 7, 4562–71

[59] J. Haberland, A. Kriegesmann, E. Wolfram, W. Hummel, A. Liese, Appl. Microbiol Biotechnol, 2002, 58, 595–9

[60] S. Lindsay, D. Brosnahan and G. D. Watt, 2001, "Hydrogen peroxide formation during iron deposition in horse spleen ferritin using O₂ as an oxidant", Biochemistry, 40, 3340–7

[61] M. Zhou, Z. Diwu, N. Panchuk-Voloshina, R. P. Haugland, 1997, "A stable nonfluorescent derivative of resorufin for the fluorometric determination of trace hydrogen peroxide: applications in detecting the activity of phagocyte NADPH oxidase and other oxidases", Anal. Biochem., 253, 162–168

[62] J. G. Mohanty, J. S. Jaffe, E. S. Schulman and D. G. Raible, 1997, "A highly sensitive fluorescent micro-assay of H₂O₂ release from activated human leukocytes using a dihydroxyphenoxazine derivative", J. Immunol. Methods, 202, 133–141

[63] R. K. Scopes, *Protein purification: principles and practice*, Springer, New York, 3rd edition, 1994

[64] B. R. Riebel, P. R. Gibbs, W. B. Wellborn and A. S. Bommarius, "Cofactor regeneration of NAD+ from NADH: novel water-forming NADH oxidases", *Adv. Synth. Catal.* 2002, 344, 1156–1168.

[65] B. R. Riebel, P. R. Gibbs, W. B. Wellborn and A. S. Bommarius, Cofactor regeneration of both NAD+ from NADH and NADP+ from NADPH: NADH oxides from *Lactobacillus sanfranciscensis*", *Adv. Synth. Catal.* 2003, 345, 707–712.

---

What is claimed is:

1. An isolated bacterial oxidase, comprising an oxidase that regenerates NADP+, NAD+, or both;
   wherein the oxidase is isolated from *Lactobacillus*; and
   wherein the bacterial oxidase protein comprises the amino acid sequence of SEQ ID NO.: 4.

2. The bacterial oxidase of claim 1, wherein the oxidase is isolated from *Lactobacillus sanfranciscensis*.

3. The bacterial oxidase of claim 1, wherein the oxidase is encoded by a nucleic acid sequence comprising SEQ ID NO: 3.

4. The bacterial oxidase of claim 1, wherein the bacterial oxidase is capable of forming a reaction product comprising one or more chiral compounds.

5. The bacterial oxidase of claim 1, wherein essentially no $H_2O_2$ is produced by the bacterial oxidase in a reaction for regenerating NADP+, NAD+, or both.

6. The bacterial oxidase of claim 1, wherein the bacterial oxidase binds essentially equally to NADP+ or NAD+.

7. The bacterial oxidase of claim 1, wherein the bacterial oxidase has a normalized conversion value of more than about 27.9% using a cofactor regenerating assay.

8. The bacterial oxidase of claim 1, wherein the bacterial oxidase has a turnover ratio of more than about 8.7 using a cofactor regenerating assay.

9. The bacterial oxidase of claim 1, wherein the oxidase has a $K_m$ value of less than about 6.7 μM, wherein the $K_m$ value is the $K_m$ value of the binding of the oxidase with NADP+ or NAD+.

* * * * *

SEQUENCE LISTING

```
<160> NUMBER OF SEQ ID NOS: 20

<210> SEQ ID NO 1
<211> LENGTH: 1359
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1359)

<400> SEQUENCE: 1 atg aaa gtt att gta gta ggt tgt act cac gct ggc act ttt gca gtt      48
Met Lys Val Ile Val Val Gly Cys Thr His Ala Gly Thr Phe Ala Val
1               5                   10                  15 aag caa acg att gcc gat cac ccc gat gca gat gtg act gca tat gaa      96
Lys Gln Thr Ile Ala Asp His Pro Asp Ala Asp Val Thr Ala Tyr Glu
            20                  25                  30 atg aat gat aac att tcc ttt tta tca tgt gga atc gcc ctt tac tta     144
Met Asn Asp Asn Ile Ser Phe Leu Ser Cys Gly Ile Ala Leu Tyr Leu
        35                  40                  45 ggt aaa gaa att aaa aac aat gat ccc cga ggg ctt ttc tac tca agt     192
Gly Lys Glu Ile Lys Asn Asn Asp Pro Arg Gly Leu Phe Tyr Ser Ser
    50                  55                  60 cca gaa gaa tta agc aat ctt gga gct aac gtc caa atg cgt cat caa     240
Pro Glu Glu Leu Ser Asn Leu Gly Ala Asn Val Gln Met Arg His Gln
65                  70                  75                  80 gtt aca aac gtt gat cca gaa aca aaa aca atc aaa gtt aaa gat tta     288
```

-continued

| | | |
|---|---|---|
| Val Thr Asn Val Asp Pro Glu Thr Lys Thr Ile Lys Val Lys Asp Leu<br>               85                     90                 95 | | |
| atc acc aac gaa gaa aaa aca gaa gca tat gac aaa tta att atg acc<br>Ile Thr Asn Glu Glu Lys Thr Glu Ala Tyr Asp Lys Leu Ile Met Thr<br>               100                   105                110 | 336 |
| act ggt tct aag cct act gtt cct cca atc cct gga atc gat agt agt<br>Thr Gly Ser Lys Pro Thr Val Pro Pro Ile Pro Gly Ile Asp Ser Ser<br>               115                   120                125 | 384 |
| cgc gtt tac ctt tgt aaa aac tat aac gat gct aaa aag tta ttt gaa<br>Arg Val Tyr Leu Cys Lys Asn Tyr Asn Asp Ala Lys Lys Leu Phe Glu<br>130                   135                   140 | 432 |
| gaa gct ccc aaa gct aaa acg att act atc att ggt tct ggt tat att<br>Glu Ala Pro Lys Ala Lys Thr Ile Thr Ile Ile Gly Ser Gly Tyr Ile<br>145                   150                   155                160 | 480 |
| ggt gcc gaa ctg gct gaa gcc tac tca aac caa aat tat aac gtt aat<br>Gly Ala Glu Leu Ala Glu Ala Tyr Ser Asn Gln Asn Tyr Asn Val Asn<br>               165                   170                175 | 528 |
| tta att gat ggt cat gaa cga gtt ctt tac aag tat ttt gat aaa gaa<br>Leu Ile Asp Gly His Glu Arg Val Leu Tyr Lys Tyr Phe Asp Lys Glu<br>             180                   185                190 | 576 |
| ttt act gat att tta gcc aaa gat tat gaa gct cat ggt gtt aac ctg<br>Phe Thr Asp Ile Leu Ala Lys Asp Tyr Glu Ala His Gly Val Asn Leu<br>             195                   200                205 | 624 |
| gtt ctt ggt tca aaa gta gct gct ttt gaa gaa gtc gat gat gaa att<br>Val Leu Gly Ser Lys Val Ala Ala Phe Glu Glu Val Asp Asp Glu Ile<br>     210                   215                   220 | 672 |
| atc act aaa acc cta gat ggt aaa gaa att aaa tct gat att gca att<br>Ile Thr Lys Thr Leu Asp Gly Lys Glu Ile Lys Ser Asp Ile Ala Ile<br>225                   230                   235                240 | 720 |
| ctt tgt atc ggt ttc cgc cct aac act gaa tta ctt aaa ggt aaa gtt<br>Leu Cys Ile Gly Phe Arg Pro Asn Thr Glu Leu Leu Lys Gly Lys Val<br>               245                   250                255 | 768 |
| gcc atg ttg gat aac ggt gca atc att act gat gaa tac atg cat tca<br>Ala Met Leu Asp Asn Gly Ala Ile Ile Thr Asp Glu Tyr Met His Ser<br>             260                   265                270 | 816 |
| tca aat cgc gac att ttt gct gct ggt gat agt gcc gcc gtt cac tac<br>Ser Asn Arg Asp Ile Phe Ala Ala Gly Asp Ser Ala Ala Val His Tyr<br>             275                   280                285 | 864 |
| aac ccc act aat tct aac gcc tac att cct tta gct acc aac gcc gta<br>Asn Pro Thr Asn Ser Asn Ala Tyr Ile Pro Leu Ala Thr Asn Ala Val<br>             290                   295                300 | 912 |
| cgc caa ggg aga tta gtt ggc cta aat ctg act gaa gac aaa gta aaa<br>Arg Gln Gly Arg Leu Val Gly Leu Asn Leu Thr Glu Asp Lys Val Lys<br>305                   310                   315                320 | 960 |
| gac atg gga acc caa tct tca tct ggt ctt aaa cta tac ggt cgg act<br>Asp Met Gly Thr Gln Ser Ser Ser Gly Leu Lys Leu Tyr Gly Arg Thr<br>               325                   330                335 | 1008 |
| tat gtc tca act gga atc aat acg gct ctt gct aaa gcc aat aat tta<br>Tyr Val Ser Thr Gly Ile Asn Thr Ala Leu Ala Lys Ala Asn Asn Leu<br>             340                   345                350 | 1056 |
| aaa gtt agc gaa gta atc ata gct gat aat tat cgt cca gaa ttt atg<br>Lys Val Ser Glu Val Ile Ile Ala Asp Asn Tyr Arg Pro Glu Phe Met<br>             355                   360                365 | 1104 |
| tta tca acg gat gaa gtt tta atg tca tta gtg tat gat cct aag act<br>Leu Ser Thr Asp Glu Val Leu Met Ser Leu Val Tyr Asp Pro Lys Thr<br>370                   375                   380 | 1152 |
| cgt gta att ttg gga ggg gcg ctt tca agt atg cac gat gtt tcg caa<br>Arg Val Ile Leu Gly Gly Ala Leu Ser Ser Met His Asp Val Ser Gln<br>385                   390                   395                400 | 1200 |

```
                                                                          -continued tca gcg aac gtc tta tca gta tgt att caa aat aaa aac acg att gac          1248
Ser Ala Asn Val Leu Ser Val Cys Ile Gln Asn Lys Asn Thr Ile Asp
            405                 410                 415 gat tta gca atg gtg gat atg tta ttc caa cca caa ttt gat cgt ccg          1296
Asp Leu Ala Met Val Asp Met Leu Phe Gln Pro Gln Phe Asp Arg Pro
        420                 425                 430 ttt aac tac tta aac att cta ggc caa gct gct caa gca caa gct gac          1344
Phe Asn Tyr Leu Asn Ile Leu Gly Gln Ala Ala Gln Ala Gln Ala Asp
    435                 440                 445 aaa gca cat aaa taa                                                       1359
Lys Ala His Lys
    450

<210> SEQ ID NO 2
<211> LENGTH: 452
<212> TYPE: PRT
<213> ORGANISM: Artificial Sequence
<220> FEATURE:
<223> OTHER INFORMATION: Synthetic

<400> SEQUENCE: 2

Met Lys Val Ile Val Gly Cys Thr His Ala Gly Thr Phe Ala Val
1               5                   10                  15

Lys Gln Thr Ile Ala Asp His Pro Asp Ala Asp Val Thr Ala Tyr Glu
            20                  25                  30

Met Asn Asp Asn Ile Ser Phe Leu Ser Cys Gly Ile Ala Leu Tyr Leu
        35                  40                  45

Gly Lys Glu Ile Lys Asn Asn Asp Pro Arg Gly Leu Phe Tyr Ser Ser
    50                  55                  60

Pro Glu Glu Leu Ser Asn Leu Gly Ala Asn Val Gln Met Arg His Gln
65                  70                  75                  80

Val Thr Asn Val Asp Pro Glu Thr Lys Thr Ile Lys Val Lys Asp Leu
                85                  90                  95

Ile Thr Asn Glu Glu Lys Thr Glu Ala Tyr Asp Lys Leu Ile Met Thr
            100                 105                 110

Thr Gly Ser Lys Pro Thr Val Pro Pro Ile Pro Gly Ile Asp Ser Ser
        115                 120                 125

Arg Val Tyr Leu Cys Lys Asn Tyr Asn Asp Ala Lys Lys Leu Phe Glu
    130                 135                 140

Glu Ala Pro Lys Ala Lys Thr Ile Thr Ile Ile Gly Ser Gly Tyr Ile
145                 150                 155                 160

Gly Ala Glu Leu Ala Glu Ala Tyr Ser Asn Gln Asn Tyr Asn Val Asn
                165                 170                 175

Leu Ile Asp Gly His Glu Arg Val Leu Tyr Lys Tyr Phe Asp Lys Glu
            180                 185                 190

Phe Thr Asp Ile Leu Ala Lys Asp Tyr Glu Ala His Gly Val Asn Leu
        195                 200                 205

Val Leu Gly Ser Lys Val Ala Ala Phe Glu Glu Val Asp Asp Glu Ile
    210                 215                 220

Ile Thr Lys Thr Leu Asp Gly Lys Glu Ile Lys Ser Asp Ile Ala Ile
225                 230                 235                 240

Leu Cys Ile Gly Phe Arg Pro Asn Thr Glu Leu Leu Lys Gly Lys Val
                245                 250                 255

Ala Met Leu Asp Asn Gly Ala Ile Ile Thr Asp Glu Tyr Met His Ser
            260                 265                 270

Ser Asn Arg Asp Ile Phe Ala Ala Gly Asp Ser Ala Ala Val His Tyr
        275                 280                 285
```

```
Asn Pro Thr Asn Ser Asn Ala Tyr Ile Pro Leu Ala Thr Asn Ala Val
    290                 295                 300

Arg Gln Gly Arg Leu Val Gly Leu Asn Leu Thr Glu Asp Lys Val Lys
305                 310                 315                 320

Asp Met Gly Thr Gln Ser Ser Ser Gly Leu Lys Leu Tyr Gly Arg Thr
                325                 330                 335

Tyr Val Ser Thr Gly Ile Asn Thr Ala Leu Ala Lys Ala Asn Asn Leu
            340                 345                 350

Lys Val Ser Glu Val Ile Ala Asp Asn Tyr Arg Pro Glu Phe Met
        355                 360                 365

Leu Ser Thr Asp Glu Val Leu Met Ser Leu Val Tyr Asp Pro Lys Thr
    370                 375                 380

Arg Val Ile Leu Gly Gly Ala Leu Ser Ser Met His Asp Val Ser Gln
385                 390                 395                 400

Ser Ala Asn Val Leu Ser Val Cys Ile Gln Asn Lys Asn Thr Ile Asp
                405                 410                 415

Asp Leu Ala Met Val Asp Met Leu Phe Gln Pro Gln Phe Asp Arg Pro
            420                 425                 430

Phe Asn Tyr Leu Asn Ile Leu Gly Gln Ala Ala Gln Ala Gln Ala Asp
        435                 440                 445

Lys Ala His Lys
    450

<210> SEQ ID NO 3
<211> LENGTH: 1359
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1359)

<400> SEQUENCE: 3 atg aaa gtt att gta gta ggt tgt act cac gct ggc act ttt gca gtt      48
Met Lys Val Ile Val Val Gly Cys Thr His Ala Gly Thr Phe Ala Val
1               5                   10                  15 aag caa acg att gcc gat cac ccc gat gca gat gtg act gta tat gaa      96
Lys Gln Thr Ile Ala Asp His Pro Asp Ala Asp Val Thr Val Tyr Glu
                20                  25                  30 atg aat gat aac att tcc ttt tta tca tgt gga atc gcc ctt tac tta     144
Met Asn Asp Asn Ile Ser Phe Leu Ser Cys Gly Ile Ala Leu Tyr Leu
            35                  40                  45 ggt aaa gaa att aaa aac aat gat ccc cga ggg ctt ttc tac tca agt     192
Gly Lys Glu Ile Lys Asn Asn Asp Pro Arg Gly Leu Phe Tyr Ser Ser
        50                  55                  60 cca gaa gaa tta agc aat ctt gga gct aac gtc caa atg cgt cat caa     240
Pro Glu Glu Leu Ser Asn Leu Gly Ala Asn Val Gln Met Arg His Gln
65                  70                  75                  80 gtt aca aac gtt gat cca gaa aca aaa aca atc aaa gtt aaa gat tta     288
Val Thr Asn Val Asp Pro Glu Thr Lys Thr Ile Lys Val Lys Asp Leu
                85                  90                  95 atc acc aac gaa gaa aaa aca gaa gca tat gac aaa tta att atg acc     336
Ile Thr Asn Glu Glu Lys Thr Glu Ala Tyr Asp Lys Leu Ile Met Thr
            100                 105                 110 act ggc tct aag cct act gtt cct cca atc cct gga atc gat agt agt     384
Thr Gly Ser Lys Pro Thr Val Pro Pro Ile Pro Gly Ile Asp Ser Ser
        115                 120                 125
```

```
cgc gtt tac ctt tgt aaa aac tat aac gat gct aaa aag tta ttt gaa     432
Arg Val Tyr Leu Cys Lys Asn Tyr Asn Asp Ala Lys Lys Leu Phe Glu
    130                 135                 140 gaa gct ccc aaa gct aaa acg att act atc att ggt tcc ggt tat att     480
Glu Ala Pro Lys Ala Lys Thr Ile Thr Ile Ile Gly Ser Gly Tyr Ile
145                 150                 155                 160 ggt gcc gaa ctg gct gaa gcc tac tca aac caa aat tat aac gtt aat     528
Gly Ala Glu Leu Ala Glu Ala Tyr Ser Asn Gln Asn Tyr Asn Val Asn
                165                 170                 175 tta att gat ggt cat gaa cga gtt ctt tac aag tat ttt gat aaa gaa     576
Leu Ile Asp Gly His Glu Arg Val Leu Tyr Lys Tyr Phe Asp Lys Glu
            180                 185                 190 ttt act gat att tta gcc aaa gat tat gaa gct cat ggt gtt aac ctg     624
Phe Thr Asp Ile Leu Ala Lys Asp Tyr Glu Ala His Gly Val Asn Leu
        195                 200                 205 gtt ctt ggt tca aaa gta gct gct ttt gaa gaa gtc gat gat gaa att     672
Val Leu Gly Ser Lys Val Ala Ala Phe Glu Glu Val Asp Asp Glu Ile
    210                 215                 220 atc act aaa acc cta gat ggt aaa gaa att aaa tct gat att gca att     720
Ile Thr Lys Thr Leu Asp Gly Lys Glu Ile Lys Ser Asp Ile Ala Ile
225                 230                 235                 240 ctt tgt atc ggt ttc cgc cct aac act gaa tta ctt aaa ggt aaa gtt     768
Leu Cys Ile Gly Phe Arg Pro Asn Thr Glu Leu Leu Lys Gly Lys Val
                245                 250                 255 gcc atg ttg gat aac ggt gca atc att act gat gaa tac atg cat tca     816
Ala Met Leu Asp Asn Gly Ala Ile Ile Thr Asp Glu Tyr Met His Ser
                260                 265                 270 tca aat cgc gac att ttt gct gct ggt gat agt gcc gcc gtt cac tac     864
Ser Asn Arg Asp Ile Phe Ala Ala Gly Asp Ser Ala Ala Val His Tyr
            275                 280                 285 aac ccc act aat tct aac gcc tac att cct tta gct acc aac gcc gta     912
Asn Pro Thr Asn Ser Asn Ala Tyr Ile Pro Leu Ala Thr Asn Ala Val
        290                 295                 300 cgc caa ggg aga tta gtt ggc cta aat ctg act gaa gac aaa gta aaa     960
Arg Gln Gly Arg Leu Val Gly Leu Asn Leu Thr Glu Asp Lys Val Lys
305                 310                 315                 320 gac atg gga acc caa tct tca tct ggt ctt aaa cta tac ggt cgg act    1008
Asp Met Gly Thr Gln Ser Ser Ser Gly Leu Lys Leu Tyr Gly Arg Thr
                325                 330                 335 tat gtc tca act gga atc aat acg gct ctt gct aaa gcc aat aat tta    1056
Tyr Val Ser Thr Gly Ile Asn Thr Ala Leu Ala Lys Ala Asn Asn Leu
                340                 345                 350 aaa gtt agc gaa gta atc ata gct gat aat tat cgt cca gaa ttt atg    1104
Lys Val Ser Glu Val Ile Ile Ala Asp Asn Tyr Arg Pro Glu Phe Met
            355                 360                 365 tta tca acg gat gaa gtt tta atg tca tta gtg tat gat cct aag act    1152
Leu Ser Thr Asp Glu Val Leu Met Ser Leu Val Tyr Asp Pro Lys Thr
        370                 375                 380 cgt gta att ttg gga ggg gcg ctt tca agt atg cac gat gtt tcg caa    1200
Arg Val Ile Leu Gly Gly Ala Leu Ser Ser Met His Asp Val Ser Gln
385                 390                 395                 400 tca gcg aac gtc tta tca gta tgt att caa aat aaa aac acg att gac    1248
Ser Ala Asn Val Leu Ser Val Cys Ile Gln Asn Lys Asn Thr Ile Asp
                405                 410                 415 gat tta gca atg gtg gat atg tta ttc caa cca caa ttt gat cgt ccg    1296
Asp Leu Ala Met Val Asp Met Leu Phe Gln Pro Gln Phe Asp Arg Pro
            420                 425                 430 ttt aac tac tta aac att cta ggc caa gct gct caa gca caa gct gac    1344
Phe Asn Tyr Leu Asn Ile Leu Gly Gln Ala Ala Gln Ala Gln Ala Asp
        435                 440                 445
```

```
aaa gca cat aaa taa                                              1359
Lys Ala His Lys
    450

<210> SEQ ID NO 4
<211> LENGTH: 452
<212> TYPE: PRT
<213> ORGANISM: Artificial Sequence
<220> FEATURE:
<223> OTHER INFORMATION: Synthetic

<400> SEQUENCE: 4

Met Lys Val Ile Val Gly Cys Thr His Ala Gly Thr Phe Ala Val
1               5                   10                  15

Lys Gln Thr Ile Ala Asp His Pro Asp Ala Asp Val Thr Val Tyr Glu
            20                  25                  30

Met Asn Asp Asn Ile Ser Phe Leu Ser Cys Gly Ile Ala Leu Tyr Leu
        35                  40                  45

Gly Lys Glu Ile Lys Asn Asn Asp Pro Arg Gly Leu Phe Tyr Ser Ser
    50                  55                  60

Pro Glu Glu Leu Ser Asn Leu Gly Ala Asn Val Gln Met Arg His Gln
65                  70                  75                  80

Val Thr Asn Val Asp Pro Glu Thr Lys Thr Ile Lys Val Lys Asp Leu
                85                  90                  95

Ile Thr Asn Glu Glu Lys Thr Glu Ala Tyr Asp Lys Leu Ile Met Thr
            100                 105                 110

Thr Gly Ser Lys Pro Thr Val Pro Pro Ile Pro Gly Ile Asp Ser Ser
        115                 120                 125

Arg Val Tyr Leu Cys Lys Asn Tyr Asn Asp Ala Lys Lys Leu Phe Glu
    130                 135                 140

Glu Ala Pro Lys Ala Lys Thr Ile Thr Ile Ile Gly Ser Gly Tyr Ile
145                 150                 155                 160

Gly Ala Glu Leu Ala Glu Ala Tyr Ser Asn Gln Asn Tyr Asn Val Asn
                165                 170                 175

Leu Ile Asp Gly His Glu Arg Val Leu Tyr Lys Tyr Phe Asp Lys Glu
            180                 185                 190

Phe Thr Asp Ile Leu Ala Lys Asp Tyr Glu Ala His Gly Val Asn Leu
        195                 200                 205

Val Leu Gly Ser Lys Val Ala Ala Phe Glu Glu Val Asp Asp Glu Ile
    210                 215                 220

Ile Thr Lys Thr Leu Asp Gly Lys Glu Ile Lys Ser Asp Ile Ala Ile
225                 230                 235                 240

Leu Cys Ile Gly Phe Arg Pro Asn Thr Glu Leu Leu Lys Gly Lys Val
                245                 250                 255

Ala Met Leu Asp Asn Gly Ala Ile Ile Thr Asp Glu Tyr Met His Ser
            260                 265                 270

Ser Asn Arg Asp Ile Phe Ala Ala Gly Asp Ser Ala Ala Val His Tyr
        275                 280                 285

Asn Pro Thr Asn Ser Asn Ala Tyr Ile Pro Leu Ala Thr Asn Ala Val
    290                 295                 300

Arg Gln Gly Arg Leu Val Gly Leu Asn Leu Thr Glu Asp Lys Val Lys
305                 310                 315                 320

Asp Met Gly Thr Gln Ser Ser Ser Gly Leu Lys Leu Tyr Gly Arg Thr
                325                 330                 335

Tyr Val Ser Thr Gly Ile Asn Thr Ala Leu Ala Lys Ala Asn Asn Leu
```

```
                    340                 345                 350
Lys Val Ser Glu Val Ile Ile Ala Asp Asn Tyr Arg Pro Glu Phe Met
            355                 360                 365

Leu Ser Thr Asp Glu Val Leu Met Ser Leu Val Tyr Asp Pro Lys Thr
    370                 375                 380

Arg Val Ile Leu Gly Gly Ala Leu Ser Ser Met His Asp Val Ser Gln
385                 390                 395                 400

Ser Ala Asn Val Leu Ser Val Cys Ile Gln Asn Lys Asn Thr Ile Asp
                405                 410                 415

Asp Leu Ala Met Val Asp Met Leu Phe Gln Pro Gln Phe Asp Arg Pro
            420                 425                 430

Phe Asn Tyr Leu Asn Ile Leu Gly Gln Ala Ala Gln Ala Gln Ala Asp
            435                 440                 445

Lys Ala His Lys
    450

<210> SEQ ID NO 5
<211> LENGTH: 1359
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1359)

<400> SEQUENCE: 5 atg aaa gtt att gta gta ggt tgt act cac gct ggc act ttt gca gtt        48
Met Lys Val Ile Val Val Gly Cys Thr His Ala Gly Thr Phe Ala Val
1               5                   10                  15 aag caa acg att gcc gat cac ccc gat gca gat gtg act gta tat gaa        96
Lys Gln Thr Ile Ala Asp His Pro Asp Ala Asp Val Thr Val Tyr Glu
            20                  25                  30 atg aat gat aac att tcc ttt tta tca tgt gga atc gcc ctt tac tta       144
Met Asn Asp Asn Ile Ser Phe Leu Ser Cys Gly Ile Ala Leu Tyr Leu
        35                  40                  45 ggt aaa gaa att aaa aac aat gat ccc cga ggg ctt ttc tac tca agt       192
Gly Lys Glu Ile Lys Asn Asn Asp Pro Arg Gly Leu Phe Tyr Ser Ser
    50                  55                  60 cca gaa gaa tta agc aat ctt gga gct aac gtc caa atg cgt cat caa       240
Pro Glu Glu Leu Ser Asn Leu Gly Ala Asn Val Gln Met Arg His Gln
65                  70                  75                  80 gtt aca aac gtt gat cca gaa aca aaa aca atc aaa gtt aaa gat tta       288
Val Thr Asn Val Asp Pro Glu Thr Lys Thr Ile Lys Val Lys Asp Leu
                85                  90                  95 atc acc aac gaa gaa aga aca gaa gca tat gac aaa tta att atg acc       336
Ile Thr Asn Glu Glu Arg Thr Glu Ala Tyr Asp Lys Leu Ile Met Thr
            100                 105                 110 act ggt tct aag cct act gtt cct cca atc cct gga atc gat agt agt       384
Thr Gly Ser Lys Pro Thr Val Pro Pro Ile Pro Gly Ile Asp Ser Ser
        115                 120                 125 cgc gtt tac ctt tgt aaa aac tat aac gat gct aaa aag tta ttt gaa       432
Arg Val Tyr Leu Cys Lys Asn Tyr Asn Asp Ala Lys Lys Leu Phe Glu
    130                 135                 140 gaa gct ccc aaa gct aaa acg att act atc att ggt tct ggt tat att       480
Glu Ala Pro Lys Ala Lys Thr Ile Thr Ile Ile Gly Ser Gly Tyr Ile
145                 150                 155                 160 ggt gcc gaa ctg gct gaa gcc tac tca aac caa aat tat aac gtt aat       528
Gly Ala Glu Leu Ala Glu Ala Tyr Ser Asn Gln Asn Tyr Asn Val Asn
                165                 170                 175
```

```
tta att gat ggt cat gaa cga gtt ctt tac aag tat ttt gat aaa gaa      576
Leu Ile Asp Gly His Glu Arg Val Leu Tyr Lys Tyr Phe Asp Lys Glu
        180                 185                 190 ttt act gat att tta gcc aaa gat tat gaa gct cat ggt gtt aac ctg      624
Phe Thr Asp Ile Leu Ala Lys Asp Tyr Glu Ala His Gly Val Asn Leu
    195                 200                 205 gtt ctt ggt tca aaa gta gct gct ttt gaa gaa gtc gat gat gaa att      672
Val Leu Gly Ser Lys Val Ala Ala Phe Glu Glu Val Asp Asp Glu Ile
210                 215                 220 atc act aaa acc cta gat ggt aaa gaa att aaa tct gat att gca att      720
Ile Thr Lys Thr Leu Asp Gly Lys Glu Ile Lys Ser Asp Ile Ala Ile
225                 230                 235                 240 ctt tgt atc ggt ttc cgc cct aac act gga tta ctt aaa ggt aaa gtt      768
Leu Cys Ile Gly Phe Arg Pro Asn Thr Gly Leu Leu Lys Gly Lys Val
                245                 250                 255 gcc atg ttg gat aac ggt gca atc att act gat gaa tac atg cat tca      816
Ala Met Leu Asp Asn Gly Ala Ile Ile Thr Asp Glu Tyr Met His Ser
            260                 265                 270 tca aat cgc gac att ttt gct gct ggt gat agt gcc gcc gtt cac tac      864
Ser Asn Arg Asp Ile Phe Ala Ala Gly Asp Ser Ala Ala Val His Tyr
        275                 280                 285 aac ccc act aat tct aac gcc tac att cct tta gct acc aac gcc gta      912
Asn Pro Thr Asn Ser Asn Ala Tyr Ile Pro Leu Ala Thr Asn Ala Val
    290                 295                 300 cgc caa ggg aga tta gtt ggc cta aat ctg act gaa gac aaa gta aaa      960
Arg Gln Gly Arg Leu Val Gly Leu Asn Leu Thr Glu Asp Lys Val Lys
305                 310                 315                 320 gac atg gga acc caa tcc tca tct ggt ctt aaa cta tac ggt cgg act     1008
Asp Met Gly Thr Gln Ser Ser Ser Gly Leu Lys Leu Tyr Gly Arg Thr
                325                 330                 335 tat gtc tca act gga atc aat acg gct ctt gct aaa gcc aat aat tta     1056
Tyr Val Ser Thr Gly Ile Asn Thr Ala Leu Ala Lys Ala Asn Asn Leu
            340                 345                 350 aaa gtt agc gaa gta atc ata gct gat aat tat cgt cca gaa ttt atg     1104
Lys Val Ser Glu Val Ile Ile Ala Asp Asn Tyr Arg Pro Glu Phe Met
        355                 360                 365 tta tca acg gat gaa gtt tta atg tca tta gtg tat gat cct aag act     1152
Leu Ser Thr Asp Glu Val Leu Met Ser Leu Val Tyr Asp Pro Lys Thr
    370                 375                 380 cgt gta att ttg gga ggg gcg ctt tca agt atg cac gat gtt tcg caa     1200
Arg Val Ile Leu Gly Gly Ala Leu Ser Ser Met His Asp Val Ser Gln
385                 390                 395                 400 tca gcg aac gtc tta tca gta tgt att caa aat aaa aac acg att gac     1248
Ser Ala Asn Val Leu Ser Val Cys Ile Gln Asn Lys Asn Thr Ile Asp
                405                 410                 415 gat tta gca atg gtg gat atg tta ttc caa cca caa ttt gat cgt ccg     1296
Asp Leu Ala Met Val Asp Met Leu Phe Gln Pro Gln Phe Asp Arg Pro
            420                 425                 430 ttt aac tac tta aac att cta ggc caa gct gct caa gca caa gct gac     1344
Phe Asn Tyr Leu Asn Ile Leu Gly Gln Ala Ala Gln Ala Gln Ala Asp
        435                 440                 445 aaa gca cat aaa taa                                                 1359
Lys Ala His Lys
450

<210> SEQ ID NO 6
<211> LENGTH: 452
<212> TYPE: PRT
<213> ORGANISM: Artificial Sequence
<220> FEATURE:
```

<223> OTHER INFORMATION: Synthetic

<400> SEQUENCE: 6

```
Met Lys Val Ile Val Gly Cys Thr His Ala Gly Thr Phe Ala Val
1               5                  10                  15

Lys Gln Thr Ile Ala Asp His Pro Asp Ala Asp Val Thr Val Tyr Glu
            20                  25                  30

Met Asn Asp Asn Ile Ser Phe Leu Ser Cys Gly Ile Ala Leu Tyr Leu
        35                  40                  45

Gly Lys Glu Ile Lys Asn Asn Asp Pro Arg Gly Leu Phe Tyr Ser Ser
50                  55                  60

Pro Glu Glu Leu Ser Asn Leu Gly Ala Asn Val Gln Met Arg His Gln
65                  70                  75                  80

Val Thr Asn Val Asp Pro Glu Thr Lys Thr Ile Lys Val Lys Asp Leu
                85                  90                  95

Ile Thr Asn Glu Glu Arg Thr Glu Ala Tyr Asp Lys Leu Ile Met Thr
            100                 105                 110

Thr Gly Ser Lys Pro Thr Val Pro Pro Ile Pro Gly Ile Asp Ser Ser
        115                 120                 125

Arg Val Tyr Leu Cys Lys Asn Tyr Asn Asp Ala Lys Lys Leu Phe Glu
    130                 135                 140

Glu Ala Pro Lys Ala Lys Thr Ile Thr Ile Ile Gly Ser Gly Tyr Ile
145                 150                 155                 160

Gly Ala Glu Leu Ala Glu Ala Tyr Ser Asn Gln Asn Tyr Asn Val Asn
                165                 170                 175

Leu Ile Asp Gly His Glu Arg Val Leu Tyr Lys Tyr Phe Asp Lys Glu
            180                 185                 190

Phe Thr Asp Ile Leu Ala Lys Asp Tyr Glu Ala His Gly Val Asn Leu
        195                 200                 205

Val Leu Gly Ser Lys Val Ala Ala Phe Glu Glu Val Asp Asp Glu Ile
    210                 215                 220

Ile Thr Lys Thr Leu Asp Gly Lys Glu Ile Lys Ser Asp Ile Ala Ile
225                 230                 235                 240

Leu Cys Ile Gly Phe Arg Pro Asn Thr Gly Leu Leu Lys Gly Lys Val
                245                 250                 255

Ala Met Leu Asp Asn Gly Ala Ile Ile Thr Asp Glu Tyr Met His Ser
            260                 265                 270

Ser Asn Arg Asp Ile Phe Ala Ala Gly Asp Ser Ala Ala Val His Tyr
        275                 280                 285

Asn Pro Thr Asn Ser Asn Ala Tyr Ile Pro Leu Ala Thr Asn Ala Val
    290                 295                 300

Arg Gln Gly Arg Leu Val Gly Leu Asn Leu Thr Glu Asp Lys Val Lys
305                 310                 315                 320

Asp Met Gly Thr Gln Ser Ser Gly Leu Lys Leu Tyr Gly Arg Thr
                325                 330                 335

Tyr Val Ser Thr Gly Ile Asn Thr Ala Leu Ala Lys Ala Asn Asn Leu
            340                 345                 350

Lys Val Ser Glu Val Ile Ile Ala Asp Asn Tyr Arg Pro Glu Phe Met
        355                 360                 365

Leu Ser Thr Asp Glu Val Leu Met Ser Leu Val Tyr Asp Pro Lys Thr
    370                 375                 380

Arg Val Ile Leu Gly Gly Ala Leu Ser Ser Met His Asp Val Ser Gln
385                 390                 395                 400
```

```
Ser Ala Asn Val Leu Ser Val Cys Ile Gln Asn Lys Asn Thr Ile Asp
                405                 410                 415

Asp Leu Ala Met Val Asp Met Leu Phe Gln Pro Gln Phe Asp Arg Pro
            420                 425                 430

Phe Asn Tyr Leu Asn Ile Leu Gly Gln Ala Ala Gln Ala Gln Ala Asp
                435                 440                 445

Lys Ala His Lys
    450

<210> SEQ ID NO 7
<211> LENGTH: 1335
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1335)

<400> SEQUENCE: 7 atg atg aaa ata ata att att ggg ggc aca tca gca gga act agt gcc        48
Met Met Lys Ile Ile Ile Ile Gly Gly Thr Ser Ala Gly Thr Ser Ala
1               5                   10                  15 gca gct aaa gca aac cgc tta aac aaa aag cta gac att act atc tat       96
Ala Ala Lys Ala Asn Arg Leu Asn Lys Lys Leu Asp Ile Thr Ile Tyr
                20                  25                  30 gaa aaa aca aat att gta tct ttt gga acc tgt ggc ctg cct tac ttt      144
Glu Lys Thr Asn Ile Val Ser Phe Gly Thr Cys Gly Leu Pro Tyr Phe
            35                  40                  45 gtg ggg gga ttc ttt gac aac ccc aat aca atg atc tca aga aca caa      192
Val Gly Gly Phe Phe Asp Asn Pro Asn Thr Met Ile Ser Arg Thr Gln
        50                  55                  60 gaa gaa ttc gaa aaa act gga atc tct gtt aaa act aac cac gaa gtt      240
Glu Glu Phe Glu Lys Thr Gly Ile Ser Val Lys Thr Asn His Glu Val
65                  70                  75                  80 atc aaa gta gat gca aaa aac aat aca att gta ata aaa aat caa aaa      288
Ile Lys Val Asp Ala Lys Asn Asn Thr Ile Val Ile Lys Asn Gln Lys
                85                  90                  95 aca gga acc att ttt aac aat act tac gat caa ctt atg ata gca act      336
Thr Gly Thr Ile Phe Asn Asn Thr Tyr Asp Gln Leu Met Ile Ala Thr
            100                 105                 110 ggt gca aaa cct att att cca cca atc aat aat atc aat cta gaa aat      384
Gly Ala Lys Pro Ile Ile Pro Pro Ile Asn Asn Ile Asn Leu Glu Asn
        115                 120                 125 ttt cat act ctg aaa aat tta gaa gac ggt caa aaa ata aaa aaa tta      432
Phe His Thr Leu Lys Asn Leu Glu Asp Gly Gln Lys Ile Lys Lys Leu
    130                 135                 140 atg gat aga gaa gag att aaa aat ata gtg ata att ggt ggt gga tac      480
Met Asp Arg Glu Glu Ile Lys Asn Ile Val Ile Ile Gly Gly Gly Tyr
145                 150                 155                 160 att gga att gaa atg gta gaa gca gca aaa aat aaa aga aaa aat gta      528
Ile Gly Ile Glu Met Val Glu Ala Ala Lys Asn Lys Arg Lys Asn Val
                165                 170                 175 aga tta att caa cta gat aag cac ata ctc ata gat tcc ttt gac gaa      576
Arg Leu Ile Gln Leu Asp Lys His Ile Leu Ile Asp Ser Phe Asp Glu
            180                 185                 190 gaa ata gtc aca ata atg gaa gaa gaa cta aca aaa aag ggg gtt aat      624
Glu Ile Val Thr Ile Met Glu Glu Glu Leu Thr Lys Lys Gly Val Asn
        195                 200                 205 ctt cat aca aat gag ttt gta aaa agt tta ata gga gaa aaa aag gca      672
Leu His Thr Asn Glu Phe Val Lys Ser Leu Ile Gly Glu Lys Lys Ala
```

```
                    210                 215                 220
gaa gga gta gta aca aac aaa aat act tat caa gct gac gct gtt ata    720
Glu Gly Val Val Thr Asn Lys Asn Thr Tyr Gln Ala Asp Ala Val Ile
225                 230                 235                 240 ctt gct acc gga ata aaa cct gac act gaa ttt tta gaa aac cag ctt    768
Leu Ala Thr Gly Ile Lys Pro Asp Thr Glu Phe Leu Glu Asn Gln Leu
                245                 250                 255 aaa act act aaa aat gga gca ata att gta aat gag tat ggc gaa act    816
Lys Thr Thr Lys Asn Gly Ala Ile Ile Val Asn Glu Tyr Gly Glu Thr
            260                 265                 270 agc ata aaa aat att ttt tct gca gga gat tgt gca act att tat aat    864
Ser Ile Lys Asn Ile Phe Ser Ala Gly Asp Cys Ala Thr Ile Tyr Asn
        275                 280                 285 ata gta agt aaa aaa aat gaa tac ata ccc ttg gca aca aca gcc aac    912
Ile Val Ser Lys Lys Asn Glu Tyr Ile Pro Leu Ala Thr Thr Ala Asn
    290                 295                 300 aaa ctt gga aga ata gtt ggt gaa aat tta gct ggg aat cat aca gca    960
Lys Leu Gly Arg Ile Val Gly Glu Asn Leu Ala Gly Asn His Thr Ala
305                 310                 315                 320 ttt aaa ggc aca ttg ggc tca gct tca att aaa ata cta tct tta gaa   1008
Phe Lys Gly Thr Leu Gly Ser Ala Ser Ile Lys Ile Leu Ser Leu Glu
                325                 330                 335 gct gca aga aca gga ctt aca gaa aaa gat gca aaa aag ctc caa ata   1056
Ala Ala Arg Thr Gly Leu Thr Glu Lys Asp Ala Lys Lys Leu Gln Ile
            340                 345                 350 aaa tat aaa acg att ttt gta aag gac aaa aat cat aca aat tat tat   1104
Lys Tyr Lys Thr Ile Phe Val Lys Asp Lys Asn His Thr Asn Tyr Tyr
        355                 360                 365 cca ggc caa gaa gat ctt tat att aaa tta att tat gag gaa aat acc   1152
Pro Gly Gln Glu Asp Leu Tyr Ile Lys Leu Ile Tyr Glu Glu Asn Thr
    370                 375                 380 aaa ata atc ctt ggg gca caa gca ata gga aaa aat gga gcc gta ata   1200
Lys Ile Ile Leu Gly Ala Gln Ala Ile Gly Lys Asn Gly Ala Val Ile
385                 390                 395                 400 aga att cat gct tta tca att gca atc tat tca aaa ctt aca aca aaa   1248
Arg Ile His Ala Leu Ser Ile Ala Ile Tyr Ser Lys Leu Thr Thr Lys
                405                 410                 415 gag cta ggg atg atg gat ttc tca tat tcc cca ccc ttc tca aga act   1296
Glu Leu Gly Met Met Asp Phe Ser Tyr Ser Pro Pro Phe Ser Arg Thr
            420                 425                 430 tgg gat ata tta aat att gct ggc aat gct gcc aaa tag              1335
Trp Asp Ile Leu Asn Ile Ala Gly Asn Ala Ala Lys
        435                 440

<210> SEQ ID NO 8
<211> LENGTH: 444
<212> TYPE: PRT
<213> ORGANISM: Artificial Sequence
<220> FEATURE:
<223> OTHER INFORMATION: Synthetic

<400> SEQUENCE: 8

Met Met Lys Ile Ile Ile Gly Gly Thr Ser Ala Gly Thr Ser Ala
1               5                   10                  15

Ala Ala Lys Ala Asn Arg Leu Asn Lys Lys Leu Asp Ile Thr Ile Tyr
            20                  25                  30

Glu Lys Thr Asn Ile Val Ser Phe Gly Thr Cys Gly Leu Pro Tyr Phe
        35                  40                  45

Val Gly Gly Phe Phe Asp Asn Pro Asn Thr Met Ile Ser Arg Thr Gln
    50                  55                  60
```

```
Glu Glu Phe Glu Lys Thr Gly Ile Ser Val Lys Thr Asn His Glu Val
 65                  70                  75                  80

Ile Lys Val Asp Ala Lys Asn Asn Thr Ile Val Ile Lys Asn Gln Lys
                 85                  90                  95

Thr Gly Thr Ile Phe Asn Asn Thr Tyr Asp Gln Leu Met Ile Ala Thr
            100                 105                 110

Gly Ala Lys Pro Ile Ile Pro Pro Ile Asn Asn Ile Asn Leu Glu Asn
        115                 120                 125

Phe His Thr Leu Lys Asn Leu Glu Asp Gly Gln Lys Ile Lys Lys Leu
    130                 135                 140

Met Asp Arg Glu Glu Ile Lys Asn Ile Val Ile Gly Gly Gly Tyr
145                 150                 155                 160

Ile Gly Ile Glu Met Val Glu Ala Ala Lys Asn Lys Arg Lys Asn Val
                165                 170                 175

Arg Leu Ile Gln Leu Asp Lys His Ile Leu Ile Asp Ser Phe Asp Glu
            180                 185                 190

Glu Ile Val Thr Ile Met Glu Glu Glu Leu Thr Lys Lys Gly Val Asn
        195                 200                 205

Leu His Thr Asn Glu Phe Val Lys Ser Leu Ile Gly Glu Lys Lys Ala
    210                 215                 220

Glu Gly Val Val Thr Asn Lys Asn Thr Tyr Gln Ala Asp Ala Val Ile
225                 230                 235                 240

Leu Ala Thr Gly Ile Lys Pro Asp Thr Glu Phe Leu Glu Asn Gln Leu
                245                 250                 255

Lys Thr Thr Lys Asn Gly Ala Ile Ile Val Asn Glu Tyr Gly Glu Thr
            260                 265                 270

Ser Ile Lys Asn Ile Phe Ser Ala Gly Asp Cys Ala Thr Ile Tyr Asn
        275                 280                 285

Ile Val Ser Lys Asn Glu Tyr Ile Pro Leu Ala Thr Thr Ala Asn
    290                 295                 300

Lys Leu Gly Arg Ile Val Gly Glu Asn Leu Ala Gly Asn His Thr Ala
305                 310                 315                 320

Phe Lys Gly Thr Leu Gly Ser Ala Ser Ile Lys Ile Leu Ser Leu Glu
                325                 330                 335

Ala Ala Arg Thr Gly Leu Thr Glu Lys Asp Ala Lys Lys Leu Gln Ile
            340                 345                 350

Lys Tyr Lys Thr Ile Phe Val Lys Asp Lys Asn His Thr Asn Tyr Tyr
        355                 360                 365

Pro Gly Gln Glu Asp Leu Tyr Ile Lys Leu Ile Tyr Glu Glu Asn Thr
    370                 375                 380

Lys Ile Ile Leu Gly Ala Gln Ala Ile Gly Lys Asn Gly Ala Val Ile
385                 390                 395                 400

Arg Ile His Ala Leu Ser Ile Ala Ile Tyr Ser Lys Leu Thr Thr Lys
                405                 410                 415

Glu Leu Gly Met Met Asp Phe Ser Tyr Ser Pro Pro Phe Ser Arg Thr
            420                 425                 430

Trp Asp Ile Leu Asn Ile Ala Gly Asn Ala Ala Lys
        435                 440

<210> SEQ ID NO 9
<211> LENGTH: 1335
<212> TYPE: DNA
<213> ORGANISM: Artificial Sequence
<220> FEATURE:
```

<223> OTHER INFORMATION: Synthetic
<220> FEATURE:
<221> NAME/KEY: CDS
<222> LOCATION: (1)..(1335)

<400> SEQUENCE: 9

| | | | | | | | | | | | | | | | | |
|---|---|---|---|---|---|---|---|---|---|---|---|---|---|---|---|---|
| atg | atg | aaa | ata | ata | att | att | ggg | ggc | aca | tca | gca | gga | act | agt | gcc | 48 |
| Met | Met | Lys | Ile | Ile | Ile | Ile | Gly | Gly | Thr | Ser | Ala | Gly | Thr | Ser | Ala | |
| 1 | | | | 5 | | | | | 10 | | | | | 15 | | |

| gca | gct | aaa | gca | aac | cgc | tta | aac | aaa | aag | cta | gac | att | act | atc | tat | 96 |
|---|---|---|---|---|---|---|---|---|---|---|---|---|---|---|---|---|
| Ala | Ala | Lys | Ala | Asn | Arg | Leu | Asn | Lys | Lys | Leu | Asp | Ile | Thr | Ile | Tyr | |
| | | | 20 | | | | | 25 | | | | | 30 | | | |

| gaa | aaa | aca | aat | att | gta | tct | ttt | gga | acc | tgc | ggc | ctg | cct | tac | ttt | 144 |
|---|---|---|---|---|---|---|---|---|---|---|---|---|---|---|---|---|
| Glu | Lys | Thr | Asn | Ile | Val | Ser | Phe | Gly | Thr | Cys | Gly | Leu | Pro | Tyr | Phe | |
| | | | 35 | | | | | 40 | | | | | 45 | | | |

| gtg | ggg | gga | ttc | ttt | gac | aac | ccc | aat | aca | atg | atc | tca | aga | aca | caa | 192 |
|---|---|---|---|---|---|---|---|---|---|---|---|---|---|---|---|---|
| Val | Gly | Gly | Phe | Phe | Asp | Asn | Pro | Asn | Thr | Met | Ile | Ser | Arg | Thr | Gln | |
| | 50 | | | | | 55 | | | | | 60 | | | | | |

| gaa | gaa | ttc | gaa | aaa | act | gga | atc | tct | gtt | aaa | act | aac | cac | gaa | gct | 240 |
|---|---|---|---|---|---|---|---|---|---|---|---|---|---|---|---|---|
| Glu | Glu | Phe | Glu | Lys | Thr | Gly | Ile | Ser | Val | Lys | Thr | Asn | His | Glu | Ala | |
| 65 | | | | | 70 | | | | | 75 | | | | | 80 | |

| atc | aaa | gta | gat | gca | aaa | aac | aat | aca | att | gta | ata | aaa | aat | caa | aaa | 288 |
|---|---|---|---|---|---|---|---|---|---|---|---|---|---|---|---|---|
| Ile | Lys | Val | Asp | Ala | Lys | Asn | Asn | Thr | Ile | Val | Ile | Lys | Asn | Gln | Lys | |
| | | | | 85 | | | | | 90 | | | | | 95 | | |

| aca | gga | acc | att | ttt | aac | aat | act | tac | gat | caa | ctt | atg | ata | gca | act | 336 |
|---|---|---|---|---|---|---|---|---|---|---|---|---|---|---|---|---|
| Thr | Gly | Thr | Ile | Phe | Asn | Asn | Thr | Tyr | Asp | Gln | Leu | Met | Ile | Ala | Thr | |
| | | | 100 | | | | | 105 | | | | | 110 | | | |

| ggt | gca | aaa | cct | att | att | cca | cca | atc | aat | aat | atc | aat | cta | gaa | aat | 384 |
|---|---|---|---|---|---|---|---|---|---|---|---|---|---|---|---|---|
| Gly | Ala | Lys | Pro | Ile | Ile | Pro | Pro | Ile | Asn | Asn | Ile | Asn | Leu | Glu | Asn | |
| | | | 115 | | | | | 120 | | | | | 125 | | | |

| ttt | cat | act | ctg | aaa | aat | tta | gaa | gac | ggt | caa | aaa | ata | aaa | aaa | tta | 432 |
|---|---|---|---|---|---|---|---|---|---|---|---|---|---|---|---|---|
| Phe | His | Thr | Leu | Lys | Asn | Leu | Glu | Asp | Gly | Gln | Lys | Ile | Lys | Lys | Leu | |
| | 130 | | | | | 135 | | | | | 140 | | | | | |

| atg | gat | aga | gaa | gag | att | aaa | aat | ata | gcg | ata | att | ggt | ggt | gga | tac | 480 |
|---|---|---|---|---|---|---|---|---|---|---|---|---|---|---|---|---|
| Met | Asp | Arg | Glu | Glu | Ile | Lys | Asn | Ile | Ala | Ile | Ile | Gly | Gly | Gly | Tyr | |
| 145 | | | | | 150 | | | | | 155 | | | | | 160 | |

| att | gga | att | gaa | atg | gta | gaa | gca | gca | aaa | aat | aaa | aga | aaa | aat | gta | 528 |
|---|---|---|---|---|---|---|---|---|---|---|---|---|---|---|---|---|
| Ile | Gly | Ile | Glu | Met | Val | Glu | Ala | Ala | Lys | Asn | Lys | Arg | Lys | Asn | Val | |
| | | | | 165 | | | | | 170 | | | | | 175 | | |

| aga | tta | att | caa | cta | gat | aag | cac | ata | ctc | ata | gat | tcc | ttt | gac | gaa | 576 |
|---|---|---|---|---|---|---|---|---|---|---|---|---|---|---|---|---|
| Arg | Leu | Ile | Gln | Leu | Asp | Lys | His | Ile | Leu | Ile | Asp | Ser | Phe | Asp | Glu | |
| | | | 180 | | | | | 185 | | | | | 190 | | | |

| gaa | ata | gtc | aca | ata | atg | gaa | gaa | gaa | cta | aca | aaa | aag | ggg | gtt | aat | 624 |
|---|---|---|---|---|---|---|---|---|---|---|---|---|---|---|---|---|
| Glu | Ile | Val | Thr | Ile | Met | Glu | Glu | Glu | Leu | Thr | Lys | Lys | Gly | Val | Asn | |
| | | | 195 | | | | | 200 | | | | | 205 | | | |

| ctt | cat | aca | aat | gag | ttt | gta | aaa | agt | tta | ata | gga | gaa | aaa | aag | gca | 672 |
|---|---|---|---|---|---|---|---|---|---|---|---|---|---|---|---|---|
| Leu | His | Thr | Asn | Glu | Phe | Val | Lys | Ser | Leu | Ile | Gly | Glu | Lys | Lys | Ala | |
| | 210 | | | | | 215 | | | | | 220 | | | | | |

| gga | gga | gta | gta | aca | aac | aaa | aat | act | tat | caa | gct | gac | gct | gtt | ata | 720 |
|---|---|---|---|---|---|---|---|---|---|---|---|---|---|---|---|---|
| Gly | Gly | Val | Val | Thr | Asn | Lys | Asn | Thr | Tyr | Gln | Ala | Asp | Ala | Val | Ile | |
| 225 | | | | | 230 | | | | | 235 | | | | | 240 | |

| ctt | gct | acc | gga | ata | aaa | cct | gac | act | gaa | ttt | tta | gaa | aac | cag | ctt | 768 |
|---|---|---|---|---|---|---|---|---|---|---|---|---|---|---|---|---|
| Leu | Ala | Thr | Gly | Ile | Lys | Pro | Asp | Thr | Glu | Phe | Leu | Glu | Asn | Gln | Leu | |
| | | | | 245 | | | | | 250 | | | | | 255 | | |

| aaa | act | act | aaa | aat | gga | gca | ata | att | gta | aat | gag | tat | ggc | gaa | act | 816 |
|---|---|---|---|---|---|---|---|---|---|---|---|---|---|---|---|---|
| Lys | Thr | Thr | Lys | Asn | Gly | Ala | Ile | Ile | Val | Asn | Glu | Tyr | Gly | Glu | Thr | |
| | | | 260 | | | | | 265 | | | | | 270 | | | |

| agc | ata | aaa | aat | att | ttt | tct | gca | gga | gat | tgt | gca | act | att | tat | aat | 864 |
|---|---|---|---|---|---|---|---|---|---|---|---|---|---|---|---|---|
| Ser | Ile | Lys | Asn | Ile | Phe | Ser | Ala | Gly | Asp | Cys | Ala | Thr | Ile | Tyr | Asn | |
| | | 275 | | | | | 280 | | | | | 285 | | | | |

```
ata gta agt aaa aaa aat gaa tac ata ccc ttg gca aca aca gcc aac        912
Ile Val Ser Lys Lys Asn Glu Tyr Ile Pro Leu Ala Thr Thr Ala Asn
    290                 295                 300 aaa ctt gga aga ata gtt ggt gaa aat tta gct ggg aat cat aca gca        960
Lys Leu Gly Arg Ile Val Gly Glu Asn Leu Ala Gly Asn His Thr Ala
305                 310                 315                 320 ttt aaa ggc aca ttg ggc tca gct tca att aaa ata cta tct tta gaa      1008
Phe Lys Gly Thr Leu Gly Ser Ala Ser Ile Lys Ile Leu Ser Leu Glu
                325                 330                 335 gct gca aga acg gga ctt aca gaa aaa gat gca aaa agg ctc caa ata      1056
Ala Ala Arg Thr Gly Leu Thr Glu Lys Asp Ala Lys Arg Leu Gln Ile
            340                 345                 350 aaa tat aaa acg att ttt gta aag gac aaa aat cat aca aat tat tat      1104
Lys Tyr Lys Thr Ile Phe Val Lys Asp Lys Asn His Thr Asn Tyr Tyr
        355                 360                 365 cca ggc caa gaa gat ctt tat att aaa tta att tat gag gaa aat acc      1152
Pro Gly Gln Glu Asp Leu Tyr Ile Lys Leu Ile Tyr Glu Glu Asn Thr
370                 375                 380 aaa ata atc ctt gga gca caa gca aca gga aaa aat gga gcc gta atg      1200
Lys Ile Ile Leu Gly Ala Gln Ala Thr Gly Lys Asn Gly Ala Val Met
385                 390                 395                 400 aga att cat gct tta tca att gca atc tat tca aaa ctt aca aca aaa      1248
Arg Ile His Ala Leu Ser Ile Ala Ile Tyr Ser Lys Leu Thr Thr Lys
                405                 410                 415 gag cta agg atg atg gat ttc tca tat tcc cca ccc ttc tca aga act      1296
Glu Leu Arg Met Met Asp Phe Ser Tyr Ser Pro Pro Phe Ser Arg Thr
            420                 425                 430 tgg gat ata tta aat att gct ggc aat gct gcc aaa tag                  1335
Trp Asp Ile Leu Asn Ile Ala Gly Asn Ala Ala Lys
        435                 440

<210> SEQ ID NO 10
<211> LENGTH: 444
<212> TYPE: PRT
<213> ORGANISM: Artificial Sequence
<220> FEATURE:
<223> OTHER INFORMATION: Synthetic

<400> SEQUENCE: 10

Met Met Lys Ile Ile Ile Ile Gly Gly Thr Ser Ala Gly Thr Ser Ala
1               5                   10                  15

Ala Ala Lys Ala Asn Arg Leu Asn Lys Lys Leu Asp Ile Thr Ile Tyr
            20                  25                  30

Glu Lys Thr Asn Ile Val Ser Phe Gly Thr Cys Gly Leu Pro Tyr Phe
        35                  40                  45

Val Gly Gly Phe Phe Asp Asn Pro Asn Thr Met Ile Ser Arg Thr Gln
    50                  55                  60

Glu Glu Phe Glu Lys Thr Gly Ile Ser Val Lys Thr Asn His Glu Ala
65                  70                  75                  80

Ile Lys Val Asp Ala Lys Asn Asn Thr Ile Val Ile Lys Asn Gln Lys
                85                  90                  95

Thr Gly Thr Ile Phe Asn Asn Thr Tyr Asp Gln Leu Met Ile Ala Thr
            100                 105                 110

Gly Ala Lys Pro Ile Ile Pro Pro Ile Asn Asn Ile Asn Leu Glu Asn
        115                 120                 125

Phe His Thr Leu Lys Asn Leu Glu Asp Gly Gln Lys Ile Lys Lys Leu
    130                 135                 140

Met Asp Arg Glu Glu Ile Lys Asn Ile Ala Ile Ile Gly Gly Gly Tyr
145                 150                 155                 160
```

```
Ile Gly Ile Glu Met Val Glu Ala Ala Lys Asn Lys Arg Lys Asn Val
            165                 170                 175

Arg Leu Ile Gln Leu Asp Lys His Ile Leu Ile Asp Ser Phe Asp Glu
        180                 185                 190

Glu Ile Val Thr Ile Met Glu Glu Leu Thr Lys Lys Gly Val Asn
    195                 200                 205

Leu His Thr Asn Glu Phe Val Lys Ser Leu Ile Gly Glu Lys Lys Ala
        210                 215                 220

Gly Val Val Thr Asn Lys Asn Thr Tyr Gln Ala Asp Ala Val Ile
225                 230                 235                 240

Leu Ala Thr Gly Ile Lys Pro Asp Thr Glu Phe Leu Glu Asn Gln Leu
            245                 250                 255

Lys Thr Thr Lys Asn Gly Ala Ile Ile Val Asn Glu Tyr Gly Glu Thr
                260                 265                 270

Ser Ile Lys Asn Ile Phe Ser Ala Gly Asp Cys Ala Thr Ile Tyr Asn
        275                 280                 285

Ile Val Ser Lys Lys Asn Glu Tyr Ile Pro Leu Ala Thr Thr Ala Asn
    290                 295                 300

Lys Leu Gly Arg Ile Val Gly Glu Asn Leu Ala Gly Asn His Thr Ala
305                 310                 315                 320

Phe Lys Gly Thr Leu Gly Ser Ala Ser Ile Lys Ile Leu Ser Leu Glu
                325                 330                 335

Ala Ala Arg Thr Gly Leu Thr Glu Lys Asp Ala Lys Arg Leu Gln Ile
            340                 345                 350

Lys Tyr Lys Thr Ile Phe Val Lys Asp Lys Asn His Thr Asn Tyr Tyr
        355                 360                 365

Pro Gly Gln Glu Asp Leu Tyr Ile Lys Leu Ile Tyr Glu Glu Asn Thr
    370                 375                 380

Lys Ile Ile Leu Gly Ala Gln Ala Thr Gly Lys Asn Gly Ala Val Met
385                 390                 395                 400

Arg Ile His Ala Leu Ser Ile Ala Ile Tyr Ser Lys Leu Thr Thr Lys
                405                 410                 415

Glu Leu Arg Met Met Asp Phe Ser Tyr Ser Pro Pro Phe Ser Arg Thr
            420                 425                 430

Trp Asp Ile Leu Asn Ile Ala Gly Asn Ala Ala Lys
        435                 440

<210> SEQ ID NO 11
<211> LENGTH: 1335
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1335)

<400> SEQUENCE: 11 atg atg aaa ata ata att att ggg ggc aca tca gca gga act agt gcc      48
Met Met Lys Ile Ile Ile Ile Gly Gly Thr Ser Ala Gly Thr Ser Ala
1               5                   10                  15 gca gct aaa gca aac cgc tta aac aaa aag cta gac att act atc tat    96
Ala Ala Lys Ala Asn Arg Leu Asn Lys Lys Leu Asp Ile Thr Ile Tyr
                20                  25                  30 gaa aaa aca aat att gta tct ttt gga acc tgt ggc ctg cct tac ttt   144
Glu Lys Thr Asn Ile Val Ser Phe Gly Thr Cys Gly Leu Pro Tyr Phe
            35                  40                  45
```

-continued

| | |
|---|---|
| gtg ggg gga ttc ttt gac aac ccc aat aca atg atc tca aga aca caa<br>Val Gly Gly Phe Phe Asp Asn Pro Asn Thr Met Ile Ser Arg Thr Gln<br>50                                55                        60 | 192 |
| gaa gaa ttc gaa aaa act gga atc tct gtt aaa act aac cac gaa gtt<br>Glu Glu Phe Glu Lys Thr Gly Ile Ser Val Lys Thr Asn His Glu Val<br>65                                70                        75                        80 | 240 |
| atc aaa gta gat gca aaa aac aat aca att gta ata aaa aat caa aaa<br>Ile Lys Val Asp Ala Lys Asn Asn Thr Ile Val Ile Lys Asn Gln Lys<br>                        85                                90                        95 | 288 |
| aca gga acc att ttt aac aat act tac gat caa ctt atg ata gca act<br>Thr Gly Thr Ile Phe Asn Asn Thr Tyr Asp Gln Leu Met Ile Ala Thr<br>                    100                          105                     110 | 336 |
| ggt gca aaa cct att att cca cca atc aat aat atc aat cta gaa aat<br>Gly Ala Lys Pro Ile Ile Pro Pro Ile Asn Asn Ile Asn Leu Glu Asn<br>               115                       120                     125 | 384 |
| ttt cat act ctg aaa aat tta gaa gac ggt caa aaa ata aaa aaa tta<br>Phe His Thr Leu Lys Asn Leu Glu Asp Gly Gln Lys Ile Lys Lys Leu<br>130                               135                              140 | 432 |
| atg gat aga gaa gag att aaa aat ata gtg ata att ggt ggt gga tac<br>Met Asp Arg Glu Glu Ile Lys Asn Ile Val Ile Ile Gly Gly Gly Tyr<br>145                               150                          155                     160 | 480 |
| att gga att gaa atg gta gaa gca gca aaa aat aaa aga aaa agt gta<br>Ile Gly Ile Glu Met Val Glu Ala Ala Lys Asn Lys Arg Lys Ser Val<br>                    165                          170                     175 | 528 |
| aga tta att caa cta gat aag cac ata ctc ata gat tcc ttt gac gaa<br>Arg Leu Ile Gln Leu Asp Lys His Ile Leu Ile Asp Ser Phe Asp Glu<br>               180                       185                     190 | 576 |
| gaa ata gtc aca ata atg gaa gaa gaa cta aca aaa aag ggg gtt aat<br>Glu Ile Val Thr Ile Met Glu Glu Glu Leu Thr Lys Lys Gly Val Asn<br>                    195                          200                     205 | 624 |
| ctt cat aca aat gag ttt gta aaa agt tta ata gga gga aaa aag gca<br>Leu His Thr Asn Glu Phe Val Lys Ser Leu Ile Gly Gly Lys Lys Ala<br>210                               215                             220 | 672 |
| gaa gga gta gta aca aac aaa aat act tat caa gct gac gct gtt ata<br>Glu Gly Val Val Thr Asn Lys Asn Thr Tyr Gln Ala Asp Ala Val Ile<br>225                               230                          235                     240 | 720 |
| ctt gct acc gga ata aaa cct gac act gaa ttt tta gaa aac cag ctt<br>Leu Ala Thr Gly Ile Lys Pro Asp Thr Glu Phe Leu Glu Asn Gln Leu<br>                    245                          250                     255 | 768 |
| aaa act act aaa aat gga gca ata att gta aat gag tat ggc gaa act<br>Lys Thr Thr Lys Asn Gly Ala Ile Ile Val Asn Glu Tyr Gly Glu Thr<br>                        260                          265                     270 | 816 |
| agc ata aaa aat att ttt tct gca gga gat tgt gca act att tat aat<br>Ser Ile Lys Asn Ile Phe Ser Ala Gly Asp Cys Ala Thr Ile Tyr Asn<br>               275                       280                     285 | 864 |
| ata gta agt aaa aaa aat gaa tac ata ccc ttg gca aca aca gcc aac<br>Ile Val Ser Lys Lys Asn Glu Tyr Ile Pro Leu Ala Thr Thr Ala Asn<br>290                               295                          300 | 912 |
| aaa ctt gga aga ata gtt ggt gaa aat tta gct ggg aat cat aca gca<br>Lys Leu Gly Arg Ile Val Gly Glu Asn Leu Ala Gly Asn His Thr Ala<br>305                               310                          315                     320 | 960 |
| ttt aaa ggc aca ttg ggc tca gct tca att aaa ata cta tct tta gaa<br>Phe Lys Gly Thr Leu Gly Ser Ala Ser Ile Lys Ile Leu Ser Leu Glu<br>                    325                          330                     335 | 1008 |
| gct gca aga aca gga ctt aca gaa aaa gat gca aaa aag ctc caa ata<br>Ala Ala Arg Thr Gly Leu Thr Glu Lys Asp Ala Lys Lys Leu Gln Ile<br>               340                       345                     350 | 1056 |
| aaa tat aaa acg att ttt gta aag gac aaa aat cat aca aat tat tat<br>Lys Tyr Lys Thr Ile Phe Val Lys Asp Lys Asn His Thr Asn Tyr Tyr | 1104 |

```
                355                 360                 365
cca ggc caa gaa gat ctt tat att aaa tta att tat gag gaa aat acc    1152
Pro Gly Gln Glu Asp Leu Tyr Ile Lys Leu Ile Tyr Glu Glu Asn Thr
        370                 375                 380 aaa ata atc ctt ggg gca caa gca ata gga aaa aat gga gcc gta ata    1200
Lys Ile Ile Leu Gly Ala Gln Ala Ile Gly Lys Asn Gly Ala Val Ile
385                 390                 395                 400 aga att cat gct tta tca att gca atc tat tca aag ctt aca aca aaa    1248
Arg Ile His Ala Leu Ser Ile Ala Ile Tyr Ser Lys Leu Thr Thr Lys
                405                 410                 415 gag cta ggg atg atg gat ttc tca tat tcc cca ccc ttc tca aga act    1296
Glu Leu Gly Met Met Asp Phe Ser Tyr Ser Pro Pro Phe Ser Arg Thr
            420                 425                 430 tgg gat ata tta aat att gct ggc aat gct gcc aaa tag                1335
Trp Asp Ile Leu Asn Ile Ala Gly Asn Ala Ala Lys
                435                 440

<210> SEQ ID NO 12
<211> LENGTH: 444
<212> TYPE: PRT
<213> ORGANISM: Artificial Sequence
<220> FEATURE:
<223> OTHER INFORMATION: Synthetic

<400> SEQUENCE: 12

Met Met Lys Ile Ile Ile Gly Gly Thr Ser Ala Gly Thr Ser Ala
1               5                   10                  15

Ala Ala Lys Ala Asn Arg Leu Asn Lys Lys Leu Asp Ile Thr Ile Tyr
                20                  25                  30

Glu Lys Thr Asn Ile Val Ser Phe Gly Thr Cys Gly Leu Pro Tyr Phe
            35                  40                  45

Val Gly Gly Phe Phe Asp Asn Pro Asn Thr Met Ile Ser Arg Thr Gln
    50                  55                  60

Glu Glu Phe Glu Lys Thr Gly Ile Ser Val Lys Thr Asn His Glu Val
65                  70                  75                  80

Ile Lys Val Asp Ala Lys Asn Asn Thr Ile Val Ile Lys Asn Gln Lys
                85                  90                  95

Thr Gly Thr Ile Phe Asn Asn Thr Tyr Asp Gln Leu Met Ile Ala Thr
            100                 105                 110

Gly Ala Lys Pro Ile Ile Pro Pro Ile Asn Asn Ile Asn Leu Glu Asn
        115                 120                 125

Phe His Thr Leu Lys Asn Leu Glu Asp Gly Gln Lys Ile Lys Lys Leu
    130                 135                 140

Met Asp Arg Glu Glu Ile Lys Asn Ile Val Ile Gly Gly Gly Tyr
145                 150                 155                 160

Ile Gly Ile Glu Met Val Glu Ala Ala Lys Asn Lys Arg Lys Ser Val
                165                 170                 175

Arg Leu Ile Gln Leu Asp Lys His Ile Leu Ile Asp Ser Phe Asp Glu
            180                 185                 190

Glu Ile Val Thr Ile Met Glu Glu Leu Thr Lys Lys Gly Val Asn
        195                 200                 205

Leu His Thr Asn Glu Phe Val Lys Ser Leu Ile Gly Gly Lys Lys Ala
    210                 215                 220

Glu Gly Val Val Thr Asn Lys Asn Thr Tyr Gln Ala Asp Ala Val Ile
225                 230                 235                 240

Leu Ala Thr Gly Ile Lys Pro Asp Thr Glu Phe Leu Glu Asn Gln Leu
                245                 250                 255
```

```
Lys Thr Thr Lys Asn Gly Ala Ile Ile Val Asn Glu Tyr Gly Glu Thr
            260                 265                 270

Ser Ile Lys Asn Ile Phe Ser Ala Gly Asp Cys Ala Thr Ile Tyr Asn
        275                 280                 285

Ile Val Ser Lys Lys Asn Glu Tyr Ile Pro Leu Ala Thr Thr Ala Asn
    290                 295                 300

Lys Leu Gly Arg Ile Val Gly Glu Asn Leu Ala Gly Asn His Thr Ala
305                 310                 315                 320

Phe Lys Gly Thr Leu Gly Ser Ala Ser Ile Lys Ile Leu Ser Leu Glu
                325                 330                 335

Ala Ala Arg Thr Gly Leu Thr Glu Lys Asp Ala Lys Lys Leu Gln Ile
                340                 345                 350

Lys Tyr Lys Thr Ile Phe Val Lys Asp Lys Asn His Thr Asn Tyr Tyr
            355                 360                 365

Pro Gly Gln Glu Asp Leu Tyr Ile Lys Leu Ile Tyr Glu Glu Asn Thr
        370                 375                 380

Lys Ile Ile Leu Gly Ala Gln Ala Ile Gly Lys Asn Gly Ala Val Ile
385                 390                 395                 400

Arg Ile His Ala Leu Ser Ile Ala Ile Tyr Ser Lys Leu Thr Thr Lys
                405                 410                 415

Glu Leu Gly Met Met Asp Phe Ser Tyr Ser Pro Pro Phe Ser Arg Thr
                420                 425                 430

Trp Asp Ile Leu Asn Ile Ala Gly Asn Ala Ala Lys
            435                 440

<210> SEQ ID NO 13
<211> LENGTH: 37
<212> TYPE: DNA
<213> ORGANISM: Artificial Sequence
<220> FEATURE:
<223> OTHER INFORMATION: Synthetic

<400> SEQUENCE: 13
gcgcgaattc atgaaagtta ttgtagtagg ttgtact                    37

<210> SEQ ID NO 14
<211> LENGTH: 37
<212> TYPE: DNA
<213> ORGANISM: Artificial Sequence
<220> FEATURE:
<223> OTHER INFORMATION: Synthetic

<400> SEQUENCE: 14
gcgcaagctt ttatttatgt gctttgtcag cttgtgc                    37

<210> SEQ ID NO 15
<211> LENGTH: 36
<212> TYPE: DNA
<213> ORGANISM: Artificial Sequence
<220> FEATURE:
<223> OTHER INFORMATION: Synthetic

<400> SEQUENCE: 15
gcgcggatcc atgatgaaaa taataattat tggggg                     36

<210> SEQ ID NO 16
<211> LENGTH: 37
<212> TYPE: DNA
<213> ORGANISM: Artificial Sequence
<220> FEATURE:
```

<223> OTHER INFORMATION: Synthetic

<400> SEQUENCE: 16
gcgcaagctt ctatttggca gcattgccag caatatt                37

<210> SEQ ID NO 17
<211> LENGTH: 452
<212> TYPE: PRT
<213> ORGANISM: Artificial Sequence
<220> FEATURE:
<223> OTHER INFORMATION: Synthetic

<400> SEQUENCE: 17

```
Met Lys Val Ile Val Val Gly Cys Thr His Ala Gly Thr Phe Ala Val
1               5                   10                  15

Lys Gln Thr Ile Ala Asp His Pro Asp Ala Asp Val Thr Ala Tyr Glu
            20                  25                  30

Met Asn Asp Asn Ile Ser Phe Leu Ser Ser Gly Ile Ala Leu Tyr Leu
        35                  40                  45

Gly Lys Glu Ile Lys Asn Asn Asp Pro Arg Gly Leu Phe Tyr Ser Ser
    50                  55                  60

Pro Glu Glu Leu Ser Asn Leu Gly Ala Asn Val Gln Met Arg His Gln
65                  70                  75                  80

Val Thr Asn Val Asp Pro Glu Thr Lys Thr Ile Lys Val Lys Asp Leu
                85                  90                  95

Ile Thr Asn Glu Glu Lys Thr Glu Ala Tyr Asp Lys Leu Ile Met Thr
            100                 105                 110

Thr Gly Ser Lys Pro Thr Val Pro Pro Ile Pro Gly Ile Asp Ser Ser
        115                 120                 125

Arg Val Tyr Leu Cys Lys Asn Tyr Asn Asp Ala Lys Lys Leu Phe Glu
    130                 135                 140

Glu Ala Pro Lys Ala Lys Thr Ile Thr Ile Ile Gly Ser Gly Tyr Ile
145                 150                 155                 160

Gly Ala Glu Leu Ala Glu Ala Tyr Ser Asn Gln Asn Tyr Asn Val Asn
                165                 170                 175

Leu Ile Asp Gly His Glu Arg Val Leu Tyr Lys Tyr Phe Asp Lys Glu
            180                 185                 190

Phe Thr Asp Ile Leu Ala Lys Asp Tyr Glu Ala His Gly Val Asn Leu
        195                 200                 205

Val Leu Gly Ser Lys Val Ala Ala Phe Glu Glu Val Asp Asp Glu Ile
    210                 215                 220

Ile Thr Lys Thr Leu Asp Gly Lys Glu Ile Lys Ser Asp Ile Ala Ile
225                 230                 235                 240

Leu Cys Ile Gly Phe Arg Pro Asn Thr Glu Leu Leu Lys Gly Lys Val
                245                 250                 255

Ala Met Leu Asp Asn Gly Ala Ile Ile Thr Asp Glu Tyr Met His Ser
            260                 265                 270

Ser Asn Arg Asp Ile Phe Ala Ala Gly Asp Ser Ala Ala Val His Tyr
        275                 280                 285

Asn Pro Thr Asn Ser Asn Ala Tyr Ile Pro Leu Ala Thr Asn Ala Val
    290                 295                 300

Arg Gln Gly Arg Leu Val Gly Leu Asn Leu Thr Glu Asp Lys Val Lys
305                 310                 315                 320

Asp Met Gly Thr Gln Ser Ser Ser Gly Leu Lys Leu Tyr Gly Arg Thr
                325                 330                 335
```

```
Tyr Val Ser Thr Gly Ile Asn Thr Ala Leu Ala Lys Ala Asn Asn Leu
            340                 345                 350

Lys Val Ser Glu Val Ile Ile Ala Asp Asn Tyr Arg Pro Glu Phe Met
            355                 360                 365

Leu Ser Thr Asp Glu Val Leu Met Ser Leu Val Tyr Asp Pro Lys Thr
            370                 375                 380

Arg Val Ile Leu Gly Gly Ala Leu Ser Ser Met His Asp Val Ser Gln
385                 390                 395                 400

Ser Ala Asn Val Leu Ser Val Cys Ile Gln Asn Lys Asn Thr Ile Asp
            405                 410                 415

Asp Leu Ala Met Val Asp Met Leu Phe Gln Pro Gln Phe Asp Arg Pro
            420                 425                 430

Phe Asn Tyr Leu Asn Ile Leu Gly Gln Ala Ala Gln Ala Gln Ala Asp
            435                 440                 445

Lys Ala His Lys
        450
```

<210> SEQ ID NO 18
<211> LENGTH: 452
<212> TYPE: PRT
<213> ORGANISM: Artificial Sequence
<220> FEATURE:
<223> OTHER INFORMATION: Synthetic

<400> SEQUENCE: 18

```
Met Lys Val Ile Val Gly Cys Thr His Ala Gly Thr Phe Ala Val
1               5                   10                  15

Lys Gln Thr Ile Ala Asp His Pro Asp Ala Asp Val Thr Ala Tyr Glu
            20                  25                  30

Met Asn Asp Asn Ile Ser Phe Leu Ser Met Gly Ile Ala Leu Tyr Leu
            35                  40                  45

Gly Lys Glu Ile Lys Asn Asn Asp Pro Arg Gly Leu Phe Tyr Ser Ser
50                  55                  60

Pro Glu Glu Leu Ser Asn Leu Gly Ala Asn Val Gln Met Arg His Gln
65                  70                  75                  80

Val Thr Asn Val Asp Pro Glu Thr Lys Thr Ile Lys Val Lys Asp Leu
            85                  90                  95

Ile Thr Asn Glu Glu Lys Thr Glu Ala Tyr Asp Lys Leu Ile Met Thr
            100                 105                 110

Thr Gly Ser Lys Pro Thr Val Pro Pro Ile Pro Gly Ile Asp Ser Ser
            115                 120                 125

Arg Val Tyr Leu Cys Lys Asn Tyr Asn Asp Ala Lys Lys Leu Phe Glu
            130                 135                 140

Glu Ala Pro Lys Ala Lys Thr Ile Thr Ile Ile Gly Ser Gly Tyr Ile
145                 150                 155                 160

Gly Ala Glu Leu Ala Glu Ala Tyr Ser Asn Gln Asn Tyr Asn Val Asn
            165                 170                 175

Leu Ile Asp Gly His Glu Arg Val Leu Tyr Lys Tyr Phe Asp Lys Glu
            180                 185                 190

Phe Thr Asp Ile Leu Ala Lys Asp Tyr Glu Ala His Gly Val Asn Leu
            195                 200                 205

Val Leu Gly Ser Lys Val Ala Ala Phe Glu Glu Val Asp Asp Glu Ile
            210                 215                 220

Ile Thr Lys Thr Leu Asp Gly Lys Glu Ile Lys Ser Asp Ile Ala Ile
225                 230                 235                 240
```

```
Leu Cys Ile Gly Phe Arg Pro Asn Thr Glu Leu Leu Lys Gly Lys Val
                245                 250                 255

Ala Met Leu Asp Asn Gly Ala Ile Ile Thr Asp Glu Tyr Met His Ser
                260                 265                 270

Ser Asn Arg Asp Ile Phe Ala Ala Gly Asp Ser Ala Ala Val His Tyr
                275                 280                 285

Asn Pro Thr Asn Ser Asn Ala Tyr Ile Pro Leu Ala Thr Asn Ala Val
                290                 295                 300

Arg Gln Gly Arg Leu Val Gly Leu Asn Leu Thr Glu Asp Lys Val Lys
305                 310                 315                 320

Asp Met Gly Thr Gln Ser Ser Gly Leu Lys Leu Tyr Gly Arg Thr
                325                 330                 335

Tyr Val Ser Thr Gly Ile Asn Thr Ala Leu Ala Lys Ala Asn Asn Leu
                340                 345                 350

Lys Val Ser Glu Val Ile Ala Asp Asn Tyr Arg Pro Glu Phe Met
                355                 360                 365

Leu Ser Thr Asp Glu Val Leu Met Ser Leu Val Tyr Asp Pro Lys Thr
                370                 375                 380

Arg Val Ile Leu Gly Gly Ala Leu Ser Ser Met His Asp Val Ser Gln
385                 390                 395                 400

Ser Ala Asn Val Leu Ser Val Cys Ile Gln Asn Lys Asn Thr Ile Asp
                405                 410                 415

Asp Leu Ala Met Val Asp Met Leu Phe Gln Pro Gln Phe Asp Arg Pro
                420                 425                 430

Phe Asn Tyr Leu Asn Ile Leu Gly Gln Ala Ala Gln Ala Gln Ala Asp
                435                 440                 445

Lys Ala His Lys
        450

<210> SEQ ID NO 19
<211> LENGTH: 452
<212> TYPE: PRT
<213> ORGANISM: Artificial Sequence
<220> FEATURE:
<223> OTHER INFORMATION: Synthetic

<400> SEQUENCE: 19

Met Lys Val Ile Val Val Gly Cys Thr His Ala Gly Thr Phe Ala Val
1               5                   10                  15

Lys Gln Thr Ile Ala Asp His Pro Asp Ala Asp Val Thr Ala Tyr Glu
                20                  25                  30

Met Asn Asp Asn Ile Ser Phe Leu Ser Ala Gly Ile Ala Leu Tyr Leu
                35                  40                  45

Gly Lys Glu Ile Lys Asn Asn Asp Pro Arg Gly Leu Phe Tyr Ser Ser
        50                  55                  60

Pro Glu Glu Leu Ser Asn Leu Gly Ala Asn Val Gln Met Arg His Gln
65                  70                  75                  80

Val Thr Asn Val Asp Pro Glu Thr Lys Thr Ile Lys Val Lys Asp Leu
                85                  90                  95

Ile Thr Asn Glu Glu Lys Thr Glu Ala Tyr Asp Lys Leu Ile Met Thr
                100                 105                 110

Thr Gly Ser Lys Pro Thr Val Pro Pro Ile Pro Gly Ile Asp Ser Ser
                115                 120                 125

Arg Val Tyr Leu Cys Lys Asn Tyr Asn Asp Ala Lys Lys Leu Phe Glu
                130                 135                 140
```

```
Glu Ala Pro Lys Ala Lys Thr Ile Thr Ile Ile Gly Ser Gly Tyr Ile
145                 150                 155                 160

Gly Ala Glu Leu Ala Glu Ala Tyr Ser Asn Gln Asn Tyr Asn Val Asn
                165                 170                 175

Leu Ile Asp Gly His Glu Arg Val Leu Tyr Lys Tyr Phe Asp Lys Glu
            180                 185                 190

Phe Thr Asp Ile Leu Ala Lys Asp Tyr Glu Ala His Gly Val Asn Leu
        195                 200                 205

Val Leu Gly Ser Lys Val Ala Ala Phe Glu Glu Val Asp Asp Glu Ile
    210                 215                 220

Ile Thr Lys Thr Leu Asp Gly Lys Glu Ile Lys Ser Asp Ile Ala Ile
225                 230                 235                 240

Leu Cys Ile Gly Phe Arg Pro Asn Thr Glu Leu Leu Lys Gly Lys Val
                245                 250                 255

Ala Met Leu Asp Asn Gly Ala Ile Ile Thr Asp Glu Tyr Met His Ser
                260                 265                 270

Ser Asn Arg Asp Ile Phe Ala Ala Gly Asp Ser Ala Ala Val His Tyr
            275                 280                 285

Asn Pro Thr Asn Ser Asn Ala Tyr Ile Pro Leu Ala Thr Asn Ala Val
        290                 295                 300

Arg Gln Gly Arg Leu Val Gly Leu Asn Leu Thr Glu Asp Lys Val Lys
305                 310                 315                 320

Asp Met Gly Thr Gln Ser Ser Gly Leu Lys Leu Tyr Gly Arg Thr
                325                 330                 335

Tyr Val Ser Thr Gly Ile Asn Thr Ala Leu Ala Lys Ala Asn Asn Leu
            340                 345                 350

Lys Val Ser Glu Val Ile Ile Ala Asp Asn Tyr Arg Pro Glu Phe Met
            355                 360                 365

Leu Ser Thr Asp Glu Val Leu Met Ser Leu Val Tyr Asp Pro Lys Thr
        370                 375                 380

Arg Val Ile Leu Gly Gly Ala Leu Ser Ser Met His Asp Val Ser Gln
385                 390                 395                 400

Ser Ala Asn Val Leu Ser Val Cys Ile Gln Asn Lys Asn Thr Ile Asp
                405                 410                 415

Asp Leu Ala Met Val Asp Met Leu Phe Gln Pro Gln Phe Asp Arg Pro
            420                 425                 430

Phe Asn Tyr Leu Asn Ile Leu Gly Gln Ala Ala Gln Ala Gln Ala Asp
        435                 440                 445

Lys Ala His Lys
    450

<210> SEQ ID NO 20
<211> LENGTH: 452
<212> TYPE: PRT
<213> ORGANISM: Artificial Sequence
<220> FEATURE:
<223> OTHER INFORMATION: Synthetic

<400> SEQUENCE: 20

Met Lys Val Ile Val Val Gly Cys Thr His Ala Gly Thr Phe Ala Val
1               5                   10                  15

Lys Gln Thr Ile Ala Asp His Pro Asp Ala Asp Val Thr Ala Tyr Glu
            20                  25                  30

Met Asn Asp Asn Ile Ser Phe Leu Ser Phe Gly Ile Ala Leu Tyr Leu
        35                  40                  45
```

```
Gly Lys Glu Ile Lys Asn Asn Asp Pro Arg Gly Leu Phe Tyr Ser Ser
 50                  55                  60

Pro Glu Glu Leu Ser Asn Leu Gly Ala Asn Val Gln Met Arg His Gln
 65                  70                  75                  80

Val Thr Asn Val Asp Pro Glu Thr Lys Thr Ile Lys Val Lys Asp Leu
                 85                  90                  95

Ile Thr Asn Glu Glu Lys Thr Glu Ala Tyr Asp Lys Leu Ile Met Thr
            100                 105                 110

Thr Gly Ser Lys Pro Thr Val Pro Pro Ile Pro Gly Ile Asp Ser Ser
            115                 120                 125

Arg Val Tyr Leu Cys Lys Asn Tyr Asn Asp Ala Lys Lys Leu Phe Glu
            130                 135                 140

Glu Ala Pro Lys Ala Lys Thr Ile Thr Ile Ile Gly Ser Gly Tyr Ile
145                 150                 155                 160

Gly Ala Glu Leu Ala Glu Ala Tyr Ser Asn Gln Asn Tyr Asn Val Asn
                165                 170                 175

Leu Ile Asp Gly His Glu Arg Val Leu Tyr Lys Tyr Phe Asp Lys Glu
            180                 185                 190

Phe Thr Asp Ile Leu Ala Lys Asp Tyr Glu Ala His Gly Val Asn Leu
            195                 200                 205

Val Leu Gly Ser Lys Val Ala Ala Phe Glu Glu Val Asp Asp Glu Ile
210                 215                 220

Ile Thr Lys Thr Leu Asp Gly Lys Glu Ile Lys Ser Asp Ile Ala Ile
225                 230                 235                 240

Leu Cys Ile Gly Phe Arg Pro Asn Thr Glu Leu Leu Lys Gly Lys Val
                245                 250                 255

Ala Met Leu Asp Asn Gly Ala Ile Ile Thr Asp Glu Tyr Met His Ser
            260                 265                 270

Ser Asn Arg Asp Ile Phe Ala Ala Gly Asp Ser Ala Ala Val His Tyr
            275                 280                 285

Asn Pro Thr Asn Ser Asn Ala Tyr Ile Pro Leu Ala Thr Asn Ala Val
290                 295                 300

Arg Gln Gly Arg Leu Val Gly Leu Asn Leu Thr Glu Asp Lys Val Lys
305                 310                 315                 320

Asp Met Gly Thr Gln Ser Ser Ser Gly Leu Lys Leu Tyr Gly Arg Thr
                325                 330                 335

Tyr Val Ser Thr Gly Ile Asn Thr Ala Leu Ala Lys Ala Asn Asn Leu
            340                 345                 350

Lys Val Ser Glu Val Ile Ile Ala Asp Asn Tyr Arg Pro Glu Phe Met
            355                 360                 365

Leu Ser Thr Asp Glu Val Leu Met Ser Leu Val Tyr Asp Pro Lys Thr
370                 375                 380

Arg Val Ile Leu Gly Gly Ala Leu Ser Ser Met His Asp Val Ser Gln
385                 390                 395                 400

Ser Ala Asn Val Leu Ser Val Cys Ile Gln Asn Lys Asn Thr Ile Asp
                405                 410                 415

Asp Leu Ala Met Val Asp Met Leu Phe Gln Pro Gln Phe Asp Arg Pro
            420                 425                 430

Phe Asn Tyr Leu Asn Ile Leu Gly Gln Ala Ala Gln Ala Gln Ala Asp
            435                 440                 445

Lys Ala His Lys
450
```